US008636653B2

(12) United States Patent
Wilson

(10) Patent No.: US 8,636,653 B2
(45) Date of Patent: Jan. 28, 2014

(54) IN VIVO CAMERA WITH MULTIPLE SOURCES TO ILLUMINATE TISSUE AT DIFFERENT DISTANCES

(75) Inventor: Gordon C. Wilson, San Francisco, CA (US)

(73) Assignee: Capso Vision, Inc., Saratoga, CA (US)

(*) Notice: Subject to any disclaimer, the term of this patent is extended or adjusted under 35 U.S.C. 154(b) by 796 days.

(21) Appl. No.: 12/475,435

(22) Filed: May 29, 2009

(65) Prior Publication Data

US 2009/0306474 A1 Dec. 10, 2009

Related U.S. Application Data

(60) Provisional application No. 61/060,068, filed on Jun. 9, 2008.

(51) Int. Cl.
*A61B 1/06* (2006.01)
*A61B 5/05* (2006.01)
*A61B 1/04* (2006.01)
*G01C 21/02* (2006.01)
*G01J 1/42* (2006.01)

(52) U.S. Cl.
USPC .......... 600/160; 600/178; 600/425; 600/109; 250/206.1; 250/208.2; 362/574

(58) Field of Classification Search
USPC .......... 600/177, 178, 179, 180, 181, 182, 22, 600/425, 473, 476, 310, 32, 109, 459, 160; 348/68, 280, 223.1, 222.1; 362/574; 356/436, 301; 607/92, 110, 90, 2, 88, 607/89; 250/461.1
See application file for complete search history.

(56) References Cited

U.S. PATENT DOCUMENTS

| 4,278,077 A | 7/1981 | Mizumoto |
| 4,566,763 A | 1/1986 | Greguss |

(Continued)

FOREIGN PATENT DOCUMENTS

| JP | 2003-260025 | 9/2003 |
| JP | 2005-334647 | 12/2005 |

(Continued)

OTHER PUBLICATIONS

Entire Prosecution History of U.S. Appl. No. 11/642,275, filed on Dec. 19, 2006 by Kang-Huai Wang et al.

(Continued)

*Primary Examiner* — John P Leubecker
*Assistant Examiner* — Ronald D Colque
(74) *Attorney, Agent, or Firm* — Silicon Valley Patent Group LLP

(57) ABSTRACT

An in vivo endoscope illuminates tissue using multiple sources. Light from a short-range source exits a tubular wall of the endoscope through a first illumination region that overlaps an imaging region, and the light returns through the imaging region after reflection by tissue, to form an image in a camera. Light from a long-range source exits the tubular wall through a second illumination region that does not overlap the imaging region. The endoscope of some embodiments includes a mirror, and light from an emitter for the short-range source is split and reaches the first illumination region from both sides of an optical axis of the camera. Illuminating the first illumination region with split fractions of light results in greater uniformity of illumination, than illuminating directly with an un-split beam. The energy generated by each source is changed depending on distance of the tissue to be imaged.

54 Claims, 45 Drawing Sheets

(56) References Cited

U.S. PATENT DOCUMENTS

| | | | |
|---|---|---|---|
| 5,473,474 | A | 12/1995 | Powell |
| 5,584,557 | A | 12/1996 | Alexay |
| 5,604,531 | A | 2/1997 | Iddan et al. |
| 6,124,883 | A | 9/2000 | Suzuki et al. |
| 6,428,469 | B1 | 8/2002 | Iddan et al. |
| 6,709,387 | B1 | 3/2004 | Glukhovsky et al. |
| 6,800,060 | B2 | 10/2004 | Marshall |
| 6,836,377 | B1 | 12/2004 | Kislev et al. |
| 6,855,111 | B2 | 2/2005 | Yokoi et al. |
| 6,918,872 | B2 | 7/2005 | Yokoi et al. |
| 6,963,175 | B2 | 11/2005 | Archenhold et al. |
| 7,118,529 | B2 | 10/2006 | Glukhovsky et al. |
| 7,264,584 | B2 | 9/2007 | Ritter et al. |
| 7,311,708 | B2 | 12/2007 | McClurken |
| 7,321,126 | B2 | 1/2008 | Singer et al. |
| 7,341,557 | B2 | 3/2008 | Cline et al. |
| 7,379,561 | B2 | 5/2008 | Chauville et al. |
| 7,796,870 | B2 | 9/2010 | Wang |
| 7,801,584 | B2 * | 9/2010 | Iddan et al. ............ 600/407 |
| 7,896,805 | B2 | 3/2011 | Gilad et al. |
| 7,959,563 | B2 * | 6/2011 | Fukuhori ............ 600/175 |
| 7,983,458 | B2 | 7/2011 | Wang et al. |
| 2002/0109774 | A1 | 8/2002 | Meron et al. |
| 2003/0117491 | A1 | 6/2003 | Avni et al. |
| 2003/0171653 | A1 * | 9/2003 | Yokoi et al. ............ 600/160 |
| 2004/0092825 | A1 | 5/2004 | Madar et al. |
| 2004/0225189 | A1 * | 11/2004 | Kimoto et al. ............ 600/160 |
| 2004/0249245 | A1 * | 12/2004 | Irion ............ 600/160 |
| 2005/0004474 | A1 | 1/2005 | Iddan |
| 2005/0049462 | A1 | 3/2005 | Kanazawa |
| 2005/0143624 | A1 | 6/2005 | Iddan |
| 2005/0143644 | A1 | 6/2005 | Gilad et al. |
| 2005/0146644 | A1 | 7/2005 | Miyazawa et al. |
| 2006/0178557 | A1 | 8/2006 | Mintchev et al. |
| 2006/0217593 | A1 | 9/2006 | Gilad et al. |
| 2007/0055105 | A1 | 3/2007 | Matsuzawa et al. |
| 2007/0055106 | A1 * | 3/2007 | Moriyama ............ 600/178 |
| 2008/0045789 | A1 * | 2/2008 | Sawachi ............ 600/111 |
| 2008/0143822 | A1 | 6/2008 | Wang et al. |
| 2008/0161647 | A1 * | 7/2008 | Pascal ............ 600/178 |
| 2008/0221447 | A1 * | 9/2008 | Igarashi et al. ............ 600/437 |

FOREIGN PATENT DOCUMENTS

| | | |
|---|---|---|
| WO | 2004/032621 | 4/2004 |
| WO | 2004/096008 | 11/2004 |
| WO | 2008/012701 | 1/2008 |

OTHER PUBLICATIONS

Entire Prosecution History of U.S. Appl. No. 12/463,488, filed on May 11, 2009 by Gordon Wilson et al.
Cree® EZBright290™ LEDs Data Sheet, CxxxEZ290-Sxx00, 2006-2007, p. 1-6.
Winston, R. et al. "Nonimaging Optics", Elsevier Academic Press, 2005, p. 50-55, 80-83, 467-469, 473-475.
Mone, G. "How it works: The Endoscope Camera in a Pill", posted Mar. 13, 2008, p. 1-3.
PillCam Colon, believed to be prior to May 29, 2009 p. 1-2.
International Search Report and Written Opinion dated Jul. 21, 2009, International Application No. PCT/US2009/045829, p. 1-10.
U.S. Appl. No. 11/642,275, dated Dec. 19, 2006.
Office Action dated Jun. 27, 2011 in U.S. Appl. No. 11/642,275.
Amendment dated Sep. 27, 2011 in U.S. Appl. No. 11/642,275.
Notice of Allowance dated Dec. 21, 2011 in U.S. Appl. No. 11/642,275.
Amendment dated Mar. 21, 2012 in U.S. Appl. No. 11/642,275.
Notice of Allowance dated Apr. 1, 2013 in U.S. Appl. No. 11/642,275.
Amendment filed with Request for Continued Examination dated Jun. 28, 2013 in U.S. Appl. No. 11/642,275.
Supplementary European Search Report dated Jun. 25, 2013 in European Patent Application 09763283.0, 8 pages.
Chinese Office Action, dated Oct. 10, 2012 in Chinese Patent Application No. 200980120587.7, 6 pages.
Chinese Office Action, dated Jun. 28, 2013 in Chinese Patent Application No. 200980120587.7, 9 pages.

* cited by examiner

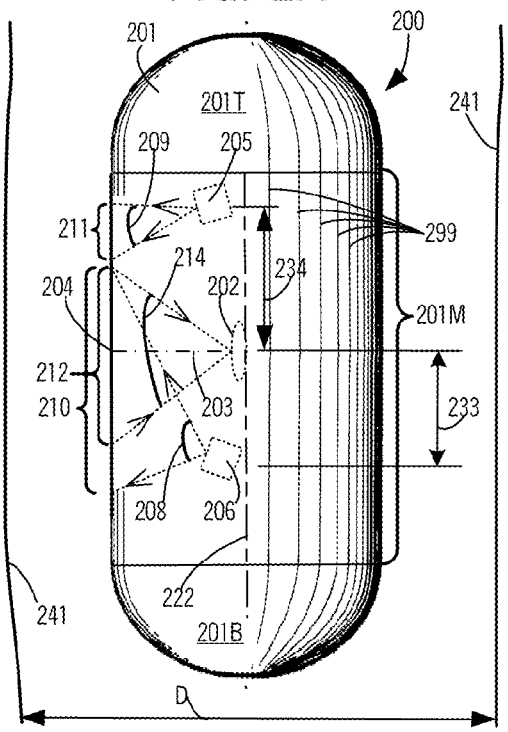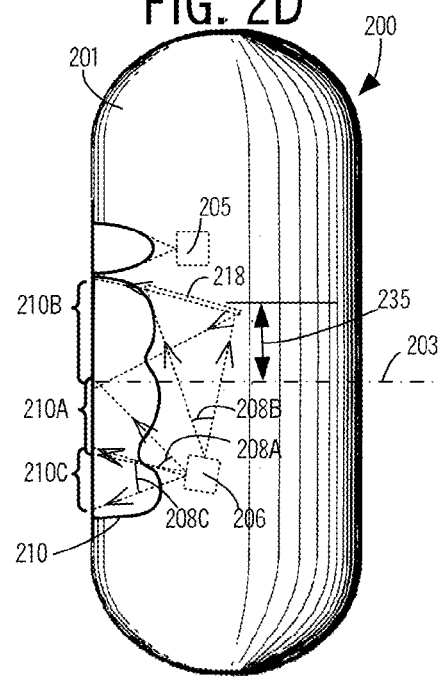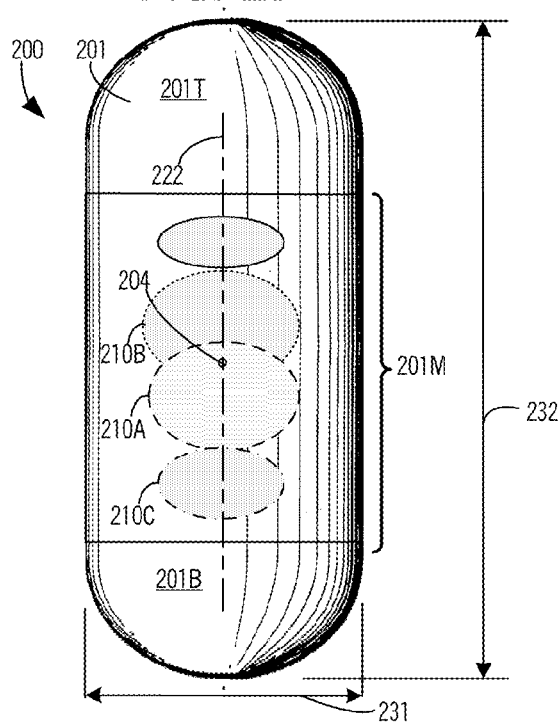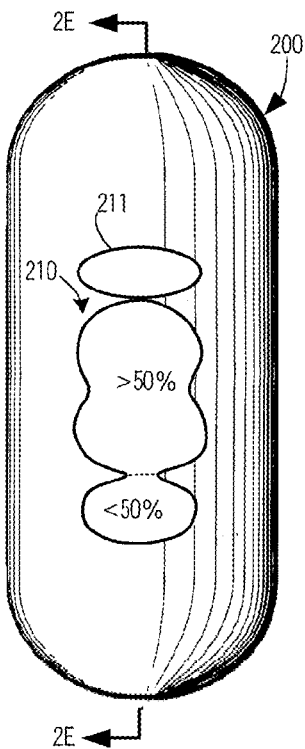

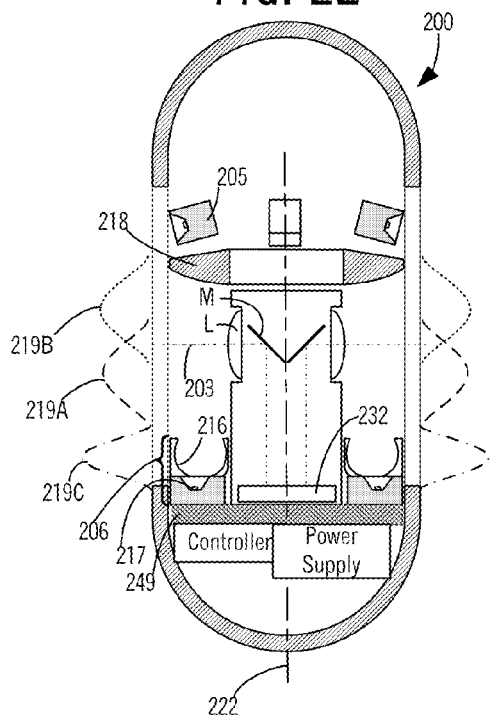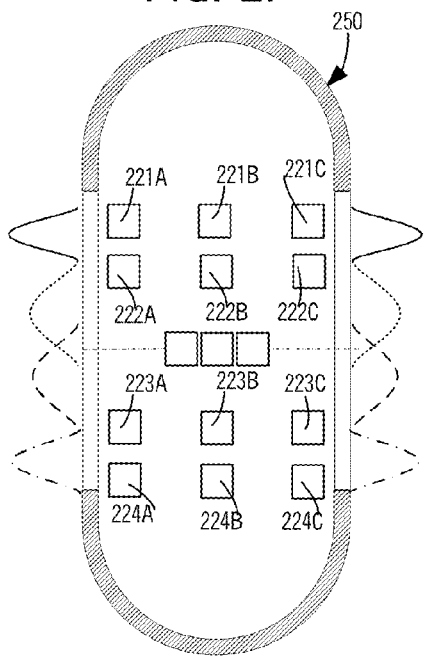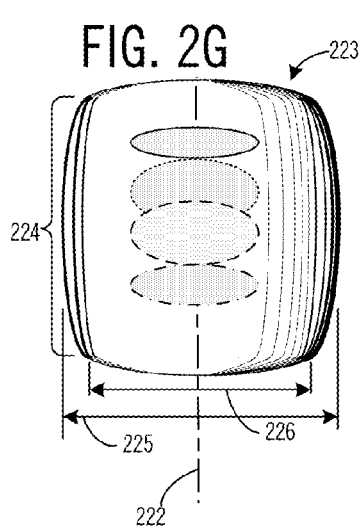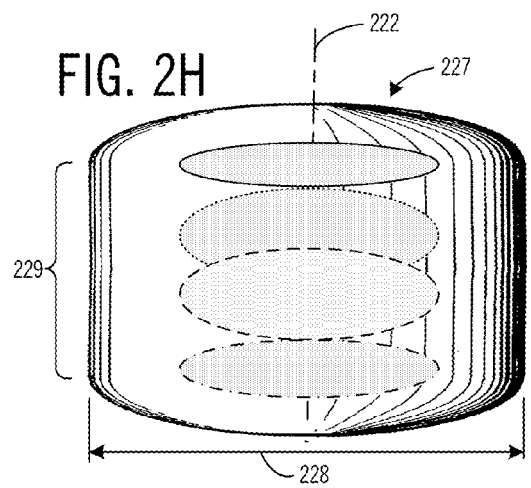

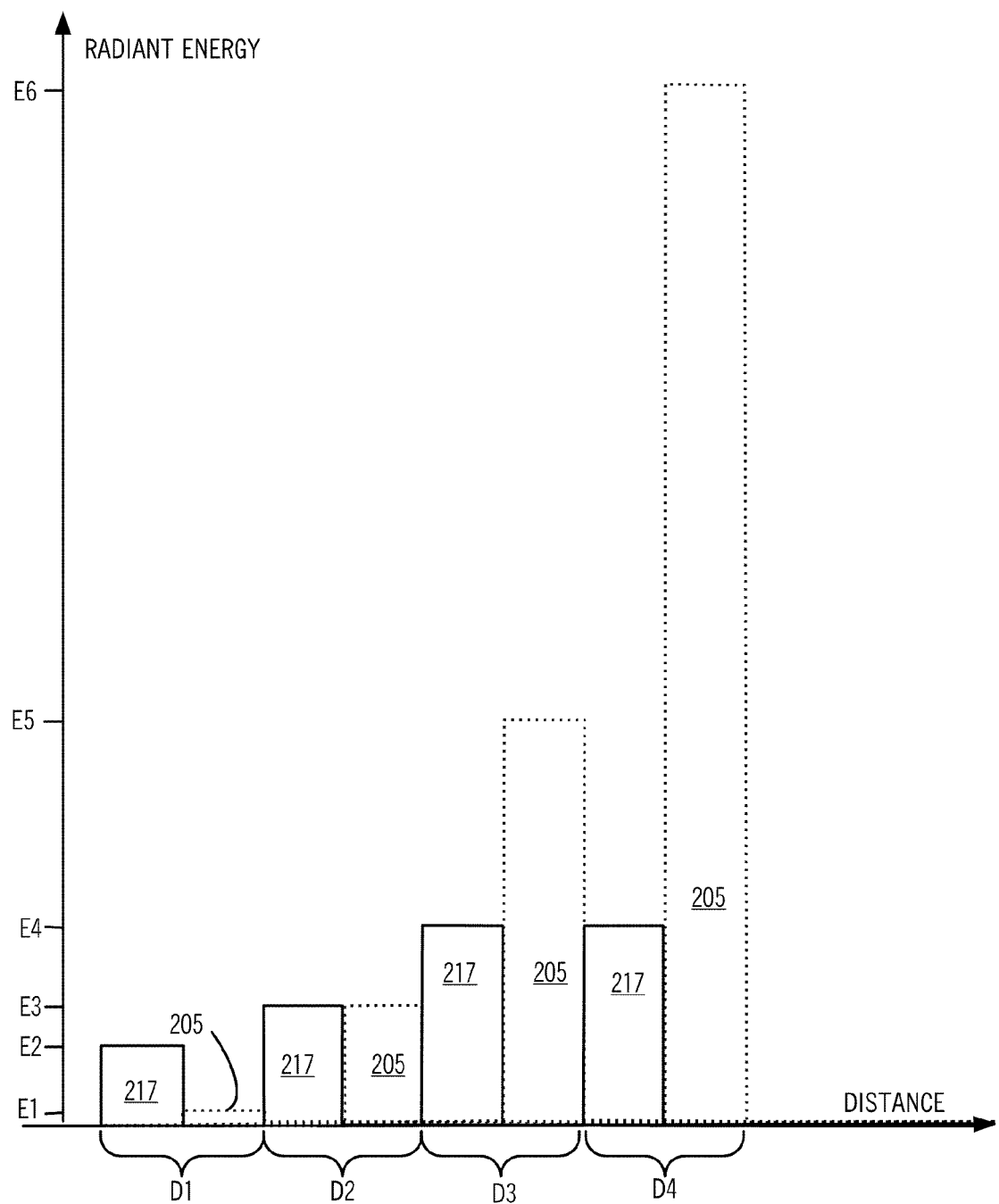

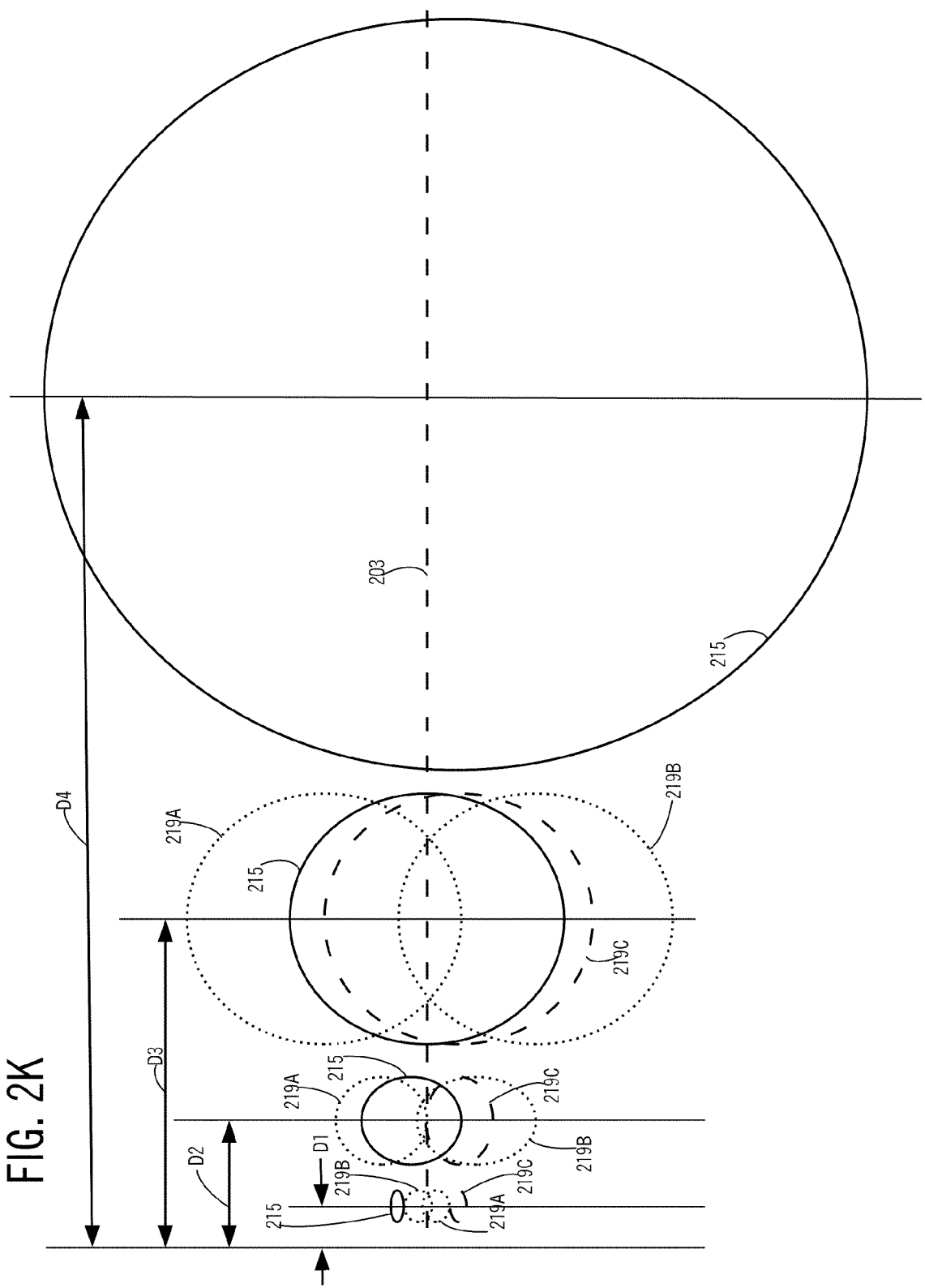

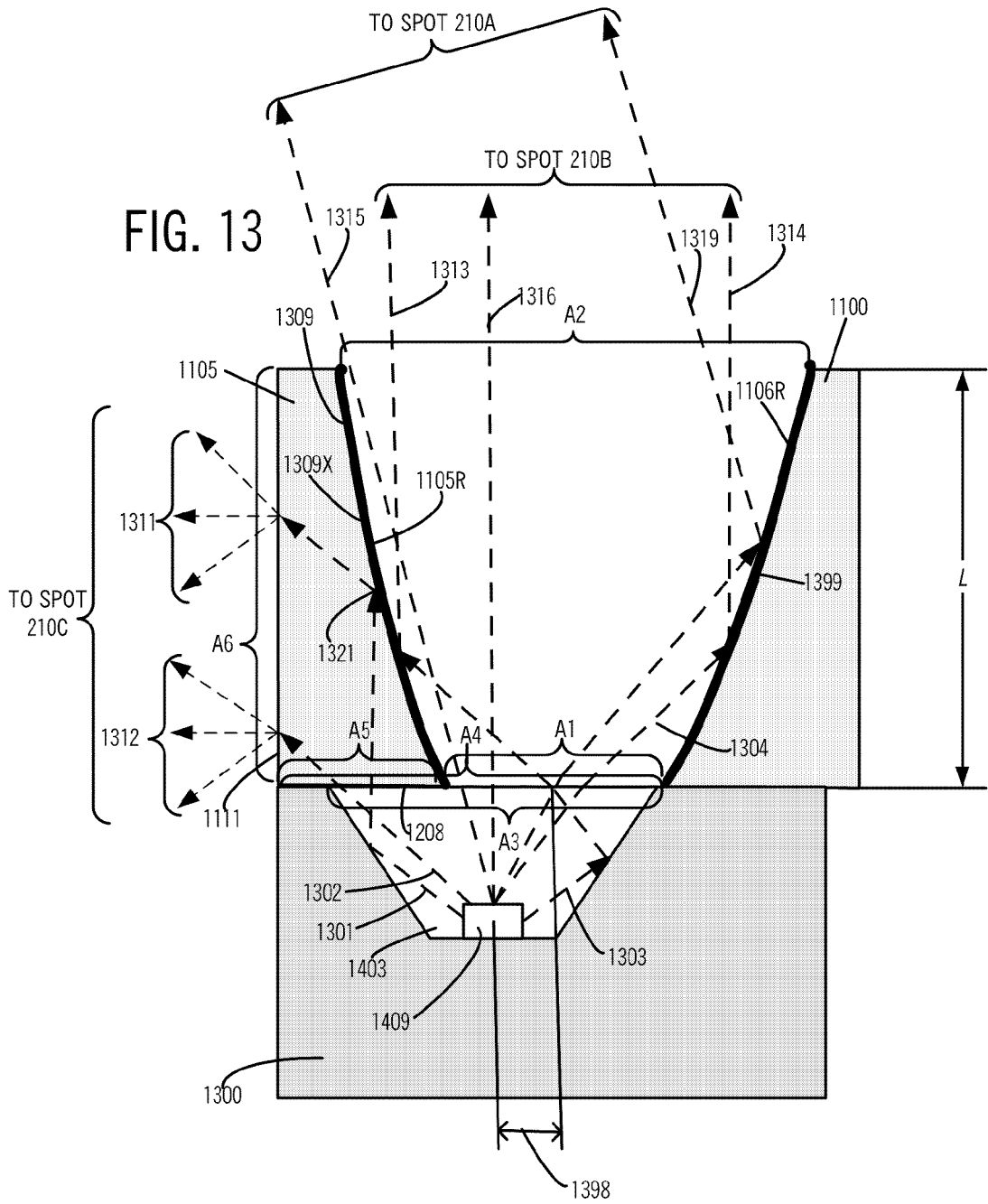

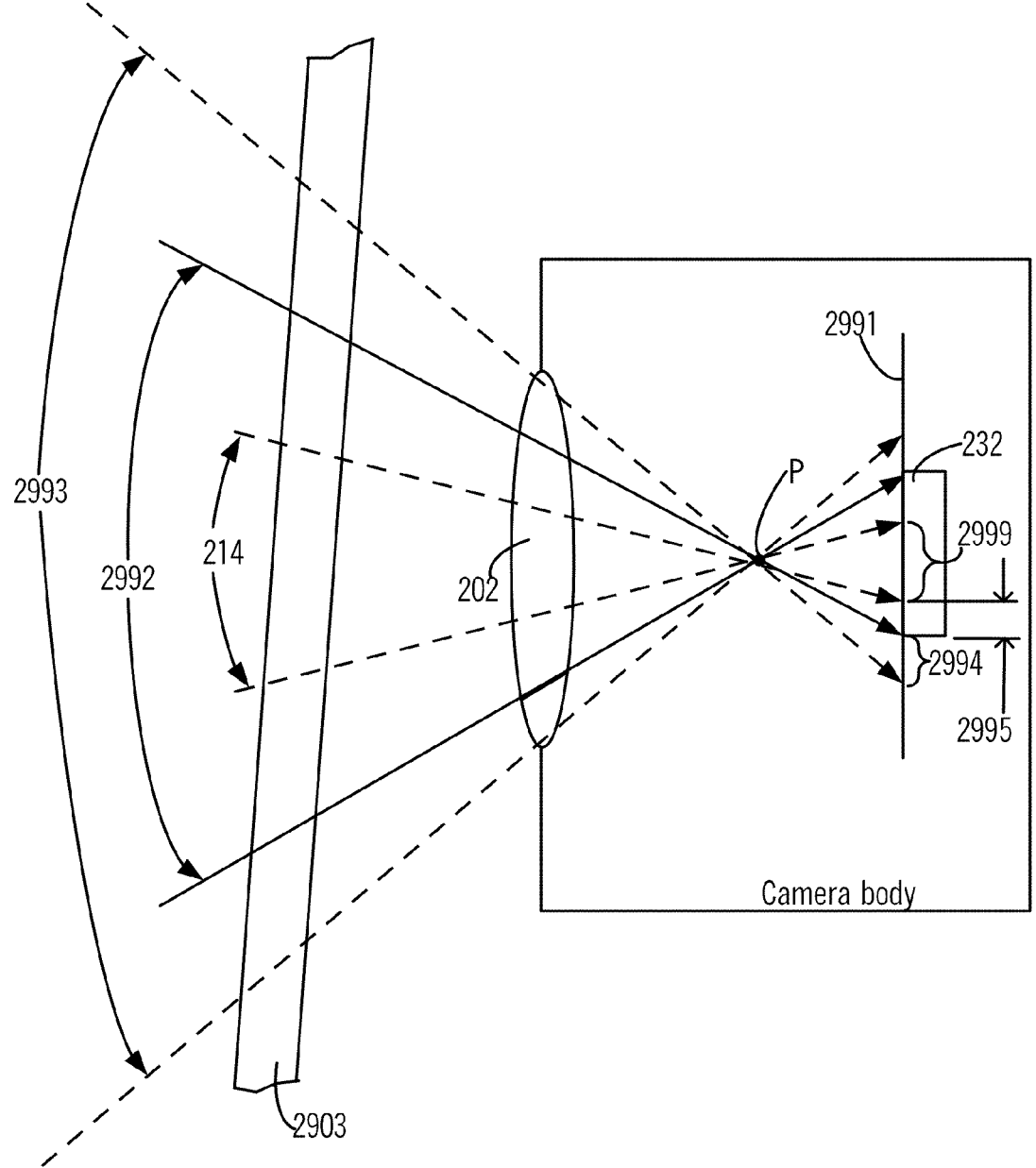

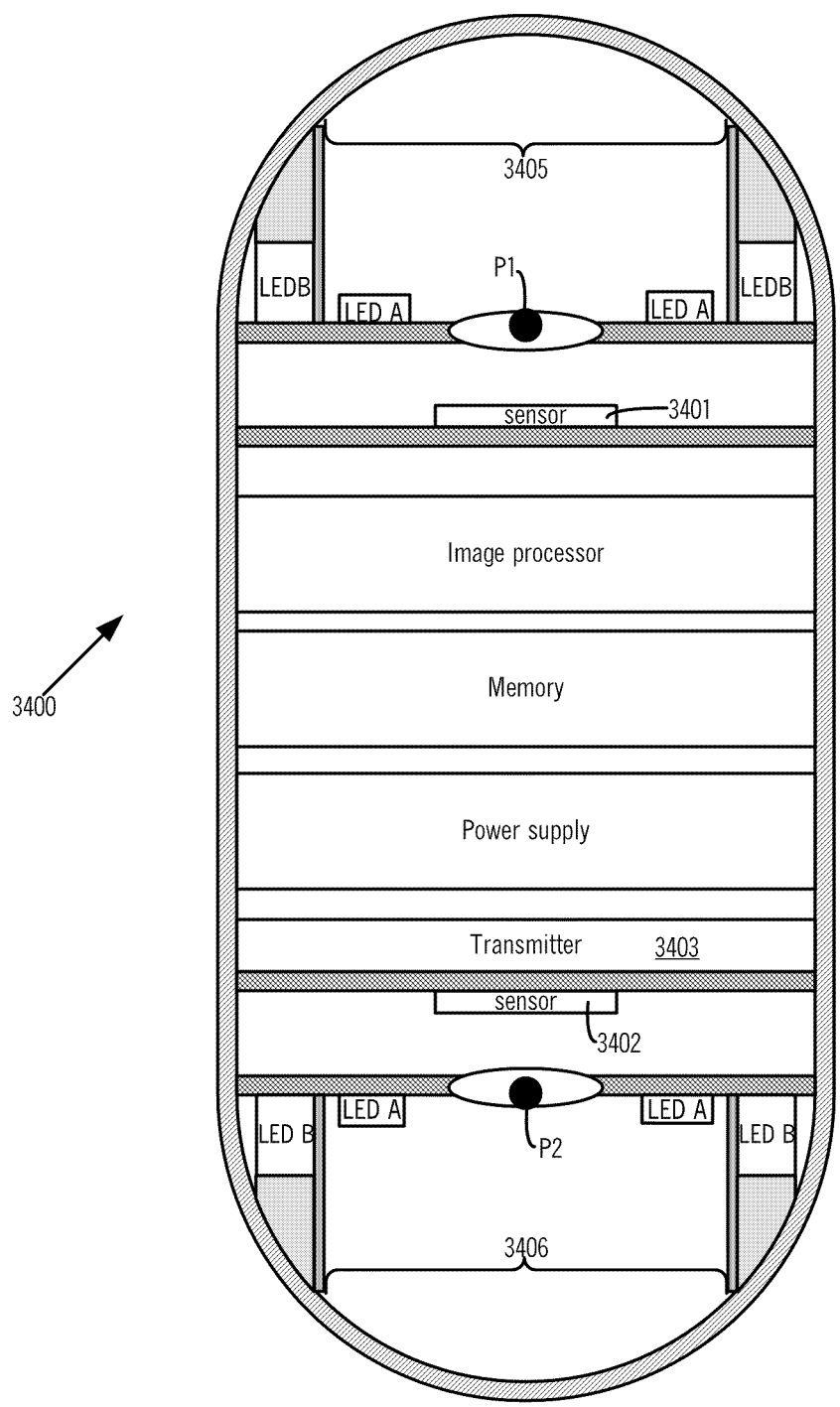

IN VIVO CAMERA WITH MULTIPLE SOURCES TO ILLUMINATE TISSUE AT DIFFERENT DISTANCES

CROSS-REFERENCE TO PROVISIONAL APPLICATION

This application claims priority under 35 USC §119 (e) from a provisional application No. 61/060,068 filed on Jun. 9, 2008 having the title "In Vivo CAMERA WITH MULTIPLE SOURCES TO ILLUMINATE TISSUE AT DIFFERENT DISTANCES", filed by Gordon C. Wilson, which is incorporated by reference herein in its entirety.

BACKGROUND

Various prior art devices have been developed that are configured to capture an image from within in vivo passages and cavities within an organism's body, such as cavities, ducts, and tubular organs within the gastrointestinal (GI) tract. Several prior art devices are formed as a capsule dimensioned small enough to be swallowed. The capsule typically holds a camera and one or more light sources for illuminating an object outside the capsule whose image is recorded by the camera. The electronics in the capsule may be powered by batteries or by inductive power transfer from outside the body. The capsule may also contain memory for storing captured images and/or a radio transmitter for transmitting data to an ex vivo receiver outside the body. A common diagnostic procedure involves a living organism (such as a human or animal) swallowing the capsule, followed by the camera in the capsule capturing images at various intervals as the capsule moves passively through the organism's cavities formed by inside tissue walls of the GI tract under the action of peristalsis.

Two general image-capture scenarios may be envisioned, depending on the size of the organ imaged. In relatively constricted passages, such as the esophagus and the small intestine, a capsule which is oblong and of length less than the diameter of the passage, will naturally align itself longitudinally within the passage. In several prior art capsules, the camera is situated under a transparent dome at one (or both) ends of the capsule. The camera faces down the passage so that the center of the image is formed by a dark hole. The field of interest is the intestinal wall at the periphery of the image.

FIG. 1A illustrates an in vivo camera capsule 100 of the prior art. Capsule 100 includes a housing that can travel in vivo inside an organ 102, such as an esophagus or a small intestine, within an interior cavity 104 of the organ. In the image-capture scenario shown in FIG. 1A, capsule 100 is in contact with an inner surface 106 of the organ, and the camera lens opening 110 captures images within its field of view 128. The capsule 100 may include an output port 114 for outputting image data, a power supply 116 for powering components of the camera, a memory 118 for storing images, compression circuitry 120 for compressing images to be stored in memory, an image processor 122 for processing image data, and LEDs 126 for illuminating surface 106 of the organ so that images can be captured from the light that is scattered off of the surface.

A second scenario occurs when a capsule is in a cavity, such as the colon, whose diameter is larger than any dimension of the capsule. In this scenario the capsule orientation is much less predictable, unless some mechanism stabilizes it. Assuming that the organ is empty of food, feces, and fluids, the primary forces acting on the capsule are gravity, surface tension, friction, and the force of the cavity wall pressing against the capsule. The cavity applies pressure to the capsule, both as a passive reaction to other forces such as gravity pushing the capsule against it and as the periodic active pressure of peristalsis. These forces determine the dynamics of the capsule's movement and its orientation during periods of stasis. The magnitude and direction of each of these forces is influenced by the physical characteristics of the capsule and the cavity. For example, the greater the mass of the capsule, the greater the force of gravity will be, and the smoother the capsule, the less the force of friction. Undulations in the wall of the colon tend to tip the capsule such that a longitudinal axis 118 of the capsule is not parallel to the longitudinal axis of the colon.

FIG. 1B shows an example of a passage 134, such as a human colon, with capsule 100 in contact with surface 132 on the left side of the figure. In this case, an optical axis (not shown) of the camera is parallel to the longitudinal axis of passage 134 (both axes are oriented vertically in the figure). Capsule 100 also has a longitudinal axis 118 that is coincident with its camera's optical axis. A ridge 136 in passage 134 has a front surface 138 which is visible and thus imaged by capsule 100 as it approaches the ridge (assuming capsule 100 moves upwards in the figure). Backside 140 of ridge 136, however, is not visible to the lens opening 110, and hence does not form an image of backside 140. Specifically, capsule 100 misses part of surface 140 and note that it misses an irregularity in passage 134, illustrated as polyp 142.

In FIG. 1B, three points within the field of view of lens opening 110 are labeled A, B and C. The distance of lens opening 110 is different for these three points, where the range of the view 112 is broader on one side of the capsule than the other, so that a large depth of field is required to produce adequate focus for all three simultaneously. Also, if the LED (light emitting diode) illuminators provide uniform flux across the angular FOV, then point A will be more brightly illuminated than points B and C. Thus, an optimal exposure for point B results in over exposure at point A and under exposure at point C. An optimal exposure for point A results in under exposure at points B and C. For each image, only a relatively small percentage of the FOV will have proper focus and exposure, making the system inefficient. Power is expended on every portion of the image by the flash and by the imager, which might be an array of CMOS or CCD pixels. Moreover, without image compression, further system resources are expended to store or transmit portions of images with low information content. In order to maximize the likelihood that all surfaces within the colon are adequately imaged, a significant redundancy, that is, multiple overlapping images, is required in using this prior art capsule.

U.S. Pat. No. 6,836,377 and U.S. Pat. No. 6,918,872 disclose two prior art geometries for non-panoramic capsule cameras. In U.S. Pat. No. 6,836,377, the capsule dome is ellipsoidal with the pupil at its center and LEDs lying on the focal curve. In U.S. Pat. No. 6,918,872, the dome is spherical with the pupil centered on the center of curvature and LEDs in the same plane further toward the edge of the sphere. The just-described two patents are incorporated by reference herein in their entirety, as background. Various illumination geometries for capsule endoscopes with panoramic imaging systems are disclosed in U.S. patent application Ser. No. 11/642,285 filed on Dec. 19, 2006 by Kang-Huai Wang and Gordon Wilson entitled "In Vivo Sensor with Panoramic Camera" and assigned to CapsoVision, Inc. The just-described patent application is incorporated by reference herein in its entirety.

US Patent Publication 2006/0178557 by Mintchev et al. entitled "Self-Stabilizing Encapsulated Imaging System" is incorporated by reference herein in its entirety as background. This publication describes a capsule endoscope illustrated in FIG. 1C attached hereto, wherein a light emitting diode (LED) 154 and an imager 152 (e.g. a CMOS imager) are mounted in a central region of a capsule, between ends 156a and 156b. The capsule includes an RF transmitter 158 that transmits images acquired by imager 152 to an external receiver. The capsule also includes batteries 160a and 160b, and a controller 162.

The inventor believes that improvements in illumination for imaging in vivo passages by endoscopes are desired.

SUMMARY

In accordance with the invention, an endoscope provides illumination inside a body cavity using multiple sources of light, and captures images of tissue in the body cavity using a camera enclosed therein. In certain embodiments of the invention, one of the sources (also called "long-range source") is used to image tissue located in a predetermined distance range from the endoscope. In the just-described embodiments, tissue located in contact with or close to (e.g. within 5 mm of) the endoscope is illuminated by another of the sources (also called "short-range source").

The just-described two light sources may be positioned relative to the camera as described next, based on (1) a point of intersection of an optical axis of the camera with an inner surface of a housing of the endoscope, hereinafter "optical-axis intersection point" or simply "intersection point"; (2) one region (hereinafter "long-range illumination region") of the housing through which light (also called "long-range light") from the long-range source exits the housing; and (3) another region (hereinafter "short-range illumination region") of the housing through which light (also called "short-range light") from the short-range source exits the housing. Specifically, the short-range light source and the long-range light source are positioned such that the optical-axis intersection point is contained within (and is a portion of) the short-range illumination region, but the optical-axis intersection point is located outside the long-range illumination region.

BRIEF DESCRIPTION OF THE FIGURES

FIG. 2A illustrates, in a perspective view, a capsule endoscope 200 in one embodiment of the invention, having a tubular wall 201M with an imaging region 212 overlapping an illumination region 210 through which light is transmitted for short-range illumination and another illumination region 211 through which light is transmitted for long-range illumination.

FIGS. 2B and 2C illustrate, in perspective views, the capsule endoscope of FIG. 2A, when viewed from the left of FIG. 2A, showing overlapping beams of illumination (FIG. 2B) and a coalesced region formed thereby (FIG. 2C).

FIG. 2D illustrates, in a perspective view, an arrangement of light sources within the capsule endoscope of FIG. 2A.

FIG. 2E illustrates, a cross-sectional view of the capsule endoscope 200, taken in the direction 2E-2E in FIG. 2C.

FIG. 2F illustrates, a cross-sectional view of the another capsule endoscope in accordance with the invention.

FIG. 2G illustrates an endoscope in still another embodiment of the invention, wherein the tubular wall has a central region of a diameter larger than the two ends.

FIG. 2H illustrates an endoscope in another embodiment of the invention, wherein the tubular wall has an aspect ratio less than 1.

FIG. 2I illustrates, in a graph, the radiant energy generated by a lower LED 217 and an upper LED 205 illustrated in FIG. 2E, depending on distance of tissue from the endoscope.

FIGS. 2J and 2K illustrate distribution of intensity of light beams and spot sizes, at different distances, in response to current applied to LEDs 217 and 205 to generate radiant energy as illustrated in FIG. 2I.

FIG. 13 illustrates, in a cross-sectional view, relative positions of a light emitter and a compound parabolic concentrator in some embodiments of an endoscope in accordance with the invention.

FIGS. 29A, 29B and 29C illustrate, in partial cross-sectional views, geometry for positioning a light source S relative to a pupil P of a camera to eliminate or minimize capture of virtual sources in an image.

FIG. 34 illustrates an endoscope having two cameras at two ends of a capsule in an alternative embodiment of the invention

DETAILED DESCRIPTION

Figure 1A:
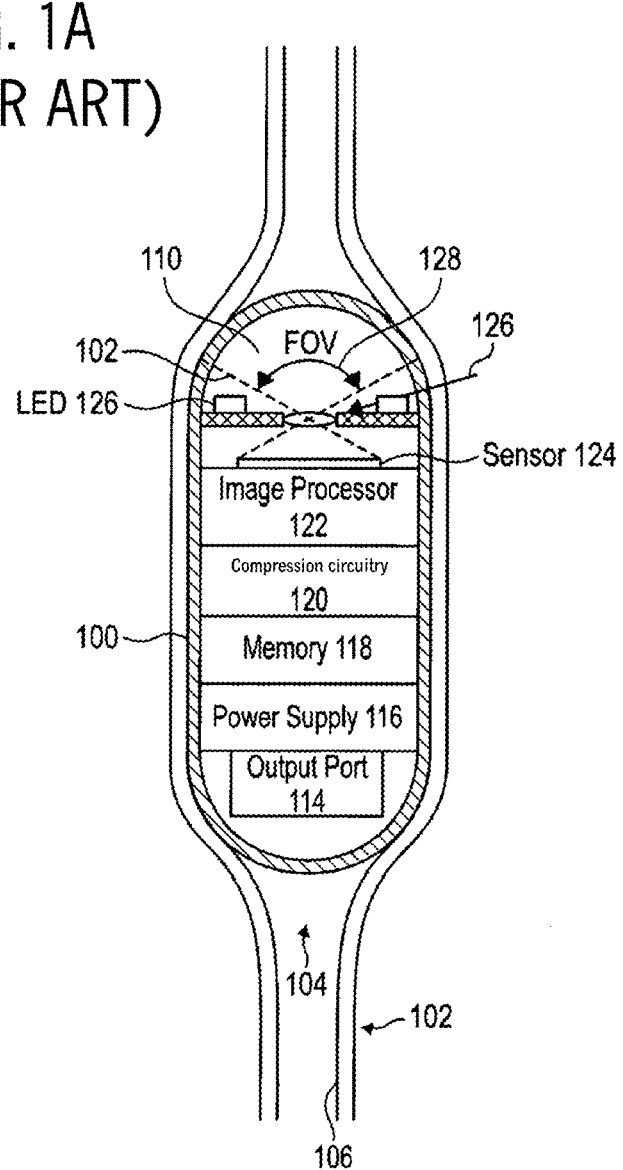
FIGS. 1A and 1B illustrate, in cross-sectional diagrams, a prior art capsule endoscope in a small intestine and a large intestine respectively.
Figure 1B:
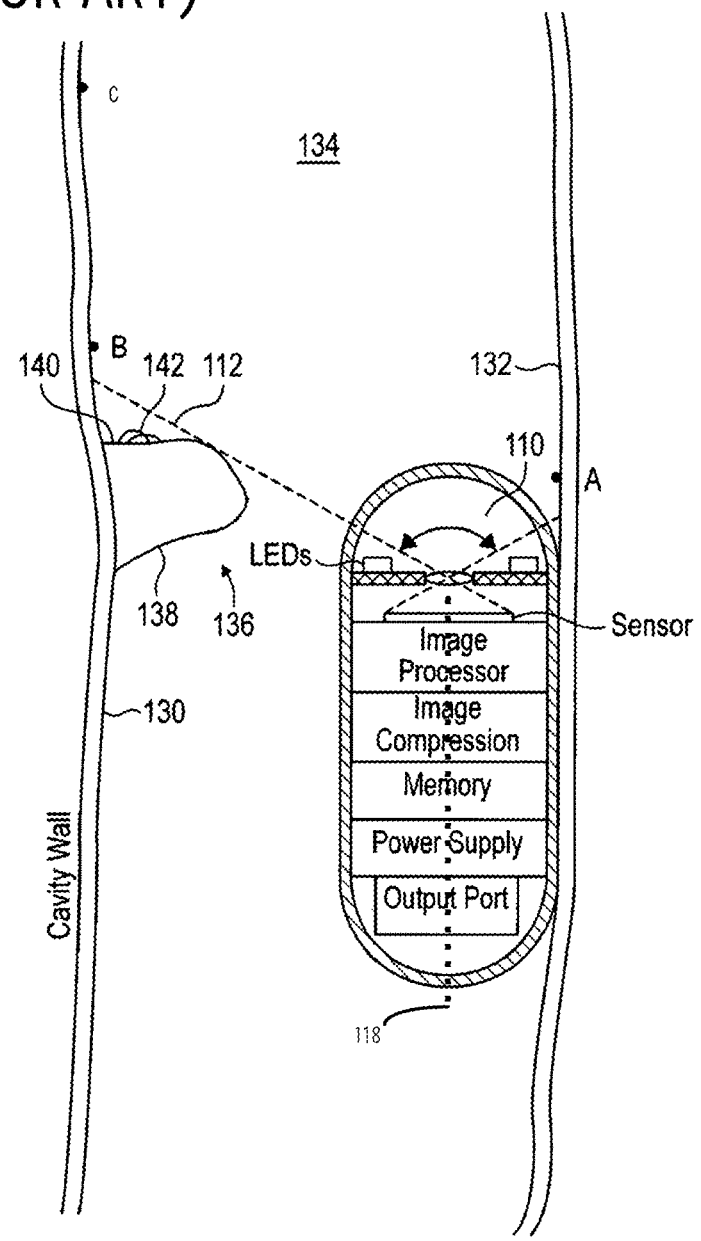
Figure 1C:
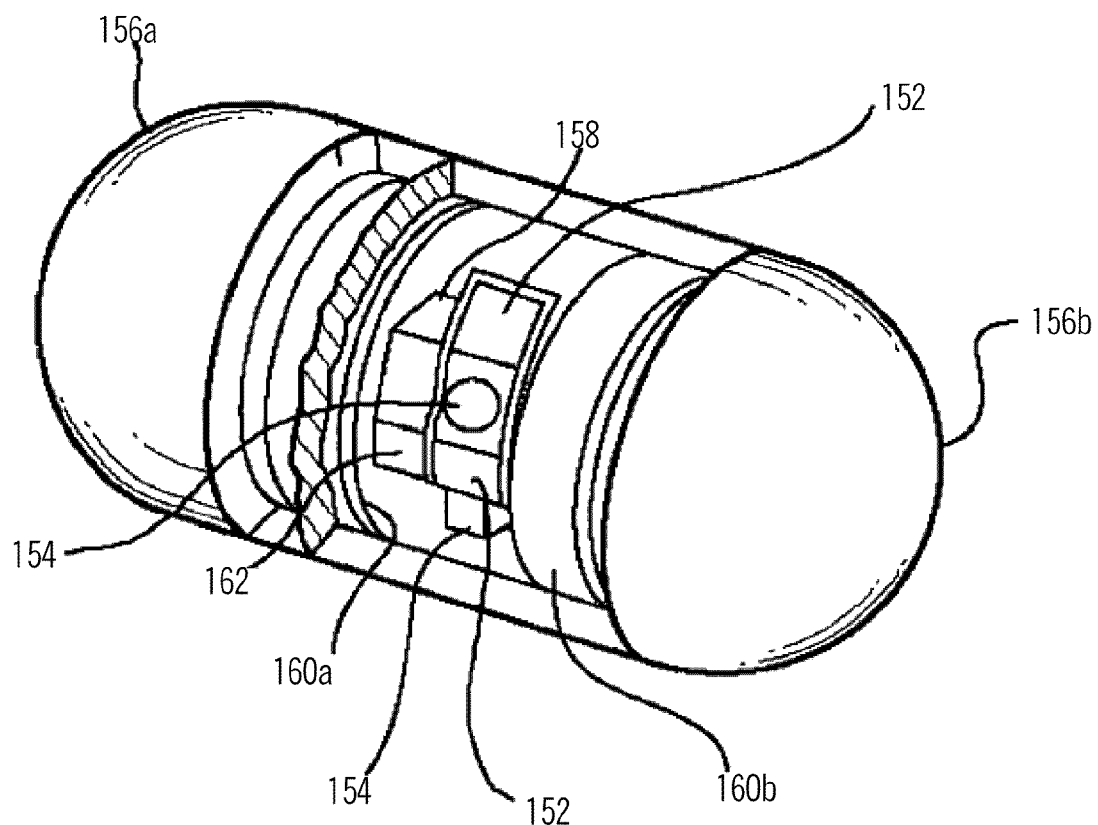
FIG. 1C illustrates, in a perspective cut-away view, a prior art endoscope described in US Patent Publication 2006/0178557 by Mintchev et al.

In accordance with the invention, an endoscope 200 (FIG. 2A) provides illumination inside a body cavity 241 of a diameter D, using multiple light sources 205, 206, and captures images of tissue using a camera enclosed therein. In some embodiments, endoscope 200 has an aspect ratio greater than one, with a longitudinal axis 222. The orientation of endoscope 200 is determined by the dimension and orientation of body cavity 241 that itself is typically elongated. Examples of body cavity 241 are various portions of the gastrointestinal tract, such as the small intestine and the colon (large intestine). Note that in FIG. 2A, a number of lines 299 are used as shading on a smoothly curved surface of housing 201, specifically to convey a visual sense of depth in the perspective view. Similar shading lines are also used in FIGS. 2B-2D, FIGS. 2G-K, and FIGS. 2M-2P.

Referring to FIG. 2A, source 205 of endoscope 200 is a "long-range source" that is used to image tissue located in cavity 241 within a predetermined distance range from the endoscope, e.g. between 10 mm and 35 mm. Long-range source 205 is not used when tissue of the body cavity 241 is in contact with the endoscope. Instead, in-contact tissue is imaged using illumination primarily from a short-range source 206. Tissue which is close to (e.g. within 5 mm of) the endoscope, but not in contact with the endoscope, is illuminated by both sources 205 and 206 in some embodiments of the invention.

Regardless of how implemented, in many embodiments multiple light sources 205 and 206 are positioned relative to a pupil 202 (FIG. 2A) of a camera as described next. Pupil 202 has an optical axis 203 that intersects with an internal surface of housing 201 of endoscope 200 at a point 204. Note that housing 201 in FIG. 2A is illustratively shown to have no thickness, although as will be readily apparent to the skilled artisan the housing has a finite thickness (e.g. 4 mm). Point 204 is also referred to herein as an "optical-axis intersection point" or simply "intersection point". Long-range source 205 is positioned relative to lens 202 such that optical-axis intersection point 204 is located outside of a region (also called "long-range illumination region") 211 through which light (also called "long-range light") 209 transmitted by long-range source 205 exits housing 201. Moreover, short-range source 206 is positioned relative to lens 202 such that optical-axis intersection point 204 is located inside of another region (also called "short-range illumination region") 210 through which light (also called "short-range light") 208 transmitted by short-range source 206 exits housing 201. Note that short-range illumination region 210 is larger than the long-range illumination region 211, by design so as to ensure adequate uniformity in illumination of tissue when the tissue is close to or touching the endoscope.

To summarize the arrangement described in the preceding paragraph, light sources 205 and 206 are positioned such that optical-axis intersection point 204 is contained within (and is a portion of) short-range illumination region 210, but is located outside of long-range illumination region 211. In the embodiment illustrated in FIG. 2A, long-range illumination region 211 not only does not enclose intersection point 204, this region 211 also does not overlap a region (also called "imaging region") 212 of housing 201 through which light (also called "reflected light") reflected by tissue is transmitted through housing 201 and is captured by the camera. In some embodiments, the specific position and orientation of light sources 205 and 206 relative to pupil 202 of the camera is determined empirically, with a goal to improve uniformity in illumination of tissue, located in multiple ranges of distances from the endoscope.

Note that stray reflected light may enter endoscope 200 through other regions, but it is a boundary of region 212 which demarcates the light used in forming a diagnosable image within endoscope 200. The boundary of region 212 excludes any light which is not sensed by a sensor within endoscope 200. Moreover, the boundary of region 212 also excludes any light which may be sensed but is not eventually used in a diagnosable image, e.g. light which generates a portion of an image that is "cropped" (i.e. not used) prior to diagnosis.

Imaging region 212 is typically determined by a field of view ("FOV") 214. Field of view 214 is defined by a range of angles in a plane passing through optical-axis intersection point 204 and optical axis 203 over which tissue 241 located outside housing 201 forms an image captured by the camera for diagnosis. Note that the field of view is sometimes called the angle of coverage or angle of view. The field of view depends on the focal length of an objective lens adjacent to pupil 202, and the physical size of the film or sensor used to record the image. An intersection of field of view 214 with housing 201 forms imaging region 212 of endoscope 200. In endoscope 200, each of light sources 205 and 206 are located outside the field of view 214 so as to avoid imaging light from these sources. The aforementioned FOV refers to the longitudinal direction; an angular field of view exists for the lateral direction as well. However, the lateral FOV is not germane to the present discussion.

Moreover, the above-described lack of overlap between long-range illumination region 211 and imaging region 212 eliminates any possibility that a virtual image (also called "ghost"), due to long-range light 209 reflected by housing 201, is present in an image that is captured by the camera and used for diagnosis. In certain alternative embodiments, a ghost from reflection of long-range light by the housing, is present in an image that is formed in the camera, and a sensor is operated to exclude the ghost e.g. by cropping the image. During cropping, a part of an image in a central region thereof is transmitted by endoscope 200 to a computer for use in diagnosis, and the rest of the image containing the ghost is not processed. Depending on the embodiment, cropping is performed either by a computer located outside the body, in which case the entire image is transmitted, or alternatively performed within housing 201. In the just-described alternative embodiments, cropping is performed in electronic circuitry, e.g. by a sensor and/or by a processor (see FIG. 18).

In some embodiments of the type described above, light source 206 is deliberately positioned so that short-range illumination region 210 overlaps imaging region 212. The just-described overlap is chosen to ensure that short-range light 208 illuminates tissue adequately enough to obtain a diagnosable image in the camera, even when the tissue is in contact with an external surface of housing 201.

In embodiments of the type shown in FIG. 2A, regions 210, 211 and 212 are oriented transversely e.g. on a tubular wall 201M (FIG. 2B) which is a portion of housing 201. Moreover, in FIG. 2A, tubular wall 201M forms a portion of a housing 201 that is shaped as a capsule with two domes 201T and 201B located on each of the two sides of wall 201M. In the embodiment shown in FIG. 2A, tubular wall 201M is capped with a dome-shaped end (or simply "dome") 201T on one side and another dome-shaped end 201B on the other side, to implement a capsule endoscope. Domes 201T and 201B constitute portions of a housing that also includes tubular wall 201M.

Figure 19:
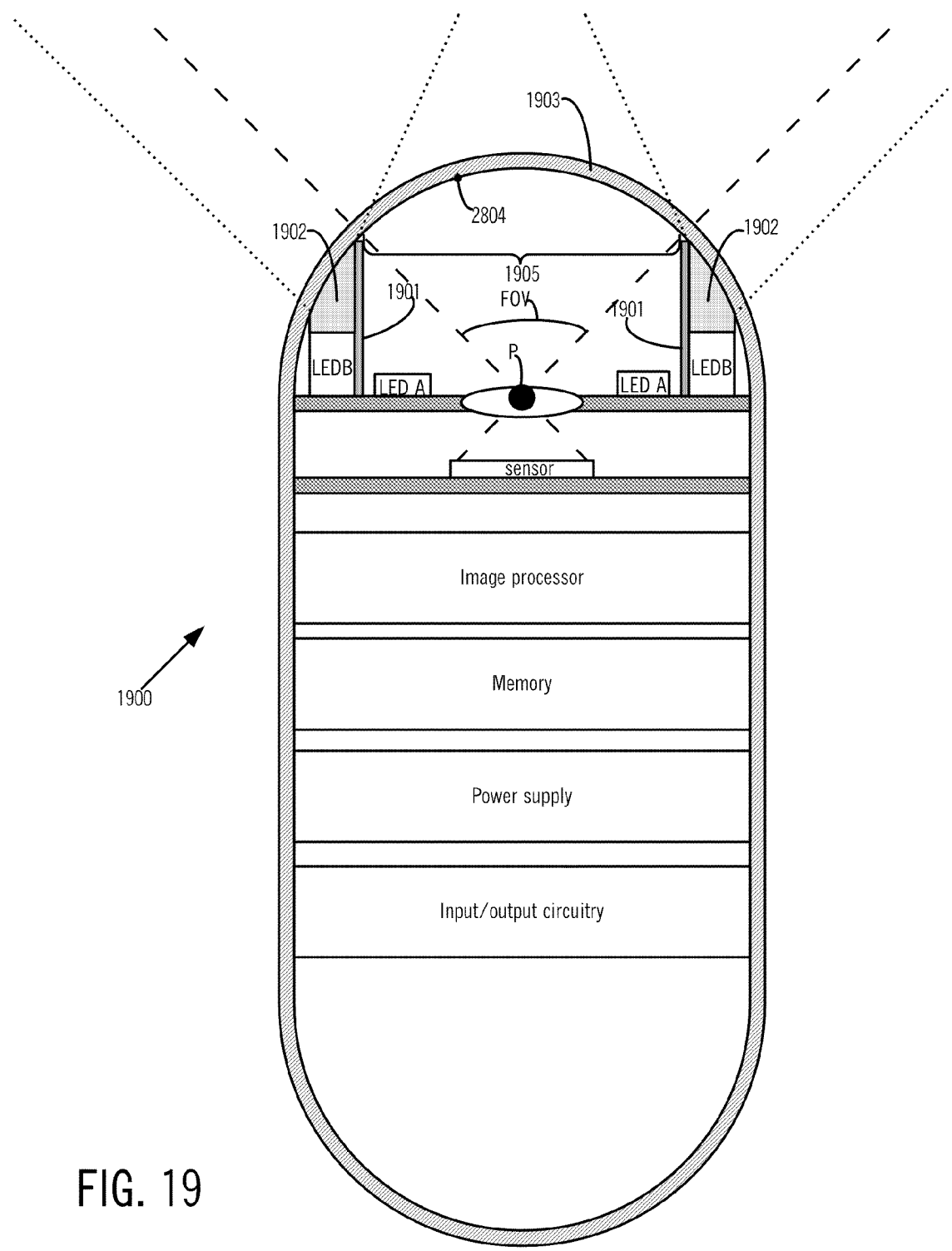
FIG. 19 illustrates use of an endoscope having two light emitters, for axial illumination and imaging, in an alternative embodiment of the invention.

In endoscope 200 (FIG. 2A) domes 201T and 201B are not used to pass any light to a region outside of endoscope 200. Domes 201T and 201B are also not used to receive any light that forms an image to be diagnosed. Instead, light exits endoscope 200 and enters endoscope 200 through tubular wall 201M, and the just-described orientation of light relative to the endoscope is referred to herein as "radial". Domes 201T and 201B are used (with tubular wall 201M) to form a water-tight housing for optical and electronic components enclosed within endoscope 200. Note that other embodiments of an endoscope in accordance with the invention may have different shapes, e.g. endoscope 290 illustrated in FIGS. 2Q and 2R has a distal tip 291 at an end of insertion tube 292. Distal tip 291 also illuminates a body cavity radially, through a tubular wall similar to endoscope 200. Note that in alternative embodiments, regions 210, 211 and 212 are oriented axially e.g. on dome 201T or dome 201B as illustrated in FIG. 19.

Figure 2J:
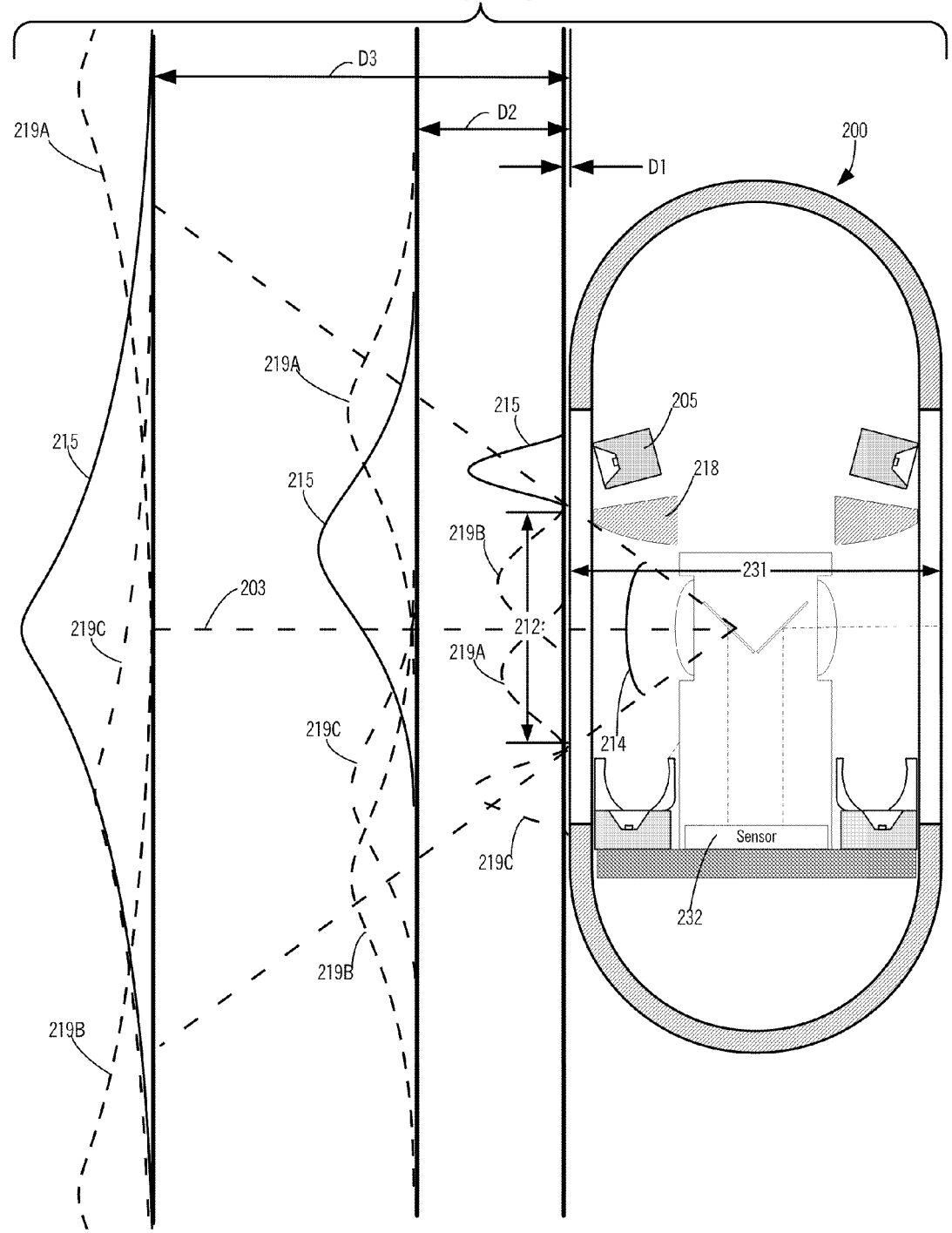
Figure 2L:
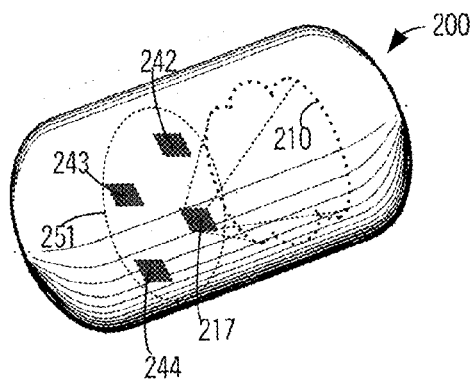
FIGS. 2L and 2M illustrate the endoscope of FIG. 2A with multiple short-range sources enclosed in the housing, positioned at a common latitude relative to the optical axis but located at different longitudes (i.e. radial directions).
Figure 2M:
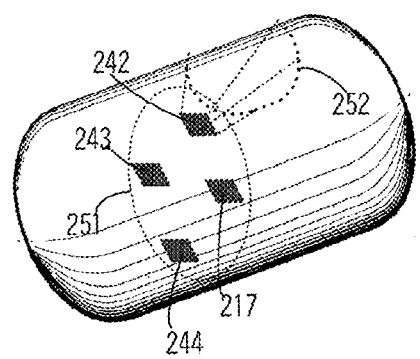
Figure 2N:
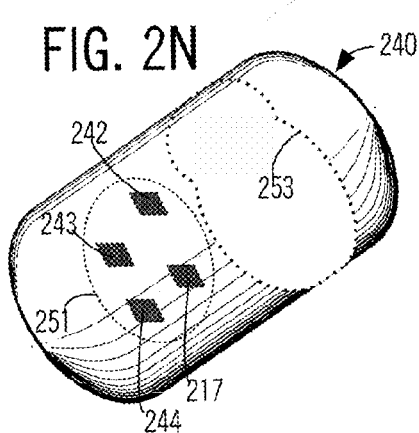
FIG. 2N illustrates use of the endoscope of FIGS. 2L and 2M in normal operation, wherein the multiple short-range sources create successively overlapping regions spanning 3600.
Figure 2O:
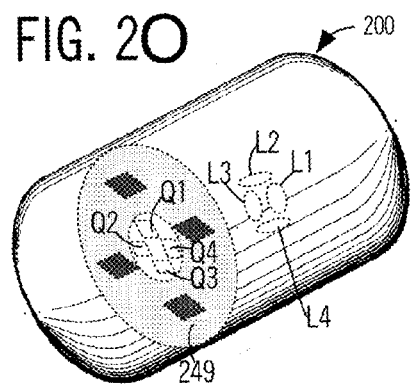
FIG. 2O illustrates lenses L1-L4 and sensors Q1-Q4 that are also enclosed in an endoscope of the type illustrated in FIGS. 2L, 2M and 2N.
Figure 2P:
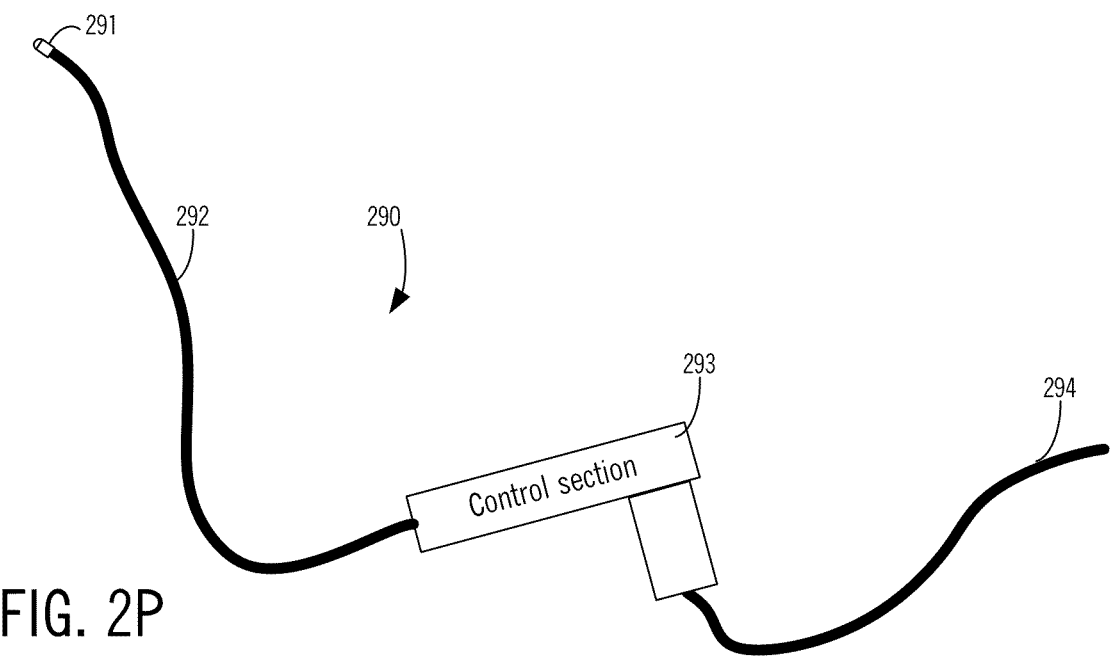
FIG. 2P illustrates an endoscope that includes a distal tip of the type illustrated in FIG. 2A, mounted at an end of an insertion tube in accordance with the invention.
Figure 2Q:
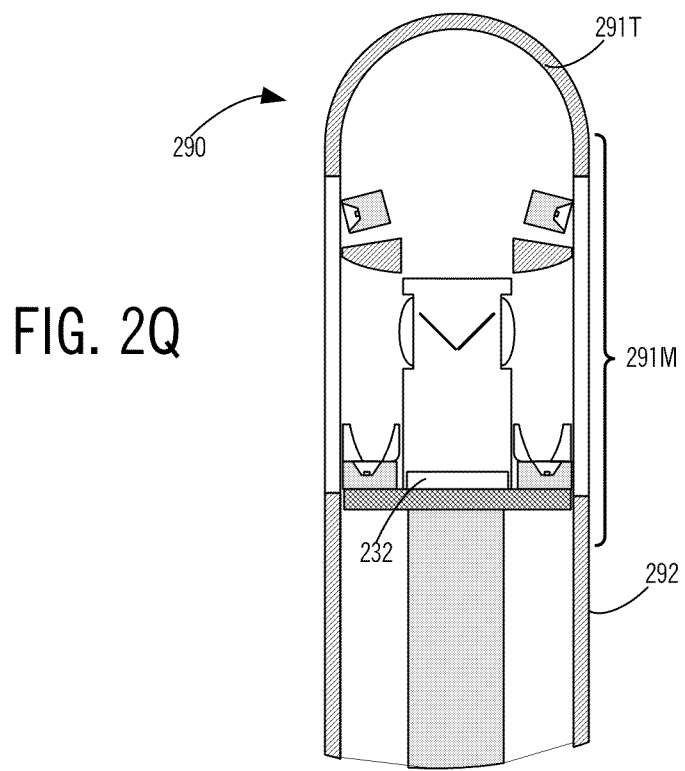
FIG. 2Q illustrates, in an enlarged cross-sectional view, the distal tip of FIG. 2P.

As discussed above, a radially-illuminating endoscope (regardless of whether shaped as a capsule as in FIG. 2A or as a distal tip 291 at the end of an insertion tube 292 as shown in FIGS. 2Q and 2R) provides illumination through tubular wall 201M. Tubular wall 201M may have a circular cross section, such as a cylinder or a frustum of a prolate or oblate spheroid. The endoscope's tubular wall 201M can alternatively have a non-circular cross section, such as an elliptical cross-section. Regardless of the cross-section, a majority of light (e.g. greater than 50% of the energy) exits from endoscope 200 radially, side-ways through tubular wall 201M (FIG. 2B) of the endoscope. Moreover, tissue-reflected light passes back through tubular wall 220 also laterally, to form within endoscope 200 an image to be diagnosed (not shown in FIG. 2B).

In several embodiments, short-range light 208 exiting an endoscope is initially generated by a light emitter (such as an LED) within the housing, and short-range light 208 is then split by an optical element (also within the housing) into at least two fractions that respectively form at least two overlapping spots on the housing. For example, FIG. 2B illustrates two spots 210A and 210B formed by two fractions of short-range light 208 resulting from splitting. Splitting of short-range light 208 into two or more fractions enables a larger area of tissue to be illuminated by overlapping spots which provide greater uniformity in energy distribution across the illumination region, relative to a single spot which has a single peak in its center.

In the example shown in FIG. 2B, the two spots 210A and 210B overlap one another on housing 201, to form at least a majority of (i.e. greater than 50% of area of) short-range illumination region 210 as illustrated in FIG. 2C. In FIGS. 2B and 2C, a third spot 210C is also formed, by a third fraction of short-range light 208 and included in short-range illumination region 210. In one illustrative embodiment, two roughly equal fractions (approximately 25% of energy) of short-range light 208 form spots 210A and 210B. In the illustrative embodiment, another fraction (approximately 50% of energy) of short-range light 208 forms a third spot 210C.

As will be readily apparent to the skilled artisan, the examples of percentages that form the various fractions of short-range light 208 are different in different embodiments. Moreover, other embodiments (not shown) split short-range light 208 into only two fractions, i.e. do not form a third spot 210C. Still other embodiments (also not shown) split short-range light 208 into four or more fractions, i.e. form four or more spots of short-range illumination region 210. Moreover, also depending on the embodiment, the spots of short-range light 208 may or may not coalesce together, to form a single continuous region.

In endoscope 200, the long-range illumination region 211 and the short-range illumination region 210 may or may not overlap one another, depending on the embodiment. Also depending on the embodiment, imaging region 212 may or may not overlap the long-range illumination region 211.

In many embodiments, two spots 210A and 210B are formed by two beams 208A and 208B (FIG. 2D) that are two fractions of short-range light 208 (FIG. 2A). Beams 208A and 208B are transmitted towards the interior surface of housing 201 by two light sources 206 and 218 respectively that are located on opposite sides of optical axis 203. Optical axis 203 is shown in FIGS. 2A and 2D as a horizontal line and for convenience, the two sides of optical axis 203 are referred to herein as "above" and "below" the axis, although it is to be understood that the two sides orient differently depending on the orientation of axis 203 relative to the observer (e.g. "left" and "right" if axis 203 is oriented vertically).

Referring to FIG. 2D, light source 206 is located below optical axis 203 and transmits a majority of (i.e. greater than 50% of energy in) beam 208A below optical axis 203. Accordingly, optical-axis intersection point 204 is located in a top portion of spot 210A. In some embodiments, a light emitter is located below optical axis 203, and this light emitter is included in light source 206 which additionally includes an optical element that splits short-range light 208 received from the light emitter. Light source 206 is located below optical axis 203 and located sufficiently close to (e.g. in contact with) housing 201 such that the angles of incidence of beam 208A on housing 201 are sufficiently large, within region 212, to minimize or eliminate capture by the camera of any portion of beam 208A directly reflected by housing 201.

The above-described optical element in some embodiments forms beam 208B from light 208 received from the light emitter in addition to the above-described beam 208A. Beam 208B is initially transmitted by the optical element across optical axis 203 to light source 218. As shown in FIG. 2D, light source 218 is located above optical axis 203, and includes a reflective surface that re-transmits a majority of beam 208B received from the light emitter to form spot 210B on an inner surface of the housing. Optical-axis intersection point 204 is located in a bottom portion of spot 210B. Note that in the embodiment illustrated in FIGS. 2B-2D, bottom portion of spot 210B overlaps the top portion of spot 210A and intersection point 204 is located within the overlap. Moreover, in the embodiment illustrated in FIG. 2B, spots 210A and 210B are aligned relative to one another, along a direction that is aligned with longitudinal axis 222 (e.g. within 50°). Note that here as well, light source 218 is located sufficiently close to housing 201 such that the angles of incidence of beam 208B are sufficiently large to minimize or eliminate capture by the camera of any portion of beam 208B directly reflected by housing 201.

In the illustrative embodiment shown in FIG. 2D, a third beam 208C is also formed by the optical element in splitting short-range light 208, and beam 208C is directly incident on housing 201 to form spot 210C a majority of which is located below spot 210B (with a small overlap therebetween). Note that spot 210C is located in illumination region 210 outside of imaging region 212. Accordingly, a majority of the third fraction which is incident on spot 210C does not reach the camera when the tissue is in contact with the housing. However, beam 208C provides illumination through short-range illumination region 210 that does reach the camera when tissue is located a short distance away from the housing (e.g. 5 mm away).

FIG. 2E illustrates an exemplary implementation of one embodiment of an endoscope 200 of the type described above in reference to FIGS. 2A-2D. Specifically, as illustrated in FIG. 2E, a light emitter 217 supplies short-range light to an optical element 216 that splits the short-range light into three beams as follows. One beam 208C (FIG. 2D) is directly incident on the housing with intensity distribution 219C (FIG. 2E). Another beam 208A (FIG. 2D) is mostly below optical axis 203 and is incident on the housing with intensity distribution 219A (FIG. 2E). A third beam 208B (FIG. 2D) crosses optical axis 203 and is reflected by a mirror 218 and then is incident on the housing with intensity distribution 219B (FIG. 2E). An example of optical element 216 is a compound parabolic concentrator (CPC) as discussed below. Lens L is an objective for the camera, and light received therethrough is reflected by a mirror M to sensor 232 for sensing and storage of the image.

Note that the implementation illustrated in FIG. 2E is symmetric about longitudinal axis 222, and endoscope 200 holds four copies of a light emitter in long-range source 205, another light emitter 217 and optical element 216 (together forming a short range light source), optical element 218 (which together with light emitter 217 and optical element 216 forms another short range light source), lens L and mirror M. Note also that sensor 232 and light emitter 217 are both supported by a board 249. In another embodiment, there are a pair of light emitters in each of eight radial directions (for a total of sixteen emitters) that are used to generate a 360° panoramic image of a body cavity.

Although an endoscope 200 illustrated in FIG. 2E, has two light emitters in a given radial direction, alternative embodiments may use four light emitters in a single radial direction, as shown in the cross-sectional view illustrated in FIG. 2F. In FIG. 2F, endoscope 250 includes two light emitters 221A and 224A that are used as two long-range light sources. Moreover, endoscope 250 also has two additional light emitters 222A and 223A that are used as short-range light sources. Moreover, in some embodiments, light emitters are positioned in the endoscope to illuminate along each of four radial directions (e.g. north, south, east and west around a circular boundary of the housing, when viewed from the top). Three sets of light sources in corresponding three radial directions are illustrated in FIG. 2F as sources 221A, 222A, 223A and 224A in the west direction, sources 221B, 222B, 223B and 224B in the north direction, and sources 221C, 222C, 223C and 224C in the east direction (with sources in the south direction being not shown in FIG. 2F because it is a cross-sectional view). In certain embodiments, light emitters are positioned in the endoscope to illuminate along each of eight radial directions (e.g. north, north-east, east, south-east, south, south-west, west, and north-west, again, when viewed from the top).

The embodiment shown in FIG. 2A has an aspect ratio greater than 1, whereby endoscope 200 has a larger dimension along axis 222 than any other dimension located within a cross-section that is transverse to axis 222. For example, endoscope 200 has a length along tubular wall 201M that is larger than the outer diameter of tubular wall 210M (in case of a circular cross-section). Accordingly, tubular wall 202 has a cylindrical shape, in the just-described embodiment.

In several alternative embodiments of the invention, an endoscope has a tubular wall of varying cross-section along the length of the endoscope. For example, FIG. 2G illustrates an endoscope 223 wherein a tubular wall 224 has an outer diameter 225 (in case of a circular cross-section) in the middle which is larger than an outer diameter 226 at the ends, i.e. tubular wall 224 has a bulge at its center. In another example (not shown), the tubular wall of an endoscope in accordance with the invention has narrower central portion with wide ends, i.e. an hourglass shape. Regardless of the shape of the tubular wall, illumination and imaging are performed through various overlapping and non-overlapping regions of the tubular wall, as described above in certain embodiments of the invention.

Furthermore, in another alternative embodiment illustrated in FIG. 2H, an endoscope 227 has an aspect ratio less than 1, whereby a dimension along axis 222 is smaller than at least one dimension in a cross-section transverse to axis 222, e.g. thickness 229 is smaller than diameter 228 (in case of a circular cross-section). Even though aspect ratio less than 1, in this embodiment as well, overlapping and non-overlapping regions for illumination and imaging are formed on the tubular wall 229 as described above.

In one illustrative embodiment, endoscope 200 (FIG. 2B) has a diameter 231 of 1.1 cm and a length 232 of 2.6 cm. Note that in this illustrative embodiment, tubular wall 201M has a transparent window of height 5.0 mm. Moreover, imaging region 212 (FIG. 2A) has a width expressed as an arc length, of 0.9 cm and a height of 0.5 cm. Furthermore, illumination region 210 (FIG. 2C) does not have an exact boundary. Hence, the contour shown in FIG. 2C is for a specific intensity level, such as 10% of maximum intensity. In the illustrative embodiment, contour 210 has a height of 0.7 cm and a maximum arc width of 0.7 cm. Additionally, note that tubular wall 201M (FIG. 2B) has a length of 2.0 cm. Also, each of domes 201T and 201B has a height of 0.3 cm (see FIG. 2C) and a diameter of 1.1 cm (which diameter is same as the diameter of tubular wall). Note that the dimensions identified herein are merely for illustration, and other dimensions are used in other embodiments.

In some embodiments, imaging region 212 (FIG. 2A) and illumination regions 210 and 211 are located closer to top dome 201T (also called "near end"), and farther removed from bottom dome 201B (also called "far end"). Space adjacent within the endoscope which is enclosed within or adjacent to either or both of domes 201T and 201B is used in certain embodiments to house various electronic components, such as a battery and a wireless transmitter (not shown) of the type normally used in a capsule endoscope.

In other embodiments, illumination and imaging regions 210 and 212 overlap a half-way line (e.g. an "equator") that is located equidistant from each of two farthest points on two domes 201T and 201B of a capsule endoscope. In still other embodiments (also not shown), illumination and imaging regions 210 and 212 are centered at the half-way line and in these embodiments the half-way line passes through optical-axis intersection point 204 (FIG. 2A; half-way line not shown). In some embodiments imaging region 212 and illumination region 210 (as shown in FIG. 2A) have their respective centers offset from one another, although in other embodiments the two centers are coincident.

Referring to FIG. 2A, illumination region 210 is formed by light originating at short-range light source 206 that is located towards the far end 201B. Short-range source 206 is offset in a longitudinal direction along axis 222 from optical axis 203 by a distance 233. Long-range light source 205 is also offset from optical axis 203 in the longitudinal direction along axis 222 similar to light source 206, but the direction is opposite. In FIG. 2A, light source 205 is located towards near end 201T at an offset distance 234 from optical axis 203. Furthermore, as shown in FIG. 2B, light source 218 is implemented by a mirror that is also offset in the longitudinal direction along axis 222 towards near end 201T, at an offset distance 235 from optical axis 203.

Sources 206, 205 and 218 are positioned at locations and oriented at angles that are selected to ensure that any reflection of light from these sources by tubular wall 201M does not enter pupil 202. In one illustrative embodiment, short-range offset distance 233 is 0.2 cm, long-range offset distance 234 is 0.4 cm, and the mirror's offset distance 235 is 0.4 cm. Note that offset distances can be smaller if the angular distribution of light from the source is narrowed. Accordingly, a projection onto a longitudinal plane, of mirror-reflected rays, is in a narrow range of angles relative to rays from the other two sources, and for this reason the mirror's offset distance is also smaller relative to the other two sources' offset distances.

Figure 23:
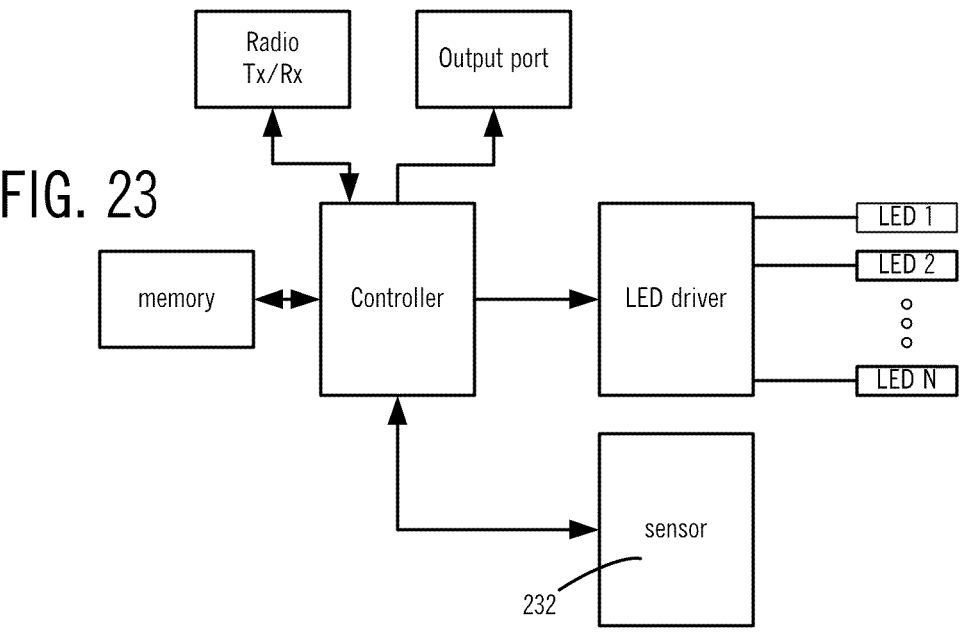
FIG. 23 illustrates, in a block diagram, electronic circuitry including controller, LEDs and sensors in an endoscope in accordance with the invention.

In some embodiments, light sources 205 and 206 are operated to generate different amounts of radiant energy relative to each other depending on distance of tissue 241 from endoscope 200. The distance of tissue is determined by a controller (mounted on a printed circuit board 249) in endoscope 200 based on intensity of light reflected by the tissue and sensed by a sensor 232 of the camera. Using the sensed intensity, current applied to sources 205 and 206 are automatically changed by the controller (see FIG. 23), using an empirically-determined relationship between radiant energy and distance. In the example illustrated in FIG. 2E, the intensity distribution of light from source 205 is not shown.

Source 205 may be operated to generate a minimal amount of radiant energy (or even switched off depending on the embodiment) if the tissue to be imaged is in contact with the endoscope 200. As noted above, in-contact tissue is illuminated by light from short-range source 206. When tissue is far away from the endoscope, multiple light sources 205, 206 and 218 may all be used simultaneously, concurrently or contemporaneously (depending on the embodiment) to provide the illumination needed to generate a diagnosable image. Accordingly, the number of sources used for imaging is varied depending on distance, to ensure that the tissue's image is formed within the camera within a predetermined intensity range.

In some embodiments, the predetermined intensity range is selected ahead of time empirically, based on adequacy of images to enable resolution of the detail necessary for diagnosis by a doctor. The specific manner in which tissue's distance and/or light emitter energy emission are determined for an endoscope is different in various embodiments. Accordingly, numerous methods to determine tissue's distance and/or light emitter energy emission will be readily apparent to the skilled artisan, in view of this disclosure.

Inclusion of multiple light sources in an endoscope in accordance with the invention enables the endoscope to image tissue located at different distances from the endoscope by using illumination of different amounts and/or distributions depending on the distance of the tissue. In a first example, when tissue is located in contact with or at a very short distance D1 from an external surface of the endoscope (e.g. less than a $1/10^{th}$ the diameter D of the body cavity of interest), tissue 241 is illuminated (and imaged) by supplying LED 217 with current to generate radiant energy E2 (FIG. 2I). The resulting illumination includes intensity distributions 219A-219C (FIG. 2J and FIG. 2K) generated by respective beams 208A-208C via imaging region 212. At this time, long-range source LED 205 is operated to generate a negligible amount of energy E1 which results in a distribution 215, and a majority of its energy is outside of field of view 214, i.e. not used in imaging. Hence source 205 may be turned off at this stage, if appropriate.

In a second example, tissue is located at an intermediate distance D2 from the endoscope (e.g. on the order of $\frac{1}{5}^{th}$ of body cavity diameter) and as illustrated in FIG. 2I both LEDs 217 and 205 in endoscope 200 are driven to generate the same amount of radiant energy E3. The resulting illumination now includes intensity distribution 215 (FIG. 2J and FIG. 2K), a portion of which now overlaps optical axis 203, although a majority of energy is above axis 203. Note that the peak of (and hence the center of) distribution 219B also has moved (in the longitudinal direction) to a location above the peak of distribution 215. Furthermore, a peak of distribution 219A has moved from a location above axis 203 to a location below the peak 219C. Accordingly, within the camera's field of view 214 at intermediate distance D2, long-range source LED 205 provides approximately the same amount of illumination as the illumination provided by short-range source LED 217.

In a third example, tissue is located at another intermediate distance D3 (e.g. on the order of $\frac{1}{3}^{rd}$ of body cavity diameter) and long-range source LED 205 is operated to generate energy E5 (FIG. 2I) that is almost double the energy E4 of short-range source LED 217. The intensity distribution 215 (FIG. 2J and FIG. 2K) at distance D3 constitutes a majority of illumination (e.g. provides >50% of energy). Hence, long-range source LED 205 provides a majority of illumination. Note that at distance D3, the peaks of distributions 219A and 219B are located outside of the camera's field of view 214. While the peak of distribution 219C is within the field of view 214, this distribution's contribution to the total illumination is small (e.g. less than 20%).

Finally, in a fourth example, tissue is located at a large distance D4 (e.g. on the order of ½ of body cavity diameter), long-range source LED 205 is supplied power P6 (FIG. 2I) that is an order of magnitude greater than power P4 of short-range source LED 217 (whose power P4 remains same as at distance D3). As shown in FIG. 2K, intensity distribution 215 from long-range source LED 205 provides the primary illumination. Contributions from short-range source LED 217 are minimal at distance D4 (e.g. 5% or less).

Note that in some embodiments of the type shown in FIG. 2I, the integration time of each pixel is shifted relative to another pixel, although the pixels have a common integration time during which time each of the LEDs within the endoscope is turned on, e.g. sequentially one after another, or all on simultaneously. Note further that the amount of radiant energy emitted by an LED (and consequently captured by a pixel) depends on the duration of time for which the LED is turned on and the power output by the LED during the time it is on. A summary of distances and radiant energy discussed above is provided in the following table, for one specific illustrative embodiment, with numbers in the following table being examples which have different values in other embodiments. In the following table, ρ is the distance from the longitudinal axis of endoscope to a plane in which tissue is located, R is the radius of the endoscope, Utop is proportional to the luminous energy of the top long-range LED, and Ubottom is proportional to the luminous energy of the short-range source LED 217

|    | ρ/R | Utop  | Ubottom |
|----|-----|-------|---------|
| D1 | 1.0 | 0.004 | 0.02    |
| D2 | 1.8 | 0.03  | 0.03    |
| D3 | 3.2 | 0.1   | 0.05    |
| D4 | 7.0 | 1.0   | 0.05    |

The intensity distributions shown in FIGS. 2J and 2K are based on annular mirror 218 having a convex reflective surface. The intensity distributions are roughly the same for a flat mirror 218, although the exact distribution shape becomes a bit narrower. Note that the peak in distribution 215 from light transmitted by long-range LED 205 roughly follows a line inclined at an angle of the LED (e.g. 20 degrees relative to optical axis 203). So, if the tilt of LED 205 changes, the horizontal distance at which the center of distribution 215 intersects the optical axis 203 also changes. This distance is given by (distance of LED from axis)/tan (inclination angle). In the absence of significant illumination from the short-range LED, this is the distance at which the long-range illumination's intensity distribution is symmetrical relative to the camera. For greater distances the distribution is less symmetrical but uniformity actually improves because the distribution spreads faster than the field of view expands.

As noted above, FIG. 2A illustrates radial illumination by endoscope 200 in one direction (namely towards the west or left in FIG. 2A) although endoscope 200 has similar structure in other radial directions (e.g. 3 additional directions), to enable generation of a 360° panoramic image of tissue 241 all around within a body cavity of diameter D (FIG. 2A). Specifically, as illustrated in FIG. 2L, endoscope 200 includes, in addition to a short-range light source LED 217, three additional short-range light source LEDs 242, 243 and 244 that are mounted within a common lateral plane 251 in which LED 217 is mounted. While LED 217 forms illumination region 210, other sources form other illumination regions around the tubular wall of endoscope 200. Specifically, as illustrated in FIG. 2M, source 242 forms illumination region 252 that is at a different longitude from region 210. Note that regions 252 and 210 are adjacent to one another and have an overlap such that when both sources 217 and 242 are simultaneously turned on these two regions merge to form a continuous region 253 as shown in FIG. 2N.

Note that endoscope 240 also includes various optical and/or electronic components required to form images that may be combined by a computer (not shown) to form a continuous 360° panoramic image. For example, some embodiments use as the objective a wide-angle lens that has an extremely wide field of view (e.g. 160°). One or more additional optical elements, such as a mirror, a lens and/or a prism are included in an optical path within endoscope 200 from the lens, e.g. to create an appropriate image for capture by a sensor. Note that in some embodiments, the additional optical elements include a mirror followed by three lenses that are selected to ensure low aberration and distortion and to provide an appropriate field of view as will be apparent to the skilled artisan in view of this disclosure. Certain illustrative embodiments, include additional optical elements as described in U.S. application Ser. No. 12/463,488 entitled "Folded Imager" filed by Gordon Wilson et al on May 11, 2009 which is incorporated by reference herein in its entirety.

Endoscope 200 may enclose several lenses (e.g. 4 lenses) used as objectives in each of several longitudinal planes, and light from the objectives passes to corresponding sensors via additional optical elements (as necessary). FIG. 2O illustrates lenses L1-L4 that are used as objectives for reflected light that enters the endoscope. Light from lenses L1-L4 is reflected by mirrors (not shown in FIG. 2O; see mirror M in FIG. 2E), and passes through additional lenses to sensors Q1-Q4 for imaging therein.

Although a capsule shaped endoscope has been illustrated in FIGS. 2A-2F, in an alternative embodiment illustrated in FIG. 2P, an endoscope 290 includes a distal tip 291 at an end of an insertion tube 292. Tube 292 is connected to a control section 293 that in turn is connected to a universal cord 294. As shown in FIG. 2Q, distal tip 291 includes a tubular wall 291M and a top dome 291T at its near end but does not have another dome at the bottom. Instead, the bottom of distal tip 291 is connected to the insertion tube 292. Note that distal tip 291 illuminates a body cavity radially, through tubular wall 291M.

Figure 3:
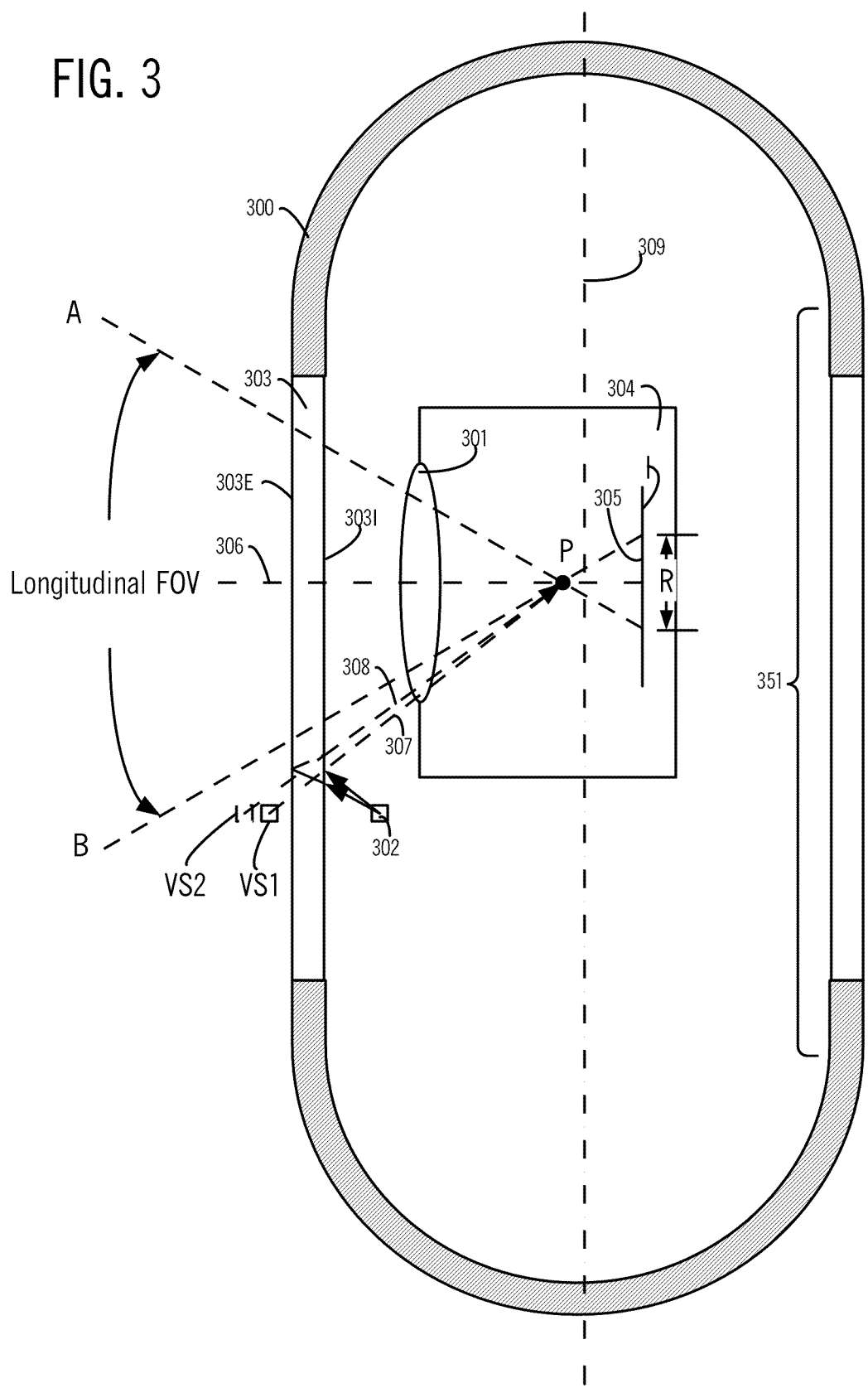
FIGS. 3, 4 and 5 illustrate, in cross-sectional views taken in direction 2E-2E of FIG. 2C, positioning of light source(s) in three embodiments of an endoscope, at locations outside of a field of view of a camera.

A capsule endoscope 300 (FIG. 3) in accordance with the invention images in vivo objects that are close to or touching the capsule housing by use of a lens 301 as an objective of a camera 304. Lens 301 has an associated input pupil P (FIG. 3). Note that FIG. 3 schematically illustrates capsule endoscope 300 with a single objective lens 301, a pupil P, and image plane I on which image 305 forms. For simplicity, camera 304 is shown in FIG. 3 modeled as a pinhole with the input and output pupils collocated and an angular magnification of one.

In FIG. 3, lens 301 has a field of view (FOV) directed, sideways through a window 303 in a tubular wall 351 of capsule endoscope 300. The term FOV denotes a field of view of the overall imaging system in all directions, and is defined by the range of field angles about the optical axis 306 that produces an image 305 on a target region R of the image plane I. The objective lens 301 may have a larger FOV that produces an image that overfills the target region R on the image plane I. For example, the target region R may be defined by all the active pixels on an image sensor I or by a subset of these pixels.

A projection of the FOV in a longitudinal plane of capsule endoscope 300 (FIG. 3) is referred to as longitudinal FOV. An example of longitudinal FOV is the field of view 214 in FIG. 2A. Another projection of the FOV in a lateral plane (perpendicular to the longitudinal plane) is referred to as lateral FOV. If the capsule endoscope is oriented vertically as shown in FIG. 3, the longitudinal FOV is located within a vertical plane (which is the same as the plane of the paper in FIG. 3), and the lateral FOV is in a horizontal plane (perpendicular to the plane of the paper). The longitudinal FOV spans angles on either side of optical axis 306 and is delineated by lines of perspective A and B as shown in FIG. 3. Accordingly, the lateral FOV is located in a plane that passes through an optical axis 306 of capsule endoscope 300 (FIG. 3). The lateral FOVs of multiple objective lenses, included in capsule endoscope 300 and located at different longitudes, overlap at their boundaries such that a 360° panorama is imaged by camera 304 as described above in reference to FIG. 2O.

A short-range light source 302 is located within the capsule endoscope 300 but outside of a body of camera 304. Thus, a portion of the illuminating light from source 302 passes out through tubular wall 351 via an optical window 303. Reflected image-forming light returns into the capsule endoscope 300 through the same optical window 303 and is collected by camera 304 to form an image 305 of the exterior object (not shown in FIG. 3). Camera 304 may also capture illumination light reflected by the exterior surface 303E and interior surface 303I of the window 303. These reflections appear as light spots in image 305, degrading the image's quality and its diagnostic value.

For color imaging by capsule endoscope 300, short-range light source 302 is implemented as a white light source. In some embodiments, the white light source is formed by use of a blue or violet LED encapsulated with phosphors that emit at longer visible wavelengths when excited by the blue or violet LED. In order to minimize the size of the cavity, an LED with conductive substrate is used in several embodiments, so that only one bond wire and associated bond pad is required. Alternatively, multiple LEDs emitting at different wavelengths, such as red, green, and blue, are combined in certain embodiments. Still other embodiments of capsule endoscope 300 use light sources which include organic LEDs (OLEDs), electroluminescent devices, and fluorescent sources.

In some embodiments of capsule endoscope 300, antireflection ("AR") coatings on interior surface 303I and/or exterior surface 303E are used to reduce these reflections. Specifically, using standard processes such as sputtering and evaporation, AR coatings are applied to surfaces that are roughly normal to the line-of-sight flow of material from its source. Accordingly, antireflection coating of a tubular wall of cylindrical shape in a capsule endoscope on its exterior surface 303E is performed in some embodiments. Conformal coatings of materials such as polymers or the imprintation or etching of microstructures onto the tubular wall are various techniques that are used in such embodiments to achieve an AR coating.

AR coatings, which are used on some embodiments of a capsule endoscope 300, are designed to resist scratching at least as well as the polymer material used to form endoscope 300's tubular wall, and satisfy its other requirements such as hydrophobia and biocompatibility. Even with AR coating, some level of reflection is imaged in some embodiments. Moreover, in embodiments of a capsule endoscope wherein AR coatings are either not available or difficult to apply, no AR coatings are used. Instead, certain illuminator and/or camera geometries are used in some embodiments of a capsule endoscope 300, to ensure that internal reflections do not overlap with the image 305 on the image sensor I.

Specifically, as shown in FIG. 3, inner wall 303I and outer wall 303E both reflect light from short-range light source 302 back into capsule endoscope 300. The reflections appear to have come from mirror images of source 302, namely virtual sources VS1 and VS2. The mirror images are distorted in the horizontal direction in FIG. 3 by the cylindrical shape of window 303 which is a portion of tubular wall 351 of endoscope 300. In the vertical direction in FIG. 3, the mirror images VS1 and VS2 are not distorted unless the tubular wall of capsule 300 is not exactly cylindrical. For example, capsule endoscope 300 may be a prolate spheroid.

Tertiary reflections, e.g. optical paths with two reflections off the outer wall 303E and one off the inner wall 303I produce tertiary virtual images that are at a farther distance from capsule endoscope 300 than the virtual sources VS1 and VS2. The tertiary virtual images are much fainter than images VS1 and VS2 for the following reason. The energy in a reflected ray is reduced by $1/R^n$ after n reflections. For normal incidence, the reflectivity is typically 3-5% for polymers in air. The reflectivity of unpolarized light increases with incident angle at a single dielectric interface. Accordingly, the geometry of short-range light source position and objective lens position in some embodiments of a capsule endoscope 300 are independent of whether or not tertiary virtual images are captured by camera 304.

Other reflective surfaces within capsule endoscope 300 may combine with surfaces 303I and/or 303E to produce a significant secondary reflection. For example, if the body of camera 304 is reflective, then two additional virtual sources are produced further outside capsule endoscope 300, than VS1 and VS2. Therefore the body of camera 304 in some embodiments of the invention has a low-reflectivity surface.

If virtual sources VS1 and VS2 lie within the FOV and the source 302 emits into a wide range of angles, then the mirror images VS1 and VS2 are captured in the image 305. If the virtual sources VS1 and VS2 lie outside the FOV, as shown in FIG. 3, they are not imaged. Two exemplary rays are shown in FIG. 3. One ray 307 reflects from the inner wall 3031 towards the pupil. The other ray 308 reflects from the outer wall 303E toward the pupil P. VS1 and VS2 thus have a direct line of sight with the pupil P in object space. However, these lines of sight are outside the FOV so the reflections VS1 and VS2 do not appear in the target image 305.

In certain embodiments of endoscope 300, short-range source 302 is kept a certain distance (e.g. 4 mm) from the optical axis 306. The closer to a longitudinal axis 309 of capsule endoscope 300 that a source 302 is, the greater its distance from optical axis 306. Likewise, the greater the longitudinal FOV (shown in FIG. 3) the further that source 302 is placed from optical axis 306. However, source positioning to keep reflections out of the image as shown in FIG. 3 has certain drawbacks. For example, the volume of the optical system of capsule endoscope 300 increases as source 302 is forced farther from optical axis 306. The height of capsule endoscope 300 is reduced in some embodiments by using small sources 302 (i.e. they occupy an annulus of small width) placed close to window 303 of tubular wall 351. Small sources near the housing of endoscope 300 produce non-uniform illumination and "harsh" shadows. Accordingly, in some embodiments of capsule endoscope 300, large diffuse light sources with incident angles <60° relative to the illuminated object are used as short-range sources 302, to produce better illumination of tissue.

Moreover, white sources with dimensions smaller than a few millimeters are used in some embodiments of capsule endoscope 300. Other embodiments of capsule endoscope 300 use white LEDs that are formed by a blue or violet LED encapsulated in an epoxy with phosphors. Also in certain embodiments of capsule endoscope 300, a die of the LED is located in a reflective cavity along with an encapsulant, a positive electrode and a negative electrode. The reflective cavity is designed to efficiently scatter light from the LED and phosphors, which both emit omnidirectionally, out from the encapsulant into a hemispheric distribution. The die-attach and wirebond processes limit how small the cavity can be made relative to the die.

In some embodiments of capsule endoscope 300, the LED substrate is insulating and two sets of wirebonds are included in the endoscope, to connect the die to each electrode. In other embodiments of capsule endoscope 300, the LED substrate is conductive, and the LED is bonded with conductive epoxy or solder to one electrode and wirebonded to the other electrode. The last-described embodiments have a single wire bond, and result in a capsule endoscope 300 that is more compact than using two sets of wirebonds. One illustrative embodiment uses as source 302, the following: EZBright290 available from Cree, Inc., 4600 Silicon Drive, Durham, N.C. 28703, USA Tel: +1.919.313.5300, www.cree.com.

In some embodiments, an endoscope 400 (FIG. 4) has a short-range light source 409 that includes a reflective cavity 401 and light emitting diode (LED) 402. Cavity 401 directs light from LED 402 through an aperture 403, and out of endoscope 400 through a window 404 of the tubular wall. In these embodiments, the light source is positioned at a predetermined distance 405 (measured along a longitudinal axis which is not shown in FIG. 4) from the optical axis 406 such that an aperture 407 of a virtual source VS3 is outside the FOV.

In certain embodiments, a short-range light source is placed such that one or more of its mirror images would be within the FOV, but for the presence of internal walls (i.e. baffles) which are deliberately positioned between the light source and the window in the tubular wall to ensure that no line-of-sight exists from the pupil to the virtual images. For example, in one such embodiment illustrated in FIG. 5, a light source S is higher than (i.e. closer to the optical axis than) the light source 302 in FIG. 3 such that in FIG. 5 a portion of virtual image VS4 is located within the FOV. The endoscope of FIG. 5 also includes a baffle that is perpendicular to the tubular wall of the endoscope and located above the light source S. In the example illustrated in FIG. 5, the endoscope's tubular wall is oriented vertically, and a baffle 501 is oriented horizontally, mounted peripherally, and located in a plane between the objective and the light source S. Baffle 501 is formed as an annular wall in one illustrative embodiment.

Figure 5:
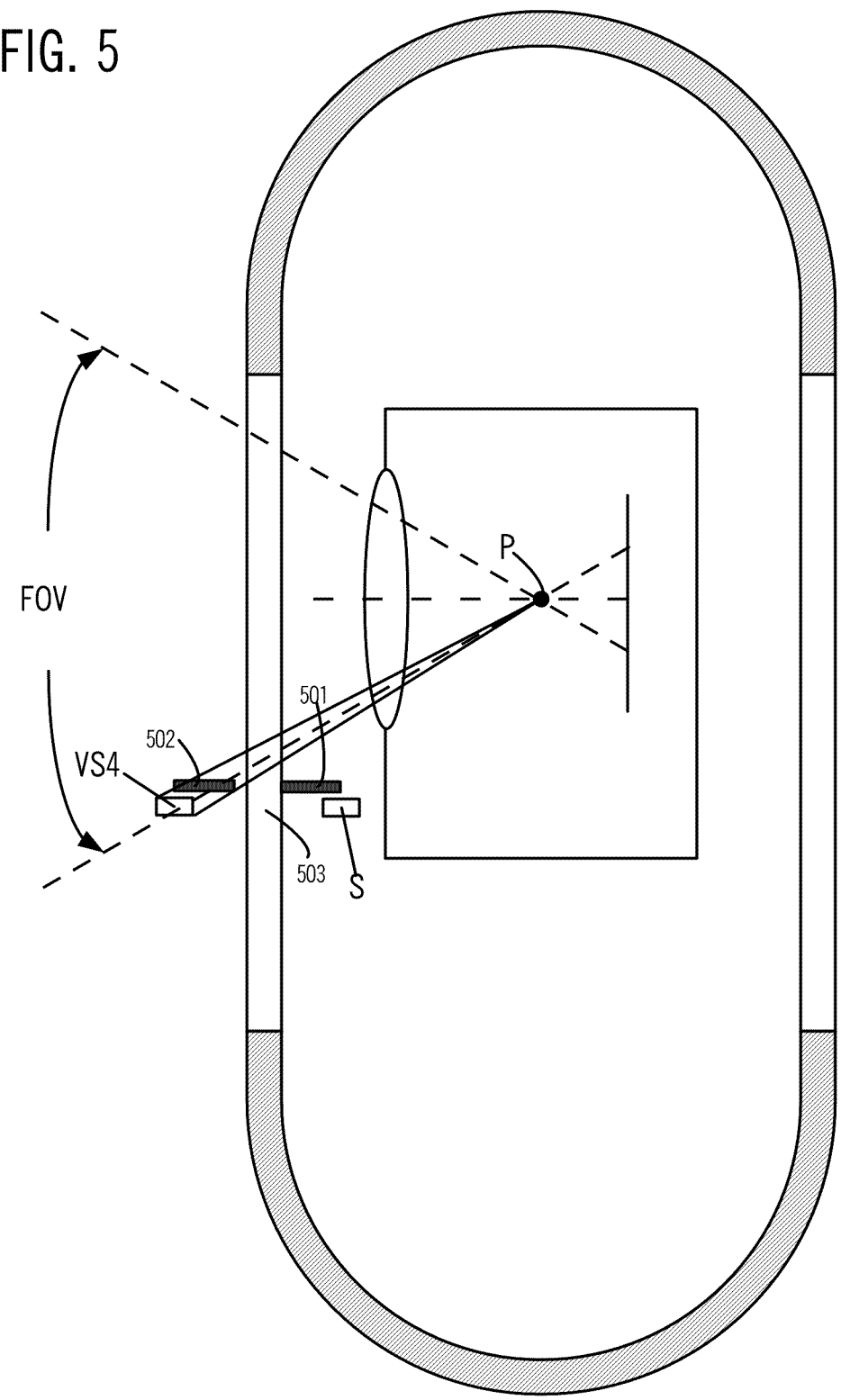

Baffle 501 reflects or absorbs incident rays, such as rays from source S or rays reflected by window 503. In the embodiment of FIG. 5, a virtual image 502 of the baffle blocks the line-of-sight between virtual image VS4 and P within the FOV. Note that the baffle 501 creates a shadow on an object (e.g. tissue) which is illuminated outside the endoscope, which can be a disadvantage if captured in a diagnosable image. Note that mirror 218 in FIG. 2E is a baffle because it blocks rays originating at source 205 from forming a virtual image that can be captured by the camera.

Figure 6:
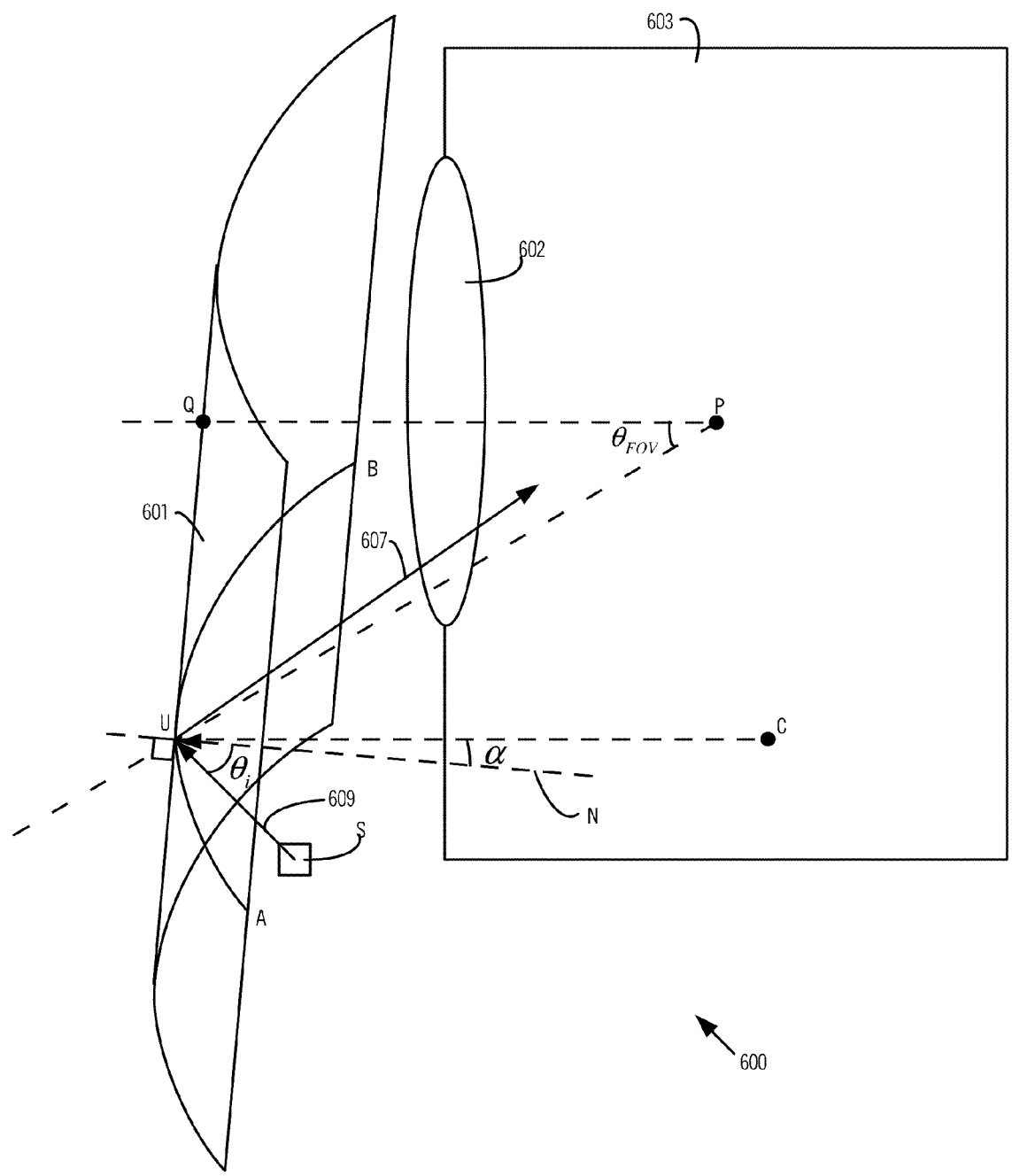
FIG. 6 illustrates, in an enlarged view of an endoscope of the type shown in FIG. 3, an angular relationship implemented in some embodiments, between a light source, an objective lens of a camera, and surface of the tubular wall.

In some embodiments, an aperture through which a source emits lies partially or fully within the FOV although the range of ray angles emitted from the aperture is restricted as illustrated in FIG. 6. Specifically, in FIG. 6 a ray emitted from an aperture of source S is reflected from the window 601 at a point U. The projection of the ray onto a vertical plane containing U and the center of curvature C of the arc AUB (defined by the intersection of window 601 with a plane containing U and parallel to optical axis PQ) at U makes an angle $\theta_i$ with the normal N to window 601. For a window 601 of a cylindrical shape, C is on the longitudinal axis (not shown in FIG. 6) of the endoscope 600. Let $\alpha$ be the angle between the normal and optical axis PQ. The reflected ray 607 (FIG. 6) does not enter pupil P if $\theta_i > \theta_{FOV} + \alpha$ and this condition is satisfied in some embodiments of endoscope 600, in accordance with the invention.

Figure 7:
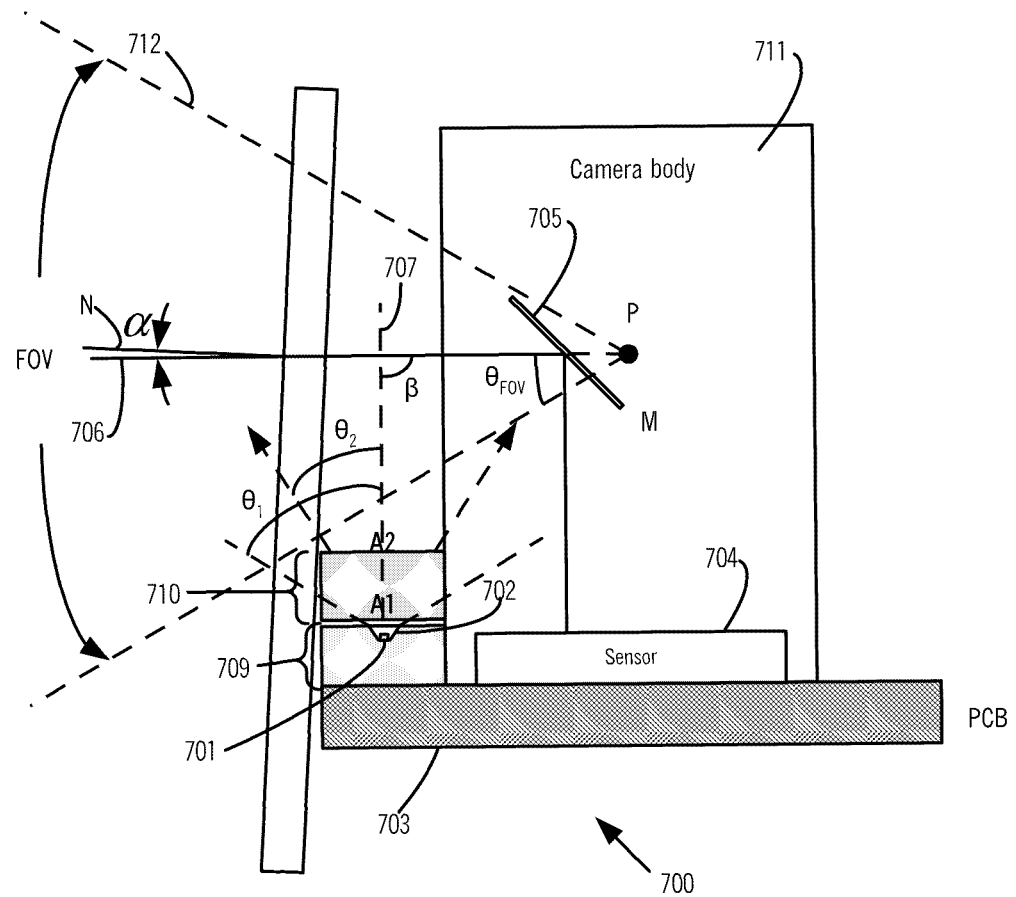
FIGS. 7, 8 and 9 illustrate, in an enlarged view of an endoscope of the type shown in FIG. 3, an optical element used in some embodiments, to reduce angular dispersion of a light emitter.

FIG. 7 illustrates an endoscope 700 of some embodiments including a short-range source 709 formed by a LED 701 located within a cavity 702 and mounted on a printed circuit board (PCB) 703. On the same PCB 703 is mounted an image sensor 704. A mirror 705 folds the optical axis and directs image forming light onto sensor 705. Short-range source 709 emits light into an input aperture A1 of an optical element 710 that reduces the light's angular dispersion, i.e. an angular concentrator 710. Light exits concentrator 710 through an output aperture A2.

In certain embodiments of endoscope 700, angular concentrator 710 limits the angular divergence in all directions to a half-angle of $\theta_2$, and $\beta$ is the angle between the optical axis 706 of camera 711 and optical axis 707 of the concentrator 710 and a is the angle (see FIG. 6) between a housing surface normal N and the camera's optical axis 706. Such embodiments ensure that internal reflections are outside the FOV by satisfying the following relationship $\theta_2 < \beta - \theta_{FOV} - 2\alpha$. Note that for several of these embodiments, $\beta$ is in the range 45° to 135°. In some embodiments, window 712 is of cylindrical (or conical) shape, the pupil P is located on the longitudinal axis of the cylinder (or cone), and concentrator 710 only limits the divergence in the radial direction (with respect to the window) to θ₂. These conditions are not met in other embodiments which limit the divergence in the tangential direction as well, although not necessarily to an angle as small as θ₂. In general, the divergence is limited such that $\theta_i > \theta_{FOV} + \alpha$ where $\theta_i$ is as defined above for all rays emitted from A2.

In a number of embodiments of an endoscope 700, the maximum angular concentration in one dimension is defined from the radiance theorem as $$C_{max} = \frac{\sin\theta_1}{\sin\theta_2} = \frac{a_2}{a_1}$$

Where $\theta_1$ and $\theta_2$ are the incident and exit angles, $a_1$ and $a_2$ are the input and exit aperture diameters. The definition of $C_{max}$ assumes that the input and exit media are air. If the input aperture A1 of concentrator 710 is positioned directly on the encapsulant in cavity 702 wherein LED 701 is mounted, only those rays that do not suffer total internal reflection enter the concentrator 710, and the input is considered to be these rays after refraction into free space. $C_{max}$ quantifies the maximum possible reduction in angle with concentrator 710, relative to without the concentrator. If $\theta_1 = \pi/2$ then $$\sin\theta_2 \geq \frac{a_1}{a_2}.$$

Figure 8:
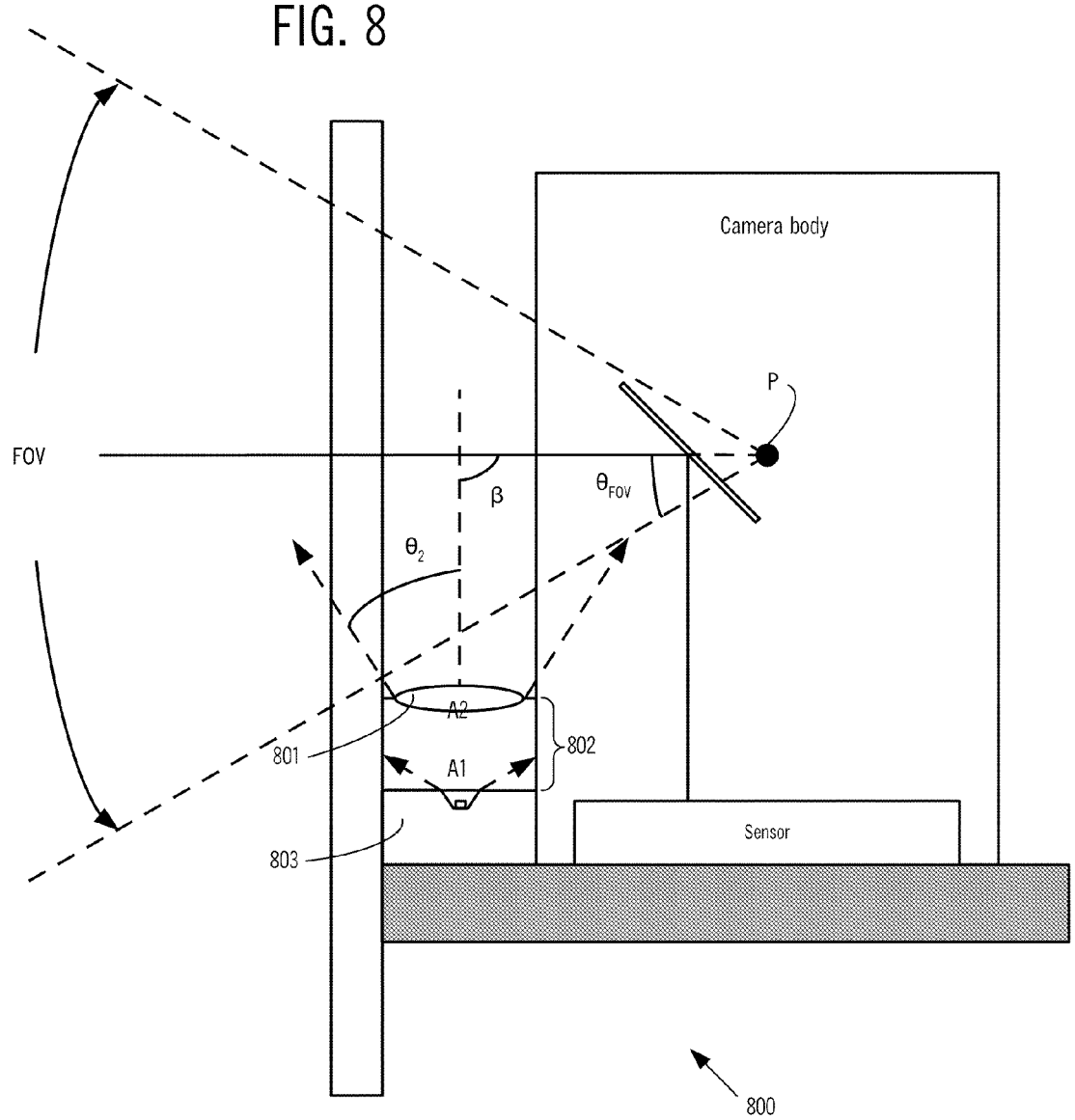

FIG. 8 illustrates an endoscope 800 using a collimating lens 801 to form an angular concentrator 802 to reduce the angular divergence of light from the short-range source 803. In FIG. 8, the concentration ratio is limited by the numerical aperture (NA) of lens 801. Since $\theta_1 = \pi/2$ much of the light from source 803 entering input A1 does not pass through lens 801. In general, imaging systems, even complicated ones with multiple lenses, are not efficient angle concentrators (i.e. collimators) if the numerical aperture (NA) required approaches one.

Figure 9:
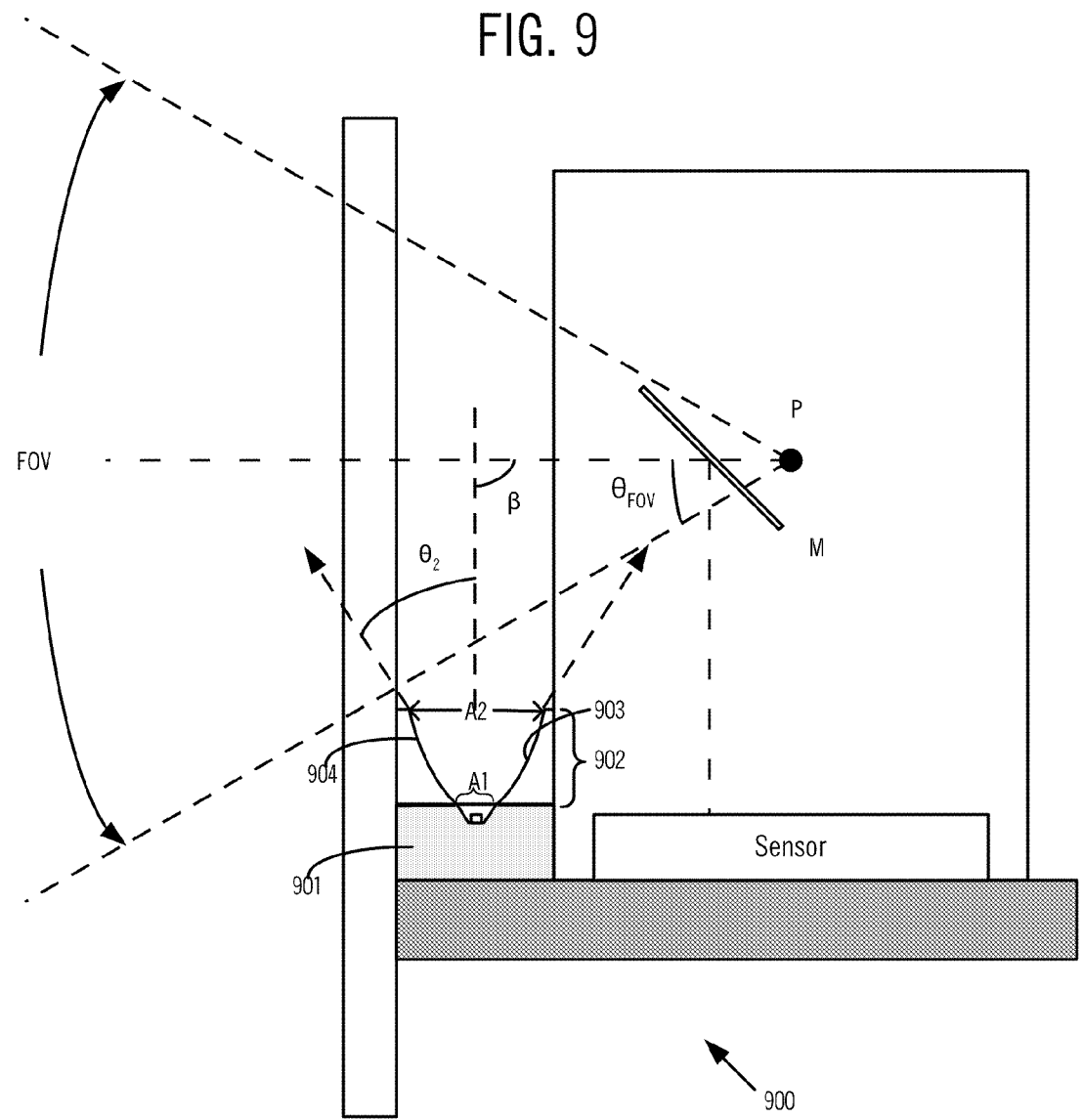

The concentration ratio of non-imaging concentrators, on the other hand, can approach $C_{max}$. FIG. 9 illustrates an endoscope 900 using a compound parabolic concentrator (CPC) 902 as the angular concentrator. The sides of concentrator 902 have reflective surfaces 903 and 904. Depending on the embodiment, the body of concentrator 902 may be hollow as shown with mirrored surfaces 903 and 904 of sidewalls, or alternatively the body of the concentrator 902 is a dielectric with side walls whose surfaces 903 and 904 face each other and reflect light from each to the other, using total internal reflection (TIR). Hence some embodiments of endoscope 900 use two-dimensional CPCs, which are trough shaped, to approximate or even reach the maximum theoretical optical concentration. Variations of endoscope 900 in such embodiments include truncated CPCs for which the height is reduced with only a small loss of concentration ratio. Certain embodiments of endoscope 900 use other forms of concentrators, with planar sloped walls for example, achieve a lower concentration ratio than the CPC but may still be useful.

Figure 10:
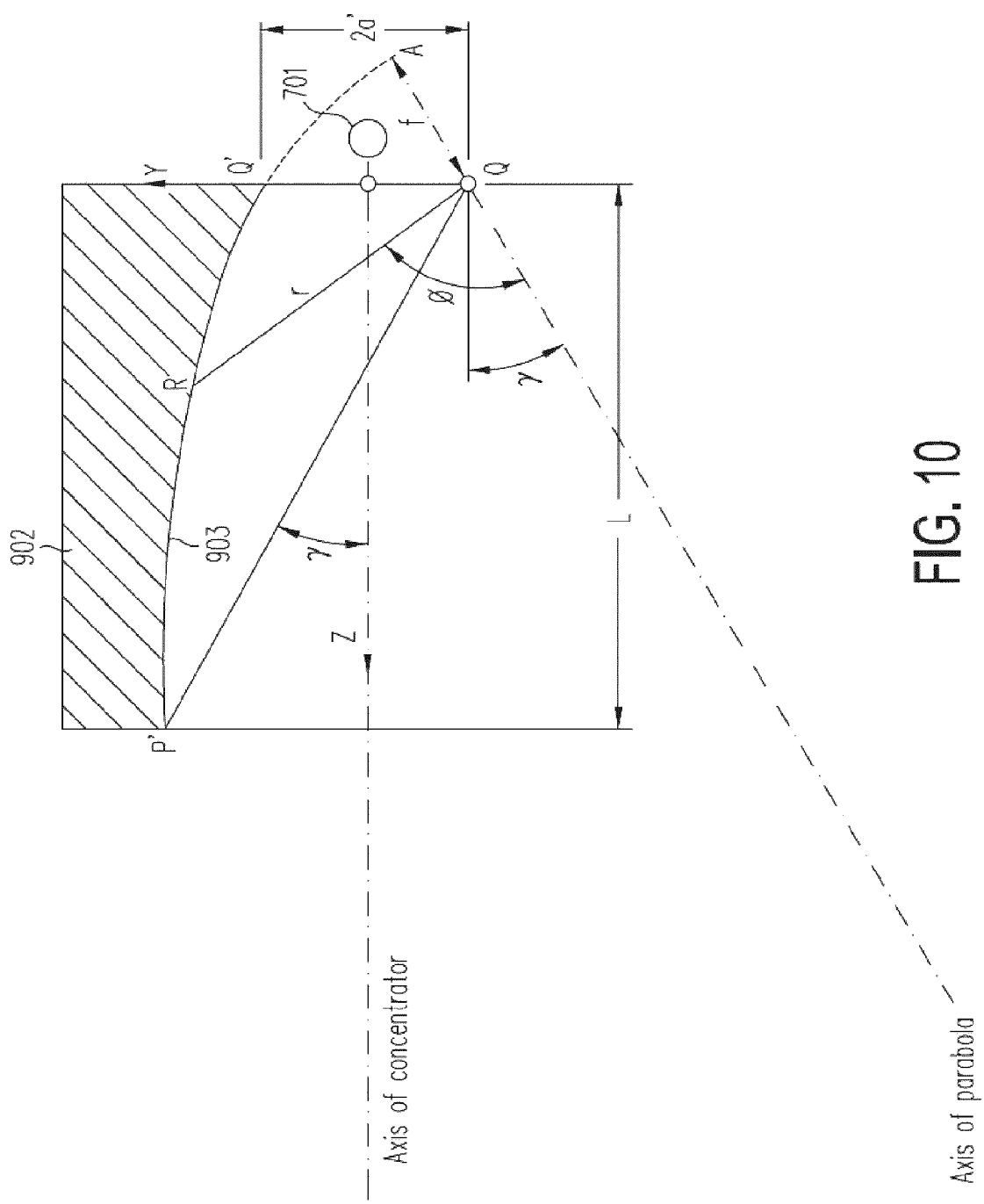
FIG. 10 illustrates an embodiment wherein the optical element is implemented by an angular concentrator which is positioned so that its axis "Z" passes through a location of the light emitter.

The geometry of a cross section of a CPC 902 that is used in some embodiments of endoscope 900 is illustrated in FIG. 10. The input aperture of CPC 902 is QQ'. The profile P'Q' of one surface 903 of concentrator 902 is a portion of a parabola with focus at Q and axis at an angle γ to the axis Z of concentrator 902. Note that the LED 701 is located on the axis Z directly facing input aperture QQ'. The length L of concentrator 902 is chosen in some embodiments of endoscope 900 such that a skew ray from Q intersects the parabola at P'. The emission half-angle is $\theta_2 = \gamma$. A truncated CPC reduces L and $\theta_2 > \gamma$. Details may be found in *Nonimaging Optics*, R. Winston, J. C. Minano, P. Benitez, Elsevier Academic Press, 2005, pp. 43-97 and 467-479 which is incorporated by reference herein in its entirety.

Figure 11:
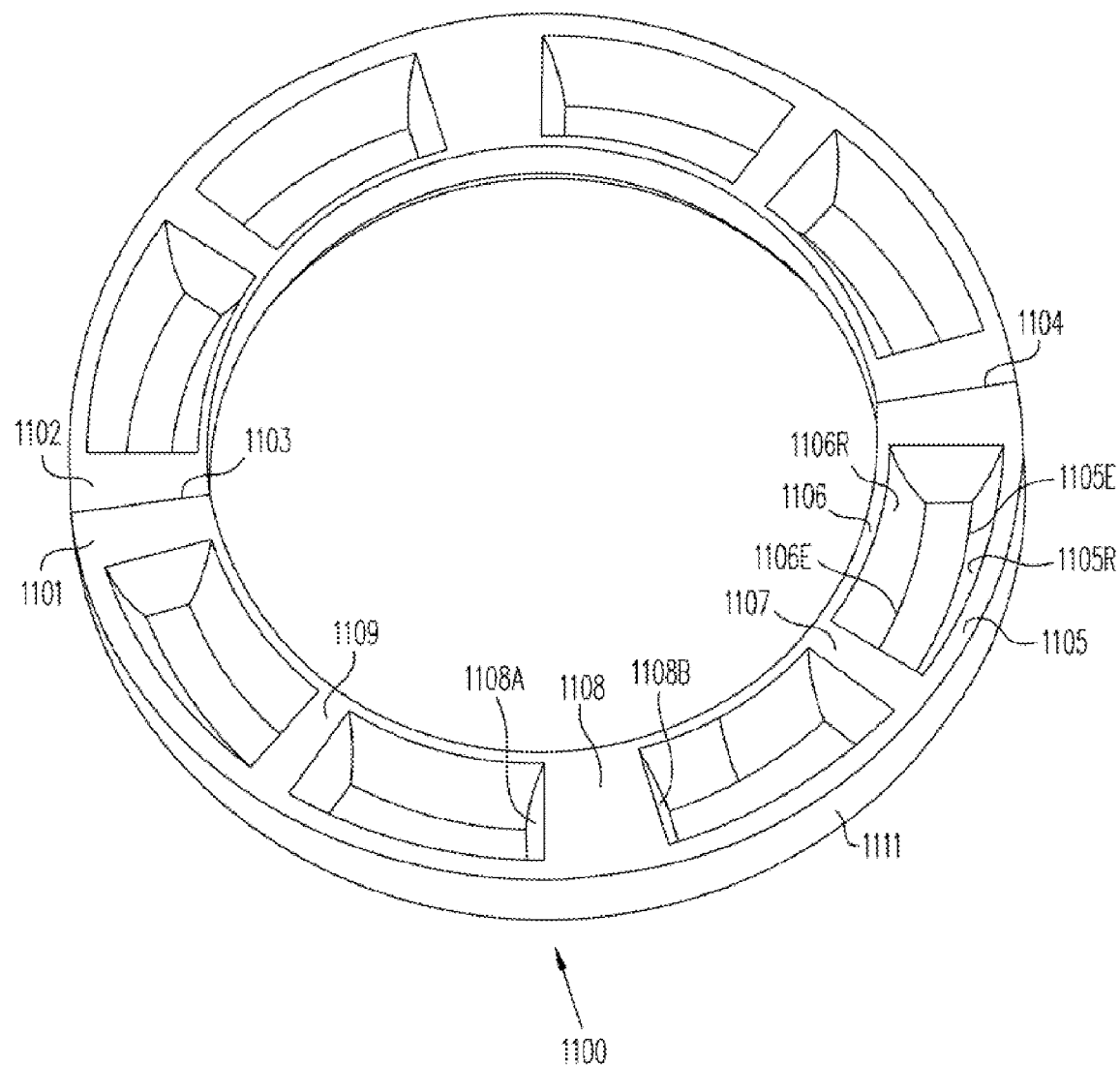
FIG. 11 illustrates, in a perspective view, an annular angular concentrator that is used in some embodiments of an endoscope.

Some embodiments of an endoscope 900 include a cylindrical capsule enclosing a panoramic imaging system with an annular CPC 1100 of the type shown in FIG. 11. The cross-section of CPC 1100 in a plane containing a radius is a two-dimensional CPC as illustrated in FIG. 10. CPC 1100 includes two halves, namely a first half 1101 and a second half 1102 that are each glued to a ring (called "LED ring"). Each half includes two sidewalls that are physically attached to one another by radial spokes for structural support. For example, in FIG. 11, the first half 1101 has an outer sidewall 1105 and an inner sidewall 1106 that face each other, with spokes 1107-1109 providing support therebetween. Note that the two halves 1101 and 1102 of CPC 1100 are mirror images of each other, and for this reason when only the first half 1101 is described below it is to be understood that second half 1102 has similar dimensions, properties etc.

Note that in FIG. 11, outer sidewall 1105 surrounds inner sidewall 1106. Surface 1106R of inner sidewall 1106 faces surface 1105R of outer sidewall 1105, and these two surfaces 1106R and 1105R reflect light such that it is deflected upwards. Sectioning sidewalls 1105 and 1106 along a radius of CPC 1100 results in a cross-section which forms a two dimensional CPC as illustrated in FIG. 9. Edges 1106E and 1105E of respective sidewalls 1106 and 1105 are adjacent to one another in a bottom lateral plane. Accordingly, edges 1106E and 1105E together with edges of two adjacent spokes define a boundary of an input aperture of CPC 1100 at its bottom surface (not shown in FIG. 11; see FIG. 12E).

In some embodiments, short-range sources in the form of LEDs are positioned beneath each input aperture of CPC 1100 in a lead frame or package (not shown in FIG. 11; see FIG. 13). Specifically CPC 1100 has, on a bottom surface 1201 (FIG. 12A), several outward projections or bosses, such as bosses 1202 and 1203. The bosses are button shaped and are dimensioned and positioned to fit into and mate with corresponding depressions or pockets in a lead frame wherein the LEDs are mounted. Moreover, an outer surface 1111 (which is a surface of outer sidewall 1105) is made diffusing so that light from the input aperture diffuses laterally out of surface 1111.

Figure 12E:
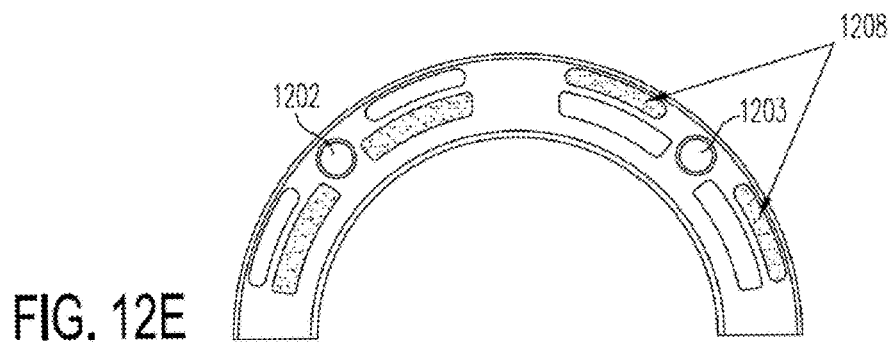
FIG. 12E illustrates, in a bottom elevation view, a half portion of the annular angular concentrator of FIG. 11.
Figure 12D:
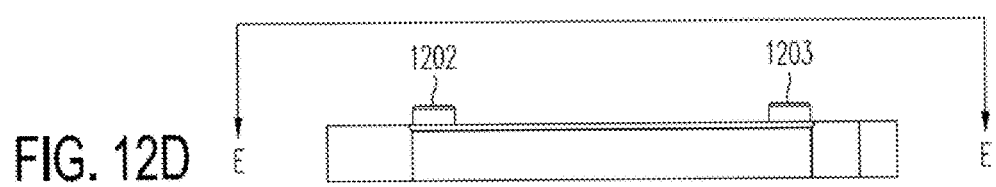
FIG. 12D illustrates, in a side view in the direction D-D, in FIG. 12C, the half portion of the annular angular concentrator.
Figure 12C:
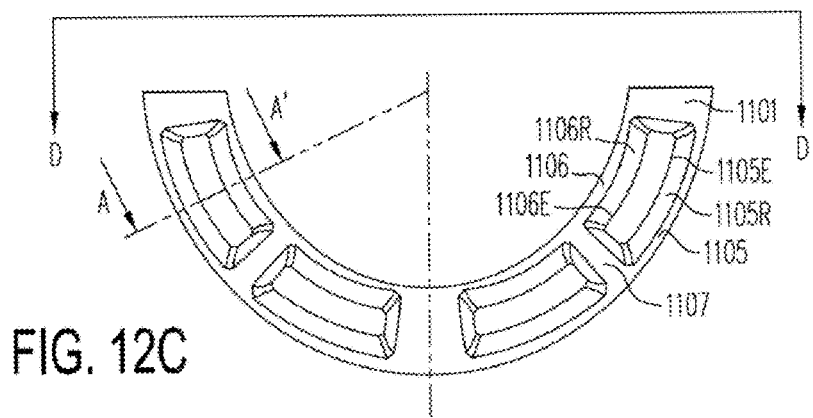
FIG. 12C illustrates, in a top elevation view, one half portion of the annular angular concentrator of FIG. 11.
Figure 12B:
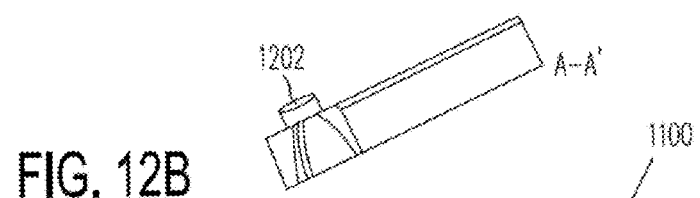
FIG. 12B illustrates, in a cross-sectional view in the direction A-A, in FIG. 12C, a portion of the annular angular concentrator of FIG. 12A.
Figure 12A:
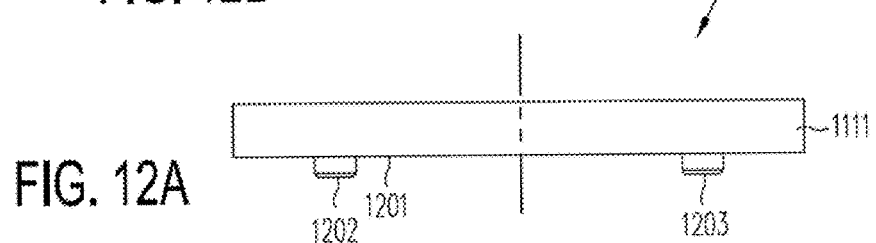
FIG. 12A illustrates, in a side view an annular angular concentrator shown in FIG. 11.

FIG. 12C illustrates, in a top elevation view, first half 1101 of CPC 1100 of FIG. 11. FIG. 12B illustrates, in a cross-sectional view in the direction A-A, in FIG. 12C, first half 1101 of annular CPC 1100 of FIG. 11. FIG. 12D illustrates, in a side view in the direction D-D, in FIG. 12C, the first half 1101 of FIG. 11. FIG. 12E illustrates, in a bottom elevation view, in the direction E-E, in FIG. 12C, first half 1101 of FIG. 11. Note that portions 1208 of the bottom surface of CPC 1101 are made diffusing so that light incident thereon is transmitted through CPC 1101 and exits laterally through outer surface 1111 (FIG. 12A). The height of side walls 1105 and 1106 are 1.0 mm.

In some embodiments of an endoscope, CPC 1100 is formed as a molded polymer with a metal coating on the inside surfaces 1106R and 1105R to form mirrors. The walls of spokes 1107-1109 are sloped mirror-like planes that help to direct light upwardly. For example, spoke 1108 in FIG. 11 has spoke walls 1108A and 1108B that provide a degree of concentration in the tangential direction. Spokes 1107-1109 block rays from LEDs located underneath the input apertures of CPC 1100 with a large tangential component that would otherwise lead to ghost images of the LEDs when internally reflected from the endoscope's housing, if the camera pupils are not located on the longitudinal axis of the endoscope. Depending on the embodiment, spokes 1107-1109 may be absorbing instead of reflecting although this reduces the efficiency in energy usage by the endoscope.

Figure 14A:
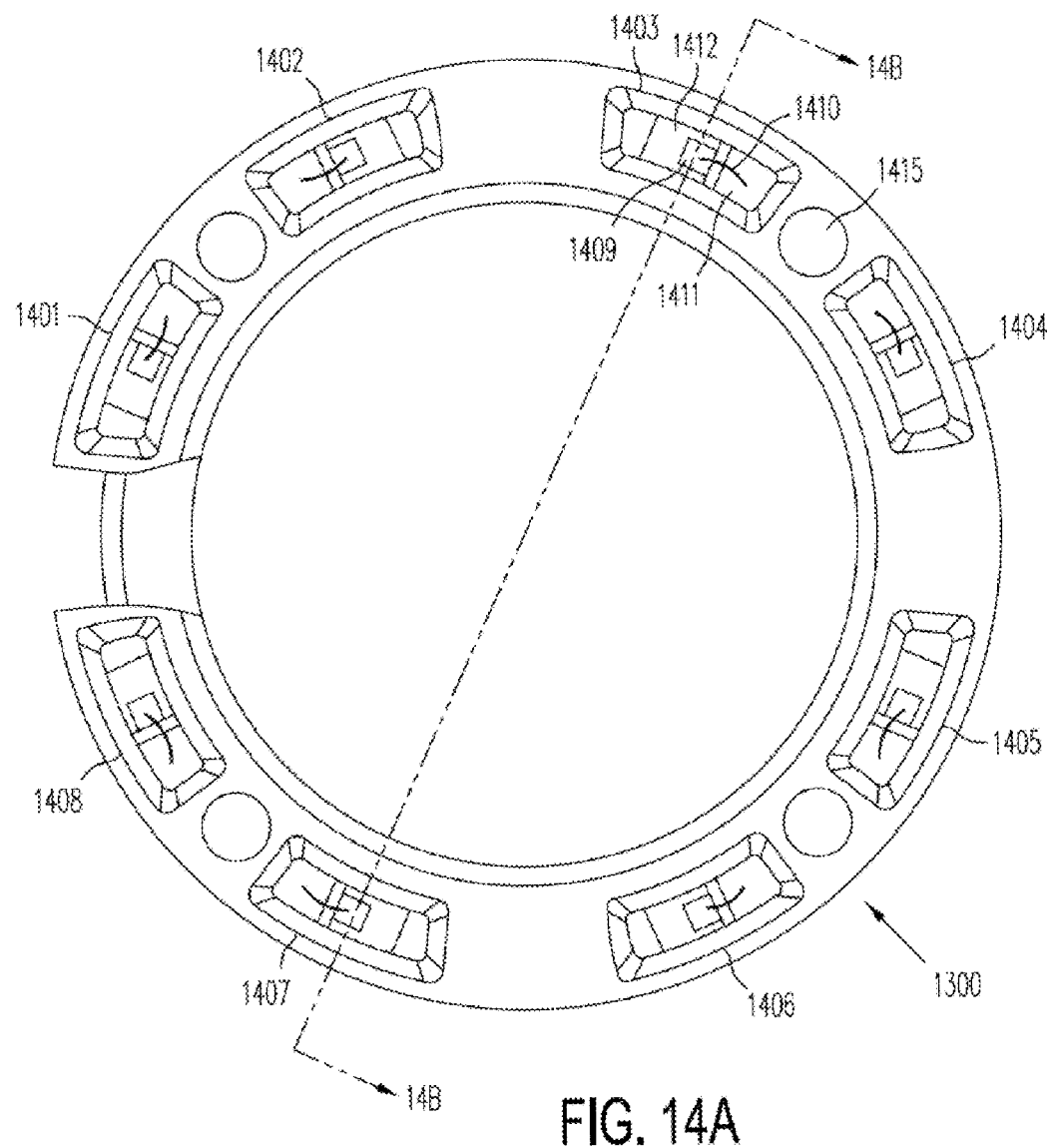
FIGS. 14A and 14B illustrate, in a top view and a side view respectively, an assembly of multiple light emitters and an annular concentrator in some embodiments of an endoscope
Figure 14B:
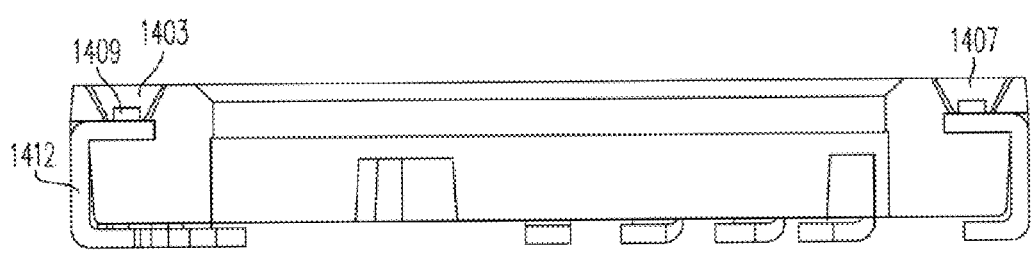

FIG. 13 illustrates certain embodiments of an endscope that includes CPC 1100 of the type described above in reference to FIGS. 11 and 12A-12E, mounted on a lead frame 1300 such that LEDs supported therein face input apertures in CPC 1100. In some embodiments, length L is on the order of 1 mm. LED lead frame 1300 of the embodiments shown in FIG. 13 is also ring shaped as illustrated in FIGS. 14A and 14B. Lead frame 1300 contains multiple cavities 1401-1408 (FIG. 14A). Each of cavities 1401-1408 holds an LED encapsulated therein with a phosphor in epoxy. For example, in FIG. 14A, cavity 1403 holds an LED 1409 that is connected by a single bondwire 1410 to cathode lead 1411. Cavity 1403 also holds an anode lead 1412. In some embodiments, the walls of each cavity of lead frame 1300 are white diffuse reflectors.

LED lead frame 1300 also has a number of pockets, such as pocket 1415 (FIG. 14A) that mates with and holds button shaped bosses of CPC 1100 when they are press-fit or otherwise inserted. Note that in some embodiments the just-described bosses and pockets are reversed in position, i.e. the CPC has pockets and the LED lead frame has bosses. Also depending on the embodiment, other structures may or may not be used to physically join LED lead frame 1300 and CPC 1100 to one another.

In the embodiment shown in FIG. 13, the LED lead frame 1300 has cavity 1403 with an aperture A3 that is located only partially under input aperture A1 of the CPC 1100. Specifically, a portion of aperture A3 of cavity 1403 is covered by a surface 1208 of outer sidewall 1105 of CPC 1100. In one illustrative example, A3 is 0.9 mm and A1 is 0.5 mm. Hence, light from LED 1409 enters sidewall 1105 through surface 1208. Surface 1208 of some embodiments is diffusive as shown in FIG. 12E. Any such light which has entered sidewall 1105 then passes laterally through outer surface 1111 to a scene outside the endoscope, if the CPC's outer sidewall is transparent. A portion of this light which exits surface 1111 is reflected by the reflective cavity surface of CPC 1100.

Surface 1111 at the outer rim of CPC 1100 has a rough surface so that light exiting the endoscope from surface 1111 is scattered and diffused, which is used to illuminate objects at a short to intermediate distance from the endoscope (see FIGS. 2I, 2J and 2K). In the endoscope structure illustrated in FIG. 13, the same LED provides short-range light to illuminate objects at a short or intermediate distance from the endoscope by diffuse illumination through surface 1111, and also provides additional short-range light via aperture A2 for use in radially illuminating objects touching or a short distance from the endoscope. For example, an annular mirror (see mirror 218 in FIGS. 2E, 17 and 18) reflects a portion of light that exits aperture A2, out of a window of a tubular wall of the endoscope, and simultaneously another portion of the light exits out of the window directly from aperture A2.

Figure 15:
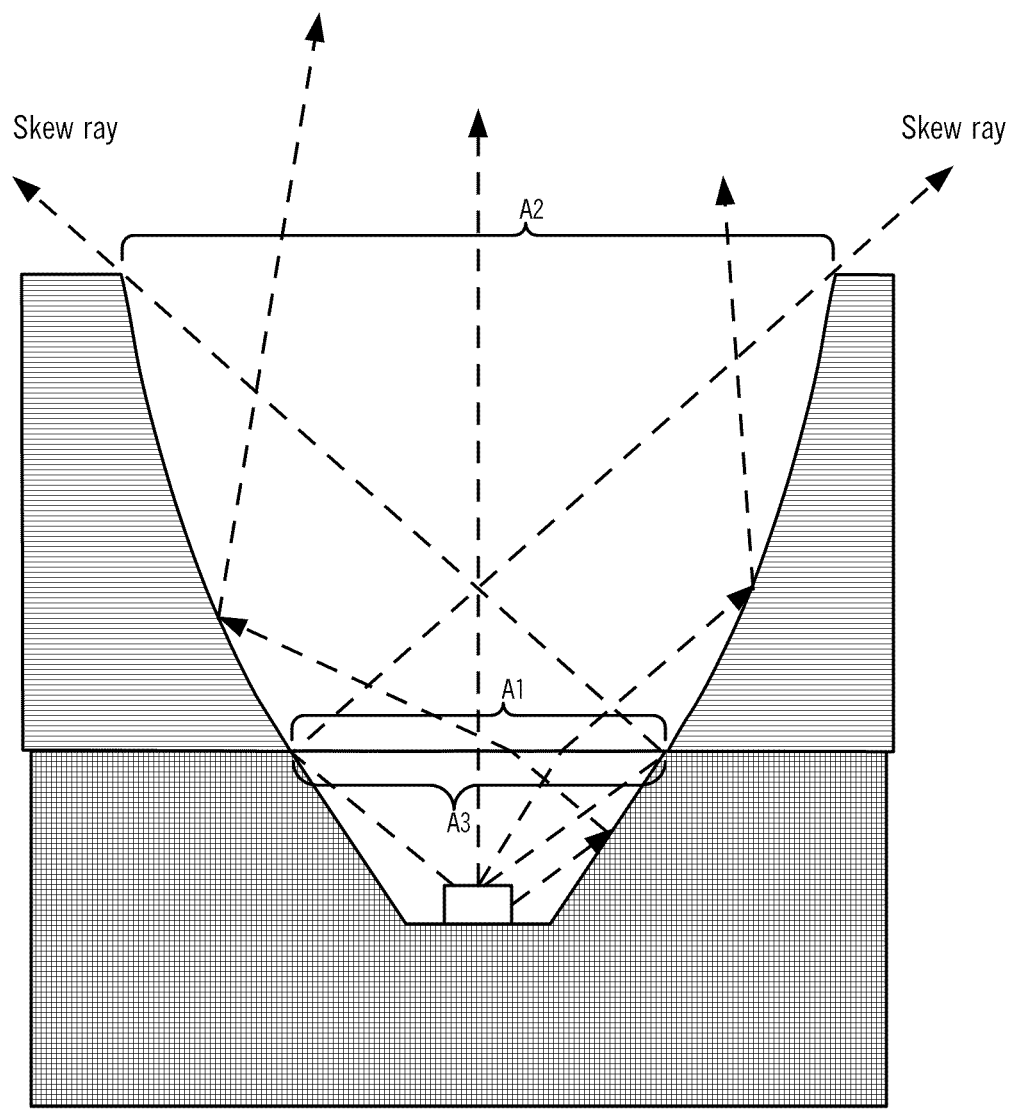
FIGS. 15 and 16 illustrate, in cross-sectional views, two alternative embodiments of combination of a light emitter and a concentrator, in accordance with the invention.
Figure 16:
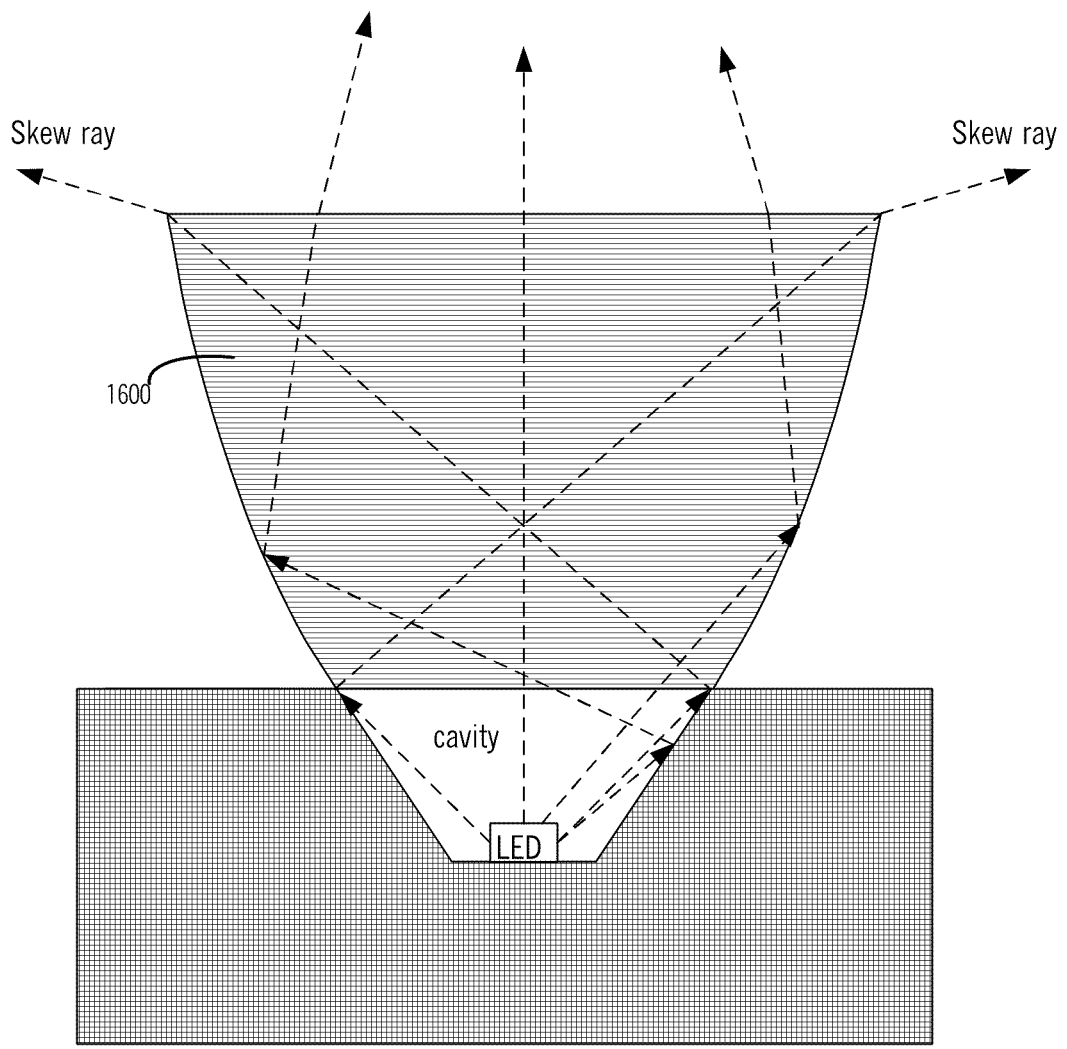

In some embodiments, a CPC of an endoscope has an input aperture A1 that coincides with the aperture A3 of a short-range source, wherein there is no overlap (or negligible overlap) of the CPC's outer sidewall with the lead frame's cavity as shown in FIG. 15. Also, in certain embodiments, a CPC 1600 in an endoscope is made of a dielectric material as shown in FIG. 16, although the concentration ratio is reduced for a given length L of CPC due to refraction at the output aperture.

Figure 17:
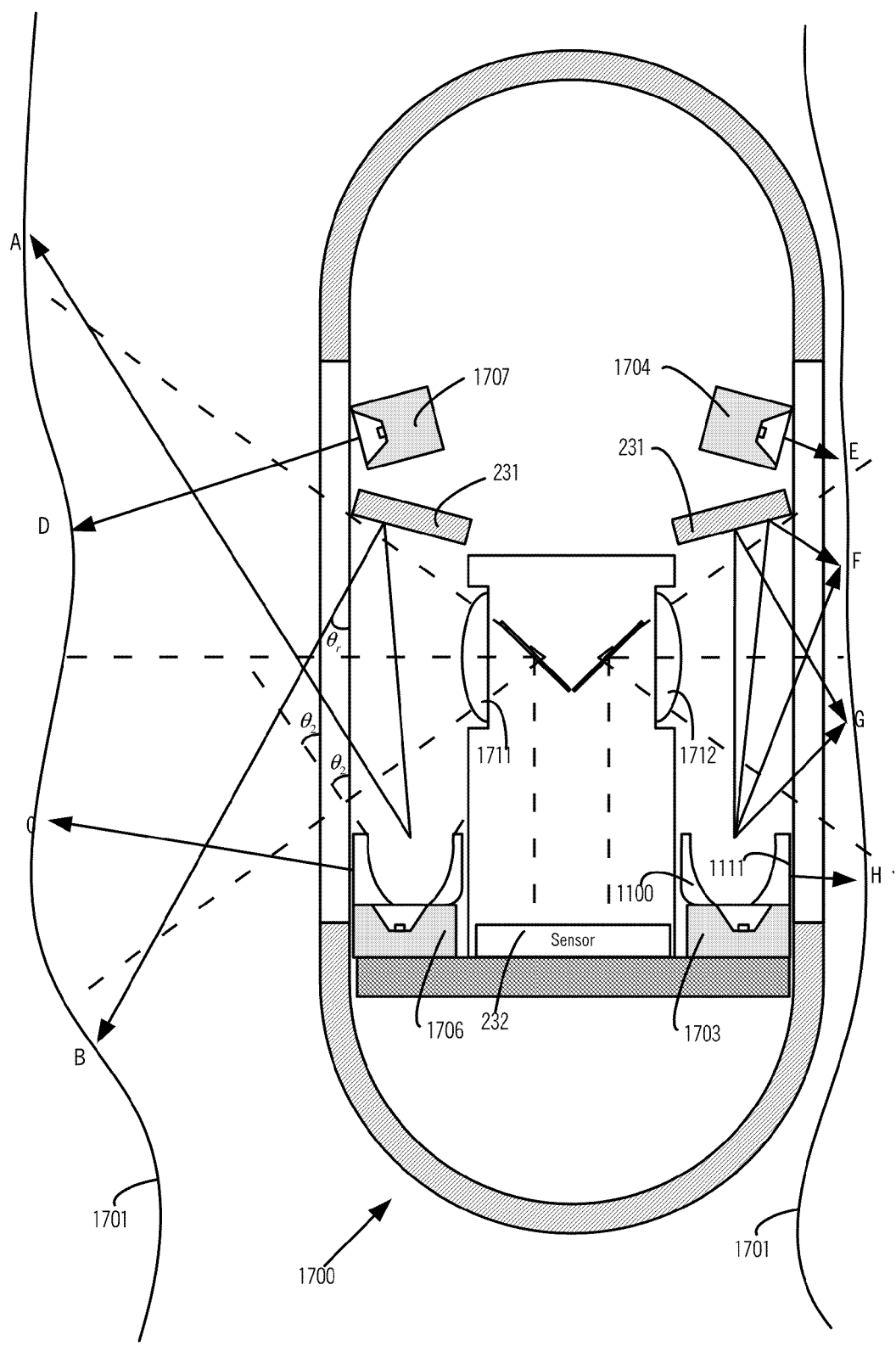
FIG. 17 illustrates use of an endoscope having two light emitters, for illumination and imaging over short distances, in accordance with the invention.

Some embodiments of an endoscope of the type described herein provide multi-modal illumination in accordance with the invention, by using different amounts of energy to illuminate tissue, depending on the distance of the tissue. Specifically as illustrated in FIG. 17 on the right side, mucosa surface 1701 at points F and G which is close to (e.g. <5mm) or touching endoscope 1700, is illuminated by light emerging from CPC 1100, both directly and after reflection from annular reflector 218. In the illustrative embodiment shown in FIG. 17, reflector 218 enables light from an emitter in short-range source 1703 to reach an illumination region of the endoscope from both sides of the field of view, thereby to illuminate tissue surface 1701 more uniformly in an image to be diagnosed, as compared to short-range illumination from only one side of the field of view.

Additionally, a tissue surface 1701 located at point H which is in contact with endoscope 1700 is also illuminated by light emerging from surface 1111 which light entered CPC 1100 through a bottom surface as described above, and is reflected by a convex surface in CPC 1100. As tissue surface 1701 is in contact with endoscope 1700, point H is outside the FOV of the camera. However, as the distance increases, point H falls within the FOV. Accordingly, endoscope 1700 uses a minimum amount of energy, e.g. by using primarily just a single LED within short-range source 1703 in the direction towards the right of FIG. 17.

Note that endoscope 1700 of these embodiments includes an additional LED used for long-range source 1704 that, when turned on, also provides light in the same radial direction, i.e. towards the right of FIG. 17. Long-range source 1704 is positioned longitudinally offset from the objective's optical axis, e.g. positioned behind mirror 218 which acts as a baffle. Note that there is little or no overlap between the long-range illumination region on the endoscope's tubular wall (close to point E in FIG. 17) lit up by light source 1704, and the above-described short-range illumination region lit up by light source 1703. The area of long-range illumination region lit up by light source 1704 is several times and in some cases an order of magnitude, smaller than the corresponding area of short-range illumination region lit up by light source 1703.

Endoscope 1700 increases the radiant energy generated by the long-range light source 1704 as the distance of the tissue to be imaged increases. Using long-range light source 1704 simultaneously with short-range light source 1701 provides sufficient illumination to image mucosa 1701 that is located far away (e.g. ~20 mm away). For example, points A-D shown on the left side of FIG. 17 are illuminated by turning on both light sources 1706 and 1707.

Use of both light sources 1706 and 1707 does use up a maximum amount of energy (relative to use of just one source 1706), although such use provides better images which enable a more thorough diagnosis of a body cavity, such as a gastrointestinal tract. The energy generated by multiple light sources 1703 and 1704 to illuminate radially in a given direction may be scaled appropriately, to illuminate tissue located at intermediate distance(s) as described above in reference to FIG. 2I. Accordingly, endoscope 1700 in some embodiments of the invention operates multi-modally, specifically in a minimum energy mode, a maximum energy mode and one or more intermediate energy modes. For certain body cavities, such as a small intestine, endoscope 1700 of these embodiments operates continuously in a minimal mode, by turning on only the short-range source, e.g. source 1703 (i.e. the long-range source is kept turned off).

Note that endoscope 1700 of FIG. 17 incorporates four objectives with optical axes spaced 90° apart, although only two lenses 1711 and 1712 that are oppositely directed are shown in FIG. 17. In this embodiment, eight LEDs are arrayed in a ring under an annular truncated CPC 1100. The eight LEDs emit out the outer surface 1111 of CPC 1100 and also through the top of the CPC apertures A2 (not labeled in FIG. 17). Some of the light from aperture A2 is reflected down and out of the endoscope 1700 by annular mirror 218 located above the imaging region. In FIG. 17, the angle of the mirror 218 relative to the optical axis is chosen such that the reflected light satisfies the relationship $\theta_r < \theta_2$ where $\theta_2$ is the maximum angle of light exiting the CPC cavity in the radial direction and $\theta_r$ is the angle of a ray reflected from the annular mirror relative to an inner or outer surface of the tubular wall.

Figure 18:
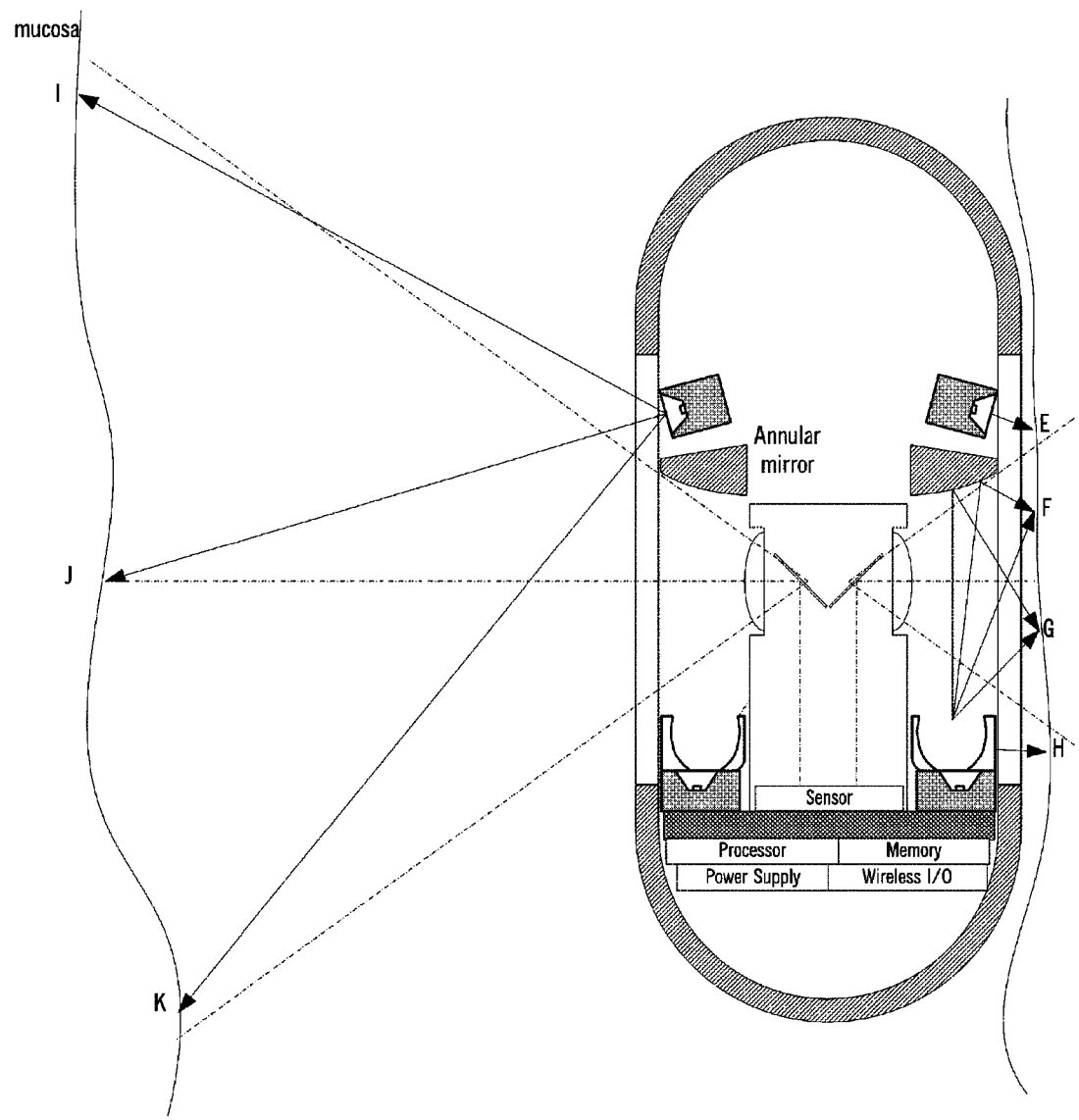
FIG. 18 illustrates use of the endoscope of FIG. 17 for long range illumination and imaging, also in accordance with the invention.

Note that the embodiment illustrated in FIG. 18 is similar or identical to the embodiment described above in reference to FIG. 17 except that in FIG. 18 the annular mirror has a convex cross section. The convex cross-section mirror is used because the relationship $\theta_r < \theta_2$ need not be satisfied for all reflected rays. The shape of the mirror's reflective surface is empirically chosen, to optimize uniformity of illumination. In one illustrative embodiment, a convex section of the reflective surface has a radius of curvature close to 10 mm.

In the embodiments of FIGS. 17 and 18, the outer rim of the CPC is sufficiently below the optical axis so that virtual images of it are outside the FOV. Thus, no single-reflection ghost images of it will be visible. The light emitted from the cavity of the CPC is restricted in angle so that reflections will miss the camera pupil. Additionally, as noted above, in order to illuminate distant objects, set of LEDs is arrayed around the endoscope, above the mirror. The output apertures of these LEDs are sufficiently above the optical axis so that single-reflection ghost images are outside the FOV. If the mucosa is close, these LEDs primarily illuminate region E which is outside the FOV, and for this reason the LEDs need not be turned on. If the mucosa is at an intermediate distance, the top LED illuminates primarily the top half (D) of the mucosa while light emitted from the side of the CPC primarily illuminates the bottom half (C). If the mucosa is farther away, the top LED effectively illuminates the entire FOV (I, J, K).

In some embodiments, the lower LEDs 217 (FIG. 2E) do shine light on objects within the capsule, such as parts of the camera, whose mirror images are within the FOV. To minimize ghost images, these objects have low reflectivity. Also, the angle of reflection from these objects is controlled by making the surfaces specular and choosing their angles relative to incident light appropriately. In several embodiments, these strategies reduce but not eliminate ghosting. Thus, certain embodiments limit the intensity of the lower (also called "bottom") LEDs 217. As the mucosa moves further from the endoscope, more illumination light is provided. However, the additional light is provided from the top LEDs 205 which direct all of their light outside the capsule 200. The illumination, and hence image exposure, is controlled by varying the intensity of the LEDs 205 and 217 in an attempt to make illumination uniform as described below. The flux from the bottom LEDs 217 is limited in some embodiments to a maximum value that provides sufficient illumination when the mucosa is close but not so high as to produce objectionable ghosting.

Numerous modifications and adaptations of the embodiments described herein will become apparent to the skilled artisan in view of this disclosure.

For example, although some embodiments of the invention use radial illumination, other embodiments use longitudinal illumination with two light sources that are mounted adjacent to a dome-shaped end to provide illumination in a longitudinal direction. Specifically, an endoscope 1900 has a dome-shaped end 1903 through which illumination is provided by a first set of LEDs (e.g. four LEDs) mounted in a common plane (perpendicular to a longitudinal axis) and labeled as "LED A" in FIG. 19. The first set of LEDs A are used to provide short-range illumination when tissue is close to or in contact with endoscope 1900. In the embodiment of FIG. 19, endoscope 1900 has a second set of LEDs (e.g. four LEDs) which are labeled as "LED B" in FIG. 19. The second set of LEDs B are used to provide long-range illumination when tissue is at an intermediate distance or even far away, at a predefined outer limit of the endoscope. Hence, depending on the distance between tissue to be imaged and endoscope 1900, the first set of LEDs A is used by itself or in combination with the second set of LEDs B (as illustrated in FIGS. 2I, 2J and 2K) to provide illumination necessary to generate diagnosable images in endoscope 1900.

In the embodiment illustrated in FIG. 19, light from the first set of LEDs A exits dome-shaped end 1903 longitudinally (rather than laterally as noted above for other embodiments) via an aperture 1905 defined by a cylindrical wall 1901. Wall 1901 surrounds LEDs A so that light from the first set is directed out of aperture 1905. Moreover, LEDs B are mounted farther away (in radial distance from a longitudinal axis of endoscope 1900) than LEDs A. In the embodiment illustrated in FIG. 19, LEDs B surround the wall 1901 and are mounted facing a diffuser 1902. Diffuser 1902 may be, for example, a Fresnel optic, hologram or other optical element that diffuses the light from LED B. Accordingly, endoscope 1900 uses LEDs A primarily to illuminate close and distant objects and uses LEDs B primarily to illuminate distant objects.

Moreover, instead of light other embodiments use electromagnetic radiation that is invisible to the human eye, e.g. ultra-violet or infra-red ranges. Hence, numerous modifications and adaptations of the embodiments described herein are encompassed by the scope of the invention.

Figure 25:
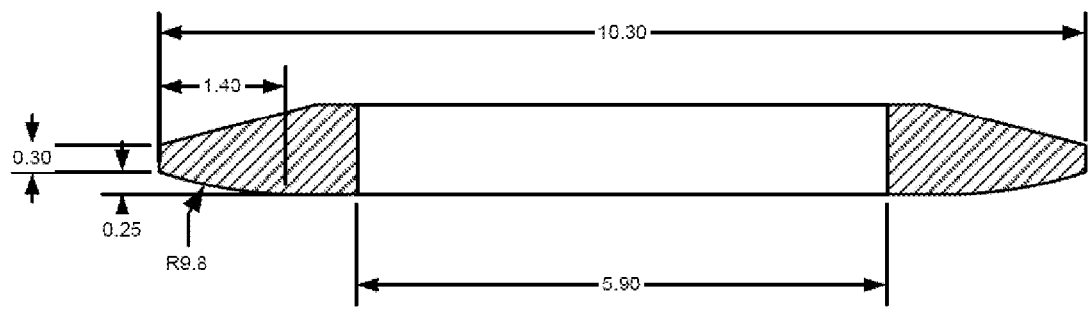
FIG. 25 illustrates dimensions of an exemplary annular mirror 218 having a convex reflecting surface in some embodiments of the invention.
Figure 26:
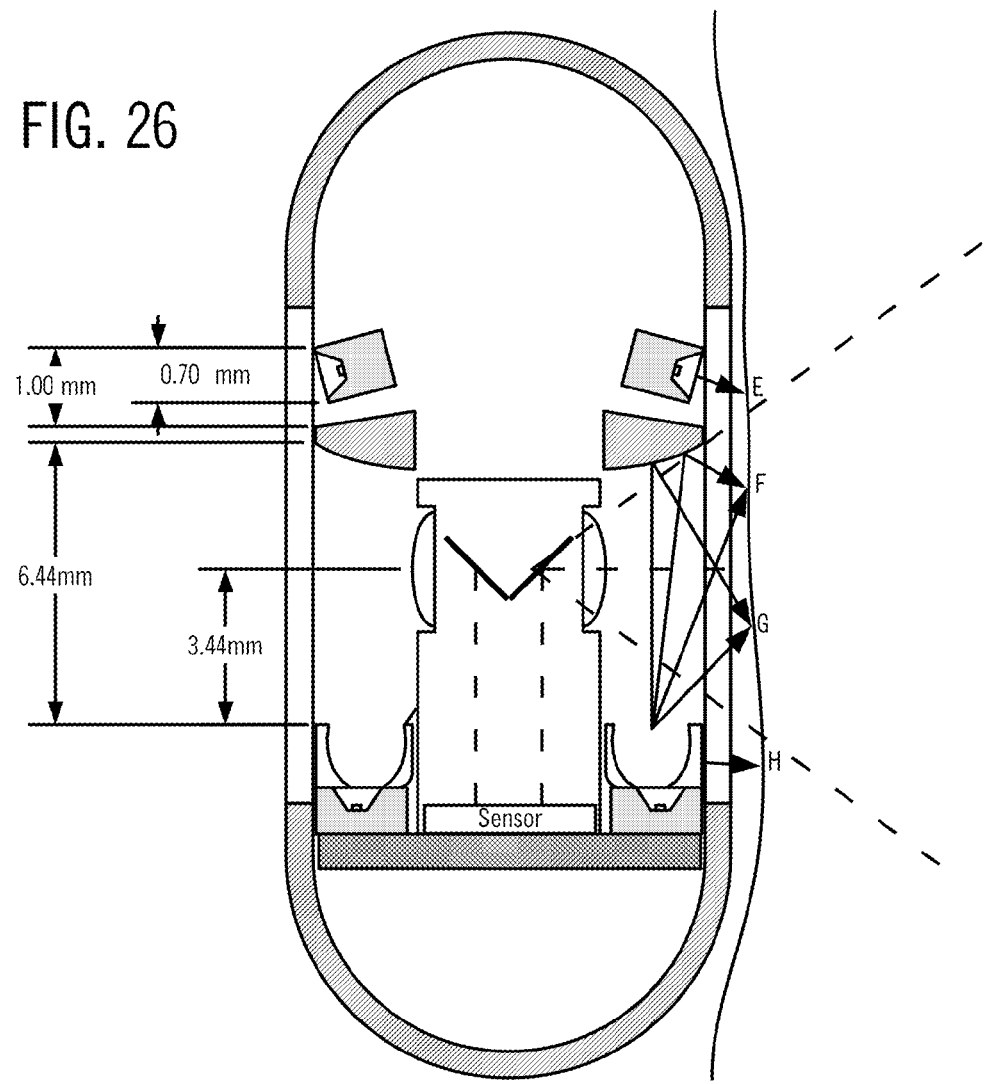
FIG. 26 illustrates dimensions of an endoscope shaped as a capsule in some embodiments of the invention.

FIG. 25 illustrates dimensions, in millimeters, of an exemplary annular mirror 218 having a convex reflecting surface in some embodiments of the invention. Moreover, FIG. 26 also illustrates dimensions, in millimeters, of an endoscope shaped as a capsule in some embodiments of the invention, which contain the annular mirror 218 of FIG. 25.

Referring to FIG. 13, an aperture A3 of lead frame 1300 is located only partially under input aperture A1 of the CPC 1100. CPC 1100 has an additional input aperture A5 ("second input aperture"), which is in addition to the above-discussed input aperture A1 ("first input aperture"). Apertures A1 and A5 together form an input aperture A4 through which all light is received by CPC 1100 from LED 1409. Specifically, rays 1301 and 1302 from LED 1409 enter CPC 1100 via the second input aperture A5 through surface 1208 of CPC 1100. Ray 1301 is refracted within sidewall 1105 of CPC 1100 on entry at surface 1208 and then reflected by a layer 1309 formed on sidewall 1105. The layer 1309 has two surfaces, namely a convex surface 1309X which is formed on sidewall 1105 located opposite to outer surface 1111, and a concave surface which forms an inside surface 1105R of CPC 1100.

More specifically, as shown in FIG. 13, surfaces 1309X and 1105R are two sides of a layer 1309 that constitutes a portion of CPC 1100, in addition to sidewall 1105. In one illustrative example, surfaces 1309X and 1105R of layer 1309 are within 100 microns of each other, i.e. the layer 1309 is 100 microns thick. Surface 1309X of layer 1309 (shown as a heavy black line in FIG. 13) reflects at least some of the incident illumination towards outer surface 1111, as illustrated by reflection of ray 1301 at point 1321. Note that CPC 1100 additionally includes another layer 1399 (shown in FIG. 13 as another heavy black line) whose concave surface forms another inside surface 1106R. Depending on the embodiment, either or both of layers 1309 and 1399 may be formed as either (a) a single metal layer (e.g. aluminum or silver) or (b) a multi-layered stack of dielectric layer(s) and/or metal layer(s).

Illumination from LED 1409 which is incident from within sidewall 1105, on outer surface 1111 (FIG. 13) diffuses out from CPC 1100 through an output aperture A6 as light portions 1311 and 1312, e.g. respectively resulting from rays 1301 and 1302. Specifically, as shown in FIG. 13, a ray 1302 also enters sidewall 1105 via the second input aperture A5, although its angle of incidence and its angle of refraction, are of such values that this ray 1302 is not reflected by surface 1105R of reflective layer 1309. Instead, ray 1302 is refracted at surface 1208 and is transmitted to and directly incident on surface 1111 at output aperture A6 without reflection, and thereafter diffuses out of sidewall 1105 as shown in FIG. 13 as light portion 1312. Accordingly, two light portions 1311 and 1312 are redirected towards aperture A6 by refraction and either direct transmission or transmission and reflection by CPC 1100, so as to be incident on bottom spot 210C in FIG. 2B (see intensity distribution 219C in FIG. 2E) which constitutes one fraction formed by beam 208C (FIG. 2D). As noted above, bottom spot 210C has area less than 50% of the total area of short-range illumination region 210 of a capsule endoscope 200.

As noted above, one light portion 1311 (FIG. 13) is included in a portion of the light fraction ("first fraction") emitted by LED 1409 that is reflected by surface 1309X of the layer 1309. Another surface 1105R of layer 1309 receives a portion of another fraction ("second fraction") of light emitted by LED 1409 which enters first input aperture A1 (illustrated by ray 1303). Surface 1105R reflects most of this portion through output aperture A2, towards another optical element, namely mirror 218 as illustrated by ray 1313 (see FIG. 13). Accordingly, CPC 1100 of FIG. 13 has two output apertures namely apertures A2 and A6, and these two output apertures are oriented laterally relative to one another (e.g. oriented at 90 degrees).

Note that in the embodiment illustrated in FIG. 13, another portion of a second light fraction from LED 1409 which enters the CPC 1100 at first input aperture Al, is illustrated by a ray 1304 that reaches another inside surface 1106R of another reflective layer 1399 of CPC 1100. Light reflected by inside surface 1106R also exits the CPC 1100 through output aperture A2, e.g. as shown by ray 1314. Depending on the angle of incidence, ray 1314 may be reflected by surface 1106R at such a small angle relative to a longitudinal axis of the endoscope that this ray 1314 also reaches mirror 218. Mirror 218 may also receive another portion of the second light fraction that is transmitted through CPC 1100 without reflection, as illustrated by ray 1316. As noted above, rays reaching mirror 218 from aperture A2 constitute a beam 208B which is reflected by mirror 218 toward a top spot 210B as shown in FIG. 2B (see intensity distribution 219A in FIG. 2E).

Depending on an offset distance 1398 between LED 1409 and CPC 1100 (e.g. measured from a center of the CPC cross-section), a third light fraction as illustrated by ray 1319 is reflected by surface 1106R at an angle sufficient large relative to the longitudinal axis such that the ray directly exits the endoscope without reflection, e.g. via a middle spot 210A of illumination region 210 in FIG. 2C (see intensity distribution 219B in FIG. 2E). Also included in the third light fraction is another ray 1315 which is also directly transmitted through CPC 1100 without reflection therein. As noted above, the third light fraction forms a beam 208A which exits the endoscope housing at a middle spot 210A.

Note that the offset distance 1398 shown in FIG. 13 determines the relative proportion of light transmitted through the two input apertures of the CPC, specifically A1 and A5. If offset distance 1398 is increased then the amount of light through input aperture A5 increase relative to input aperture A1. Depending on the embodiment, offset distance 1398 can be a predetermined fraction (e.g. two-thirds, half, one-third, or even one-fifth) of the width of input aperture A1. In one illustrative embodiment, offset distance 1398 is one half of width of input aperture A1 which results in about one half of light from the LED 1409 entering aperture A5 and exiting sidewall 1105 through a non-imaging region of the housing, e.g. region 210C and another half of the light entering aperture A1 and exiting through an imaging region 212 of the housing (see FIG. 2A).

In embodiments of the type illustrated in FIG. 13, LED 1409 and a phosphor in epoxy within cavity 1403 together form a source of light, wherein all light from this source is emitted on one side (e.g. bottom side) of a plane 1397. Note that CPC 1100 (which is an optical element) is located on the other side (e.g. top side) of the plane 1397. Additionally, as illustrated in FIG. 14, this source includes a pair of terminals represented by cathode lead 1411 and anode lead 1412 and a current passing therebetween causes the light emitting diode to generate light. As a portion of the generated light directly emerges from aperture A3 (FIG. 13), LED 1409 is an emitter for this portion. Another portion of the generated light is incident on the phosphor which absorbs the incident light and uses the energy therefrom to generate light in a different wavelength, and hence the phosphor is another emitter. Note that although a short-range illumination source is illustrated in FIGS. 13 and 14, in some embodiments both types of sources (long-range and short-range) 205 and 206 that are enclosed within a housing of an endoscope are identical to one another. Specifically, multiple copies of the same LED are used as a long-range source 205 and also as a short-range source 206.

Figure 4:
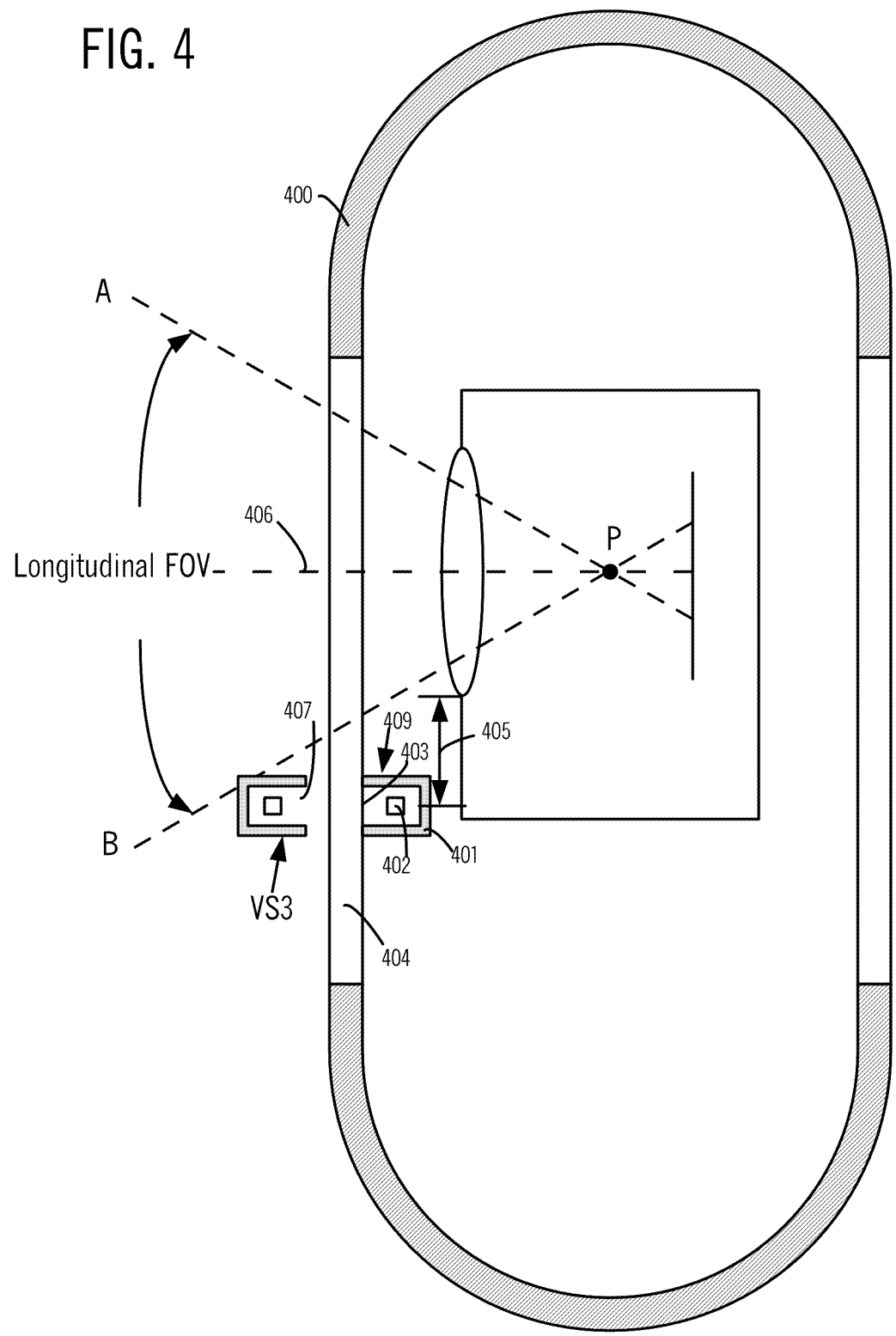

Referring to FIGS. 4 and 5 as described above, only one virtual source is illustrated in each figure to aid in conceptual understanding. In capsule endoscopes of most embodiments, there are at least two virtual sources as shown in FIG. 3. Specifically, reflections from an inner surface (not labeled in FIG. 4) and from an external surface (also not labeled) of window 404 result in two virtual sources, of which only a virtual source formed by reflection from the external surface of the endoscope's window is shown in FIG. 4. Similarly, there are two reflections from the two surfaces of window 503, of which only a reflection by the external surface is shown in FIG. 5.

Figure 27:
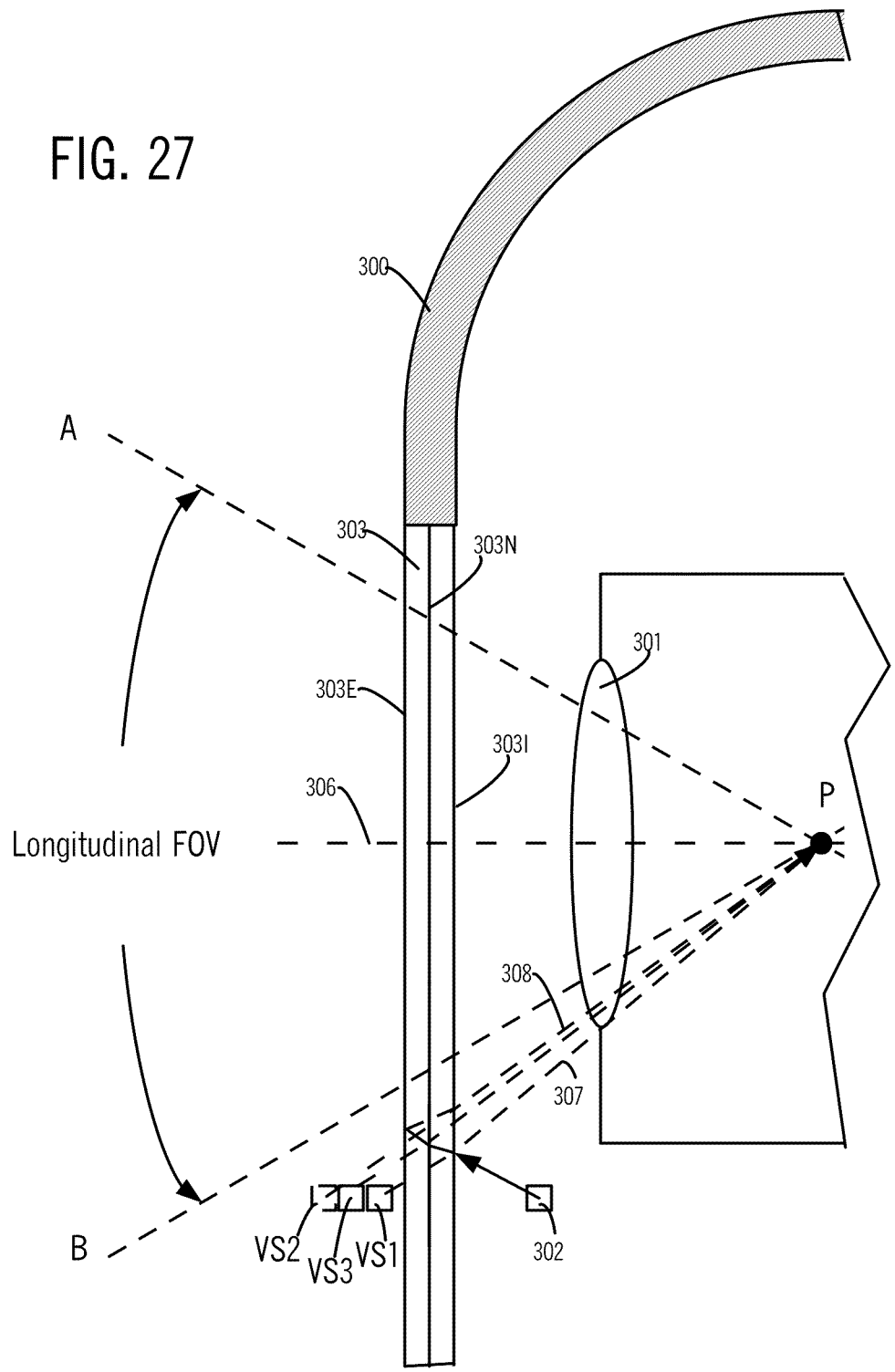
FIG. 27 illustrates, in a partial cross-sectional view, formation of three virtual sources by a two-layer window in some embodiments of a capsule endoscope in accordance with the invention.

Hence, the number of virtual sources formed by a corresponding number of reflections from a capsule endoscope's window in turn corresponds to the number of surfaces in the window. Specifically, in several embodiments a window in fact includes multiple interfaces (e.g. 3 interfaces as illustrated in FIG. 27), in which case orientation of the multiple interfaces and materials used to form layers in the endoscope's window determine the actual paths of transmitted and reflected rays resulting from an illumination ray. In the illustration of FIG. 27, a ray originating from source 302 is reflected at each of surfaces 303I, 303E and 303N, and such reflections form three virtual sources VS1, VS2 and VS3.

Figure 28A:
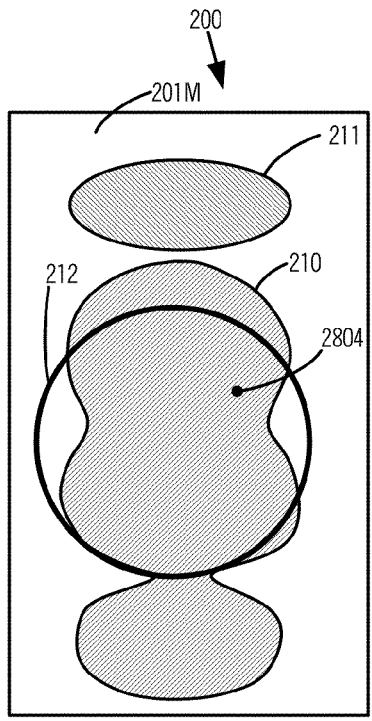
FIG. 28A-28D illustrate in a front view, relative positions of a long-range illumination region 211, a short-range illumination region 210 and an imaging region 212 on a window of a capsule endoscope in some embodiments of the invention.

Accordingly, in several embodiments, illumination regions 210 and 211 and imaging region 212 (illustrated in FIGS. 2A and 28A) are all formed on an inner surface of the housing of endoscope 200. In other embodiments all these regions 210-

212 are formed on an outer surface of the housing of endoscope 200. And in still other embodiments all these regions 210-212 are formed on an intermediate surface (i.e. an interface) within the housing of endoscope 200.

Regardless of the number of surfaces of a window in a capsule endoscope of some embodiments, imaging of the corresponding virtual sources in the camera is avoided by one or more of the above-described methods, e.g. by positioning the source sufficiently spaced apart (in the longitudinal direction) from the optical axis of the camera as illustrated in FIG. 3 or by shielding as illustrated in FIGS. 4 and 5. Furthermore, note that although only a single light source is illustrated in each of FIGS. 3-5 and 28, several embodiments use multiple light sources and imaging of their respective virtual sources is also avoided or minimized as described above.

Moreover, similar to FIG. 2C discussed above, FIG. 28A illustrates wall 201M of capsule-shaped endoscope 200 of some embodiments having an imaging region 212 overlapping a short-range illumination region 210 through which light is emitted from endoscope 200 for short-range illumination. Wall 201M in FIG. 28A also has a long-range illumination region 211 through which light is emitted from endoscope 200 for long-range illumination. Note that in FIG. 28A, imaging region 212 does not overlap the long-range illumination region 211. The just-described absence of overlap between imaging region 212 and long-range illumination region 211 enables operation of a long-range illumination source at a significantly higher intensity (e.g. an order of magnitude higher) relative to the intensity of a short-range illumination source, without resulting in an unduly bright region within the image formed within a camera of endoscope 200, which is in contrast to capture of point 2805 shown in FIGS. 28B and 28D (discussed below).

Figure 28B:
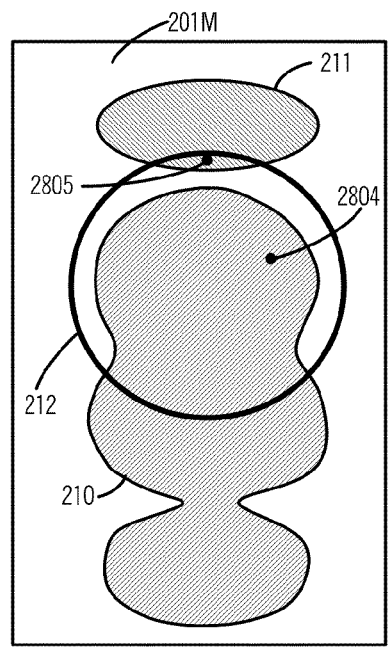
Figure 28C:
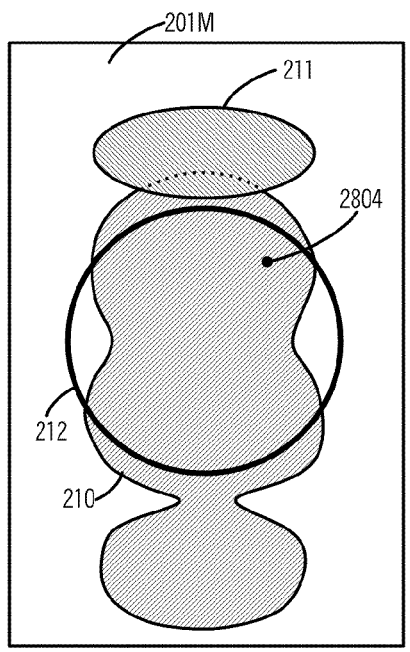
Figure 28D:
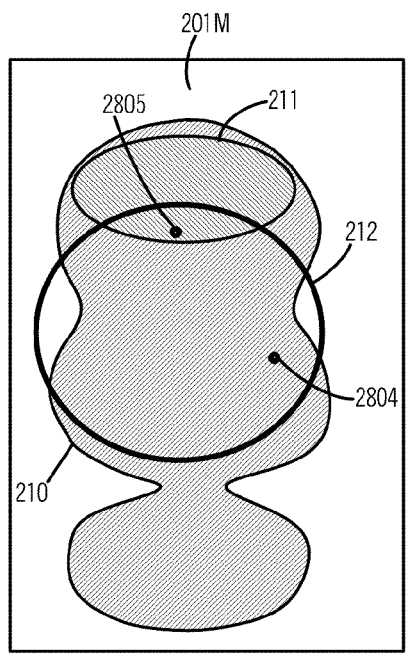

In certain alternative embodiments, imaging region 212 overlaps long-range illumination region 211, as illustrated by point 2805 in FIGS. 28B and 28D. In several such embodiments, there is no overlap between the short-range illumination region 210 and the long-range illumination region 211 (FIG. 2B). In these embodiments, imaging region 212 (FIG. 2B) also contains a point 2804 that lies in short-range illumination region 210 but does not lie in the long-range illumination region 211. Point 2804 can be any point in the imaging region 212, e.g. an intersection of an optical axis of the camera with an outer surface of the housing. In some embodiments, all three regions 210, 211 and 212 overlap one another as illustrated by point 2805 in FIG. 28D. Note that overlap of the type illustrated in FIGS. 28B and 28D typically results in an exceptionally bright region in an image, and the bright region is cropped as discussed above, and in the next paragraph. Note that embodiments that use other types of cameras (such as a panoramic camera) also satisfy one or more of the above-described relationship, e.g. see point 2804 in FIGS. 31 and 32.

In several embodiments of the type shown in FIG. 28B, an image formed within the camera includes an unduly bright region, caused by reflection of that fraction of light exiting the endoscope which originates in a long-range illumination source. Hence, in some embodiments of the type shown in FIG. 28B, image data representing a diagnosable image at a specific location in a gastrointestinal tract is obtained by excluding (i.e. discarding) certain data ("additional data") which represents the unduly bright region. Specifically, depending on the embodiment, a diagnosable image can be generated in different ways, such as (a) inherent cropping by appropriate design of hardware within the endoscope's camera e.g. by including therein a sensor sized and positioned appropriately to not sense the additional data and/or (b) cropping performed by appropriately programming firmware and/or software executed by a processor included within endoscope 200, and/or (c) cropping performed by imaging application software executed by an external computer that receives a combination of image data and additional data from the transmitter (such as Microsoft® Office Picture Manager available from Microsoft Corporation), to generate image data (by excluding the additional data), store the image data in the computer's memory, and display a diagnosable image to a physician (e.g. a gastroenterologist) for use in diagnosing diseases.

The just-described cropping is not required if positions of the two sources relative to the camera are such that imaging region 212 does not overlap the long-range illumination region 211 as noted above in reference to FIG. 28A. Note that the just-described lack of overlap is further illustrated in other embodiments of the type shown in FIG. 28C wherein short-range illumination region 210 overlaps the long-range illumination region 211. In the embodiments of FIG. 28C, imaging region 212 contains point 2804 that lies in short-range illumination region 210 but does not lie in long-range illumination region 211. Moreover, certain embodiments that perform cropping as described above have the two illumination regions and the imaging region, i.e. all three regions overlap one another as shown in FIG. 28D. As noted above, in embodiments of the type illustrated in FIG. 28D, point 2805 is located within each of the three regions 210, 211 and 212. Note that in the embodiments of FIGS. 28D and 28A, imaging region 212 contains point 2804 that lies in short-range illumination region 210 but does not lie in long-range illumination region 211. Note that the just-described condition is satisfied in each of the four types of embodiments illustrated in FIGS. 28A-28D.

Figure 28E:
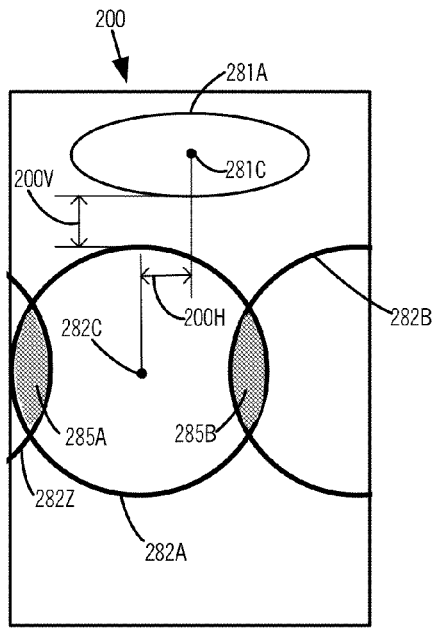
FIGS. 28E and 28G illustrate overlap of a pair of adjacent imaging regions 282A and 282B with one another, and additionally another overlap of another pair of adjacent imaging regions 282Z and 282A with one another, in a capsule endoscope of the type illustrated in FIGS. 28A and 28C respectively.
Figure 28F:
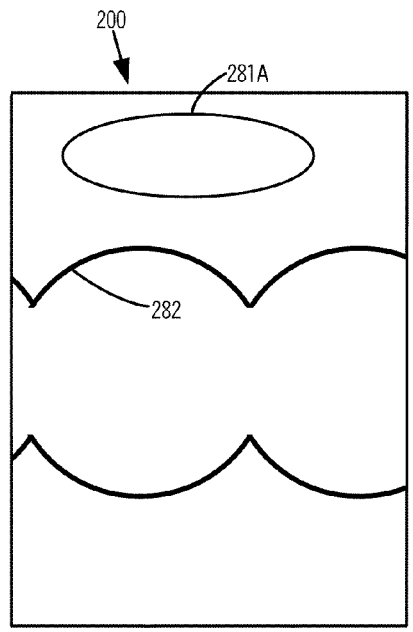
FIGS. 28F and 28H illustrates a union 282 of adjacent imaging regions in a capsule endoscope of the type illustrated in FIGS. 28E and 28G respectively.

In some embodiments, a number of imaging regions that are adjacent, overlap each other, as illustrated by overlap regions 285A and 285B in FIG. 28E. Specifically, overlap region 285A results from overlap of the two adjacent imaging regions 282A and 282Z, and overlap region 285B results from overlap of the two adjacent imaging regions 282A and 282B. As noted elsewhere herein, a set of sensors (e.g. two sensors 3401 and 3402 illustrated in FIG. 34) are located within a central region of endoscope 200, and each sensor in the set receives and forms a portion of an image of light reflected by tissue and reaching a corresponding one of the respective imaging regions 282A-282Z shown in FIG. 28E. Hence, in several embodiments, data generated by a set of sensors is supplied in whole or in part (after optional cropping by a processor) to a transmitter that in turn transmits image data representing a diagnosable image to an external device.

Figure 20:
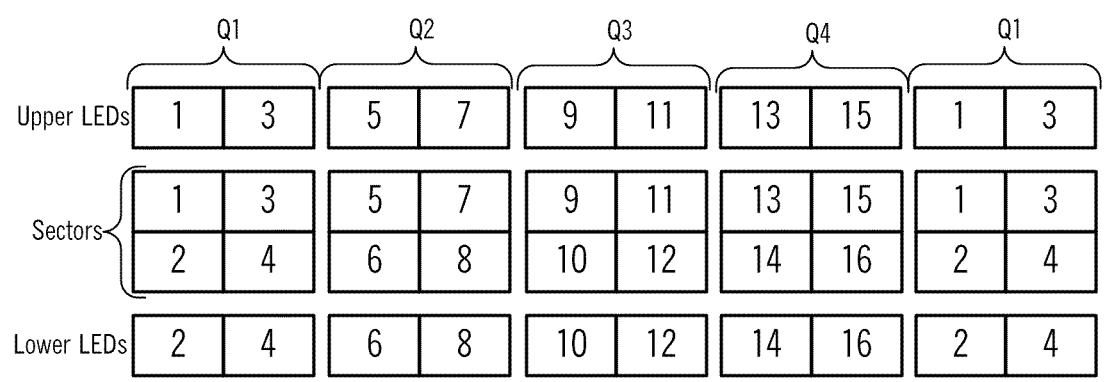
FIG. 20 illustrates, in a block diagram, the numbering of LEDs and the numbering of sectors of a sensor for use in an illumination control method of the type shown in FIG. 21.
Figure 21:
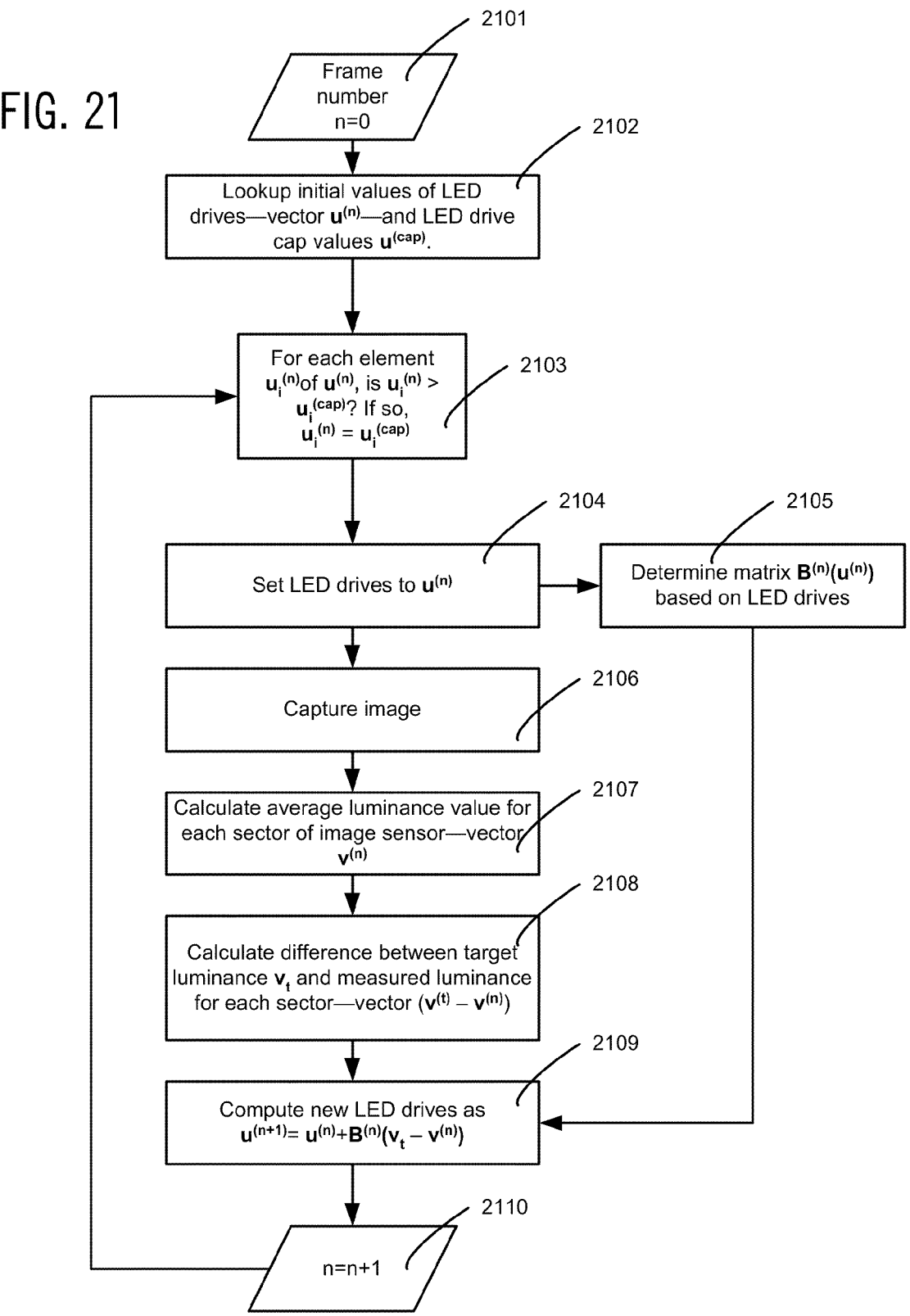
FIG. 21 illustrates, in a flow chart, a method used in some embodiments, to operate light emitters for panoramic illumination and imaging.

Note that although a set of two sensors is illustrated in FIG. 34 for some embodiments of an endoscope, other embodiments use fewer or more sensors in a set coupled to the transmitter (e.g. one embodiment uses a set of one sensor). In an illustrative embodiment, a sensor chip in an endoscope has a pixel array to record four portions of an image from four objectives in four regions thereof, as illustrated by Q1-Q4 in FIG. 2O and FIG. 20, and the sensor chip supplies the image data captured therein to a transmitter. As will be readily apparent to the skilled artisan in view of this disclosure, other embodiments do not use four regions of a single monolithic sensor chip as shown in FIG. 2O and FIG. 20 and instead use a set of four sensors, and image data resulting from operation of the set of four sensors at a single location is supplied to the transmitter for generation of a diagnosable image by an external computer.

In embodiments of the type illustrated in FIG. 28E, the light reaching overlap region 285A is sensed by two sensors for imaging regions 282Z and 282A respectively. Similarly, there are two sensors within endoscope 200 which receive light that has been reflected by tissue of the gastrointestinal tract and reaches overlap region 285B. Due to overlaps, a region 282 (FIG. 28F) formed by a union of all imaging regions 282A-282Z of an endoscope is a continuous band (i.e. union region 282) around the endoscope's tubular wall as illustrated in FIG. 28I. Accordingly, imaging region 282 of endoscope 200 is defined by an intersection of a surface (e.g. outer surface) of the housing with electromagnetic radiation ("imaging illumination") entering the housing and being captured in image data supplied by the set of sensors to a transmitter. As noted elsewhere herein, a computer that eventually receives the image data is appropriately programmed to generate therefrom a panoramic 3600 image that is displayed to a physician.

In embodiments of the type illustrated in FIG. 28E, ghosting is prevented by positioning a long-range illumination source within the endoscope housing such that a majority of light exiting the housing which originates from the long-range illumination source passes through a region 281A of the housing ("long-range illumination region"). Long-range illumination region 281A of such embodiments (FIG. 28E) does not overlap any of imaging regions 282A-282Z (and therefore does not overlap union region 282 of FIG. 28F). Specifically, in some embodiments, long-range illumination region 281A is separated (in the direction of the longitudinal axis of endoscope 200) from a corresponding imaging region 282A. Hence, in the embodiment of FIG. 28E, there is no overlap between regions 281A and 282A due to a vertical separation distance 200V therebetween, which has a positive value. Furthermore, note that regions 281A and 282A may be also offset in the circumferential direction. Specifically, in the embodiment shown in FIG. 28E, a center 282C of region 282A is separated by circumferential distance 200H from a center 281C of region 281.

Figure 28G:
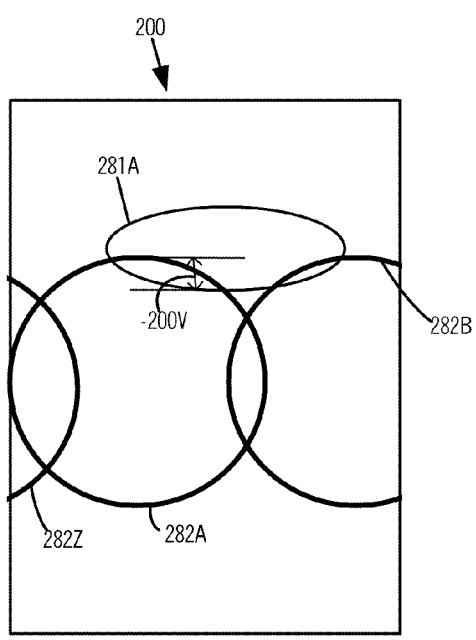
Figure 28H:
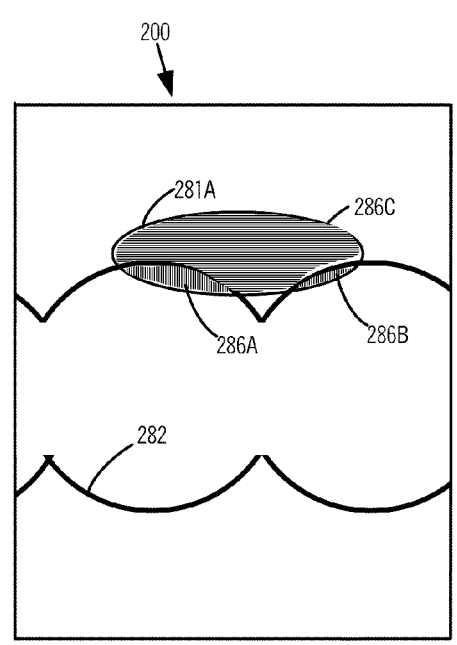
Figure 28I:
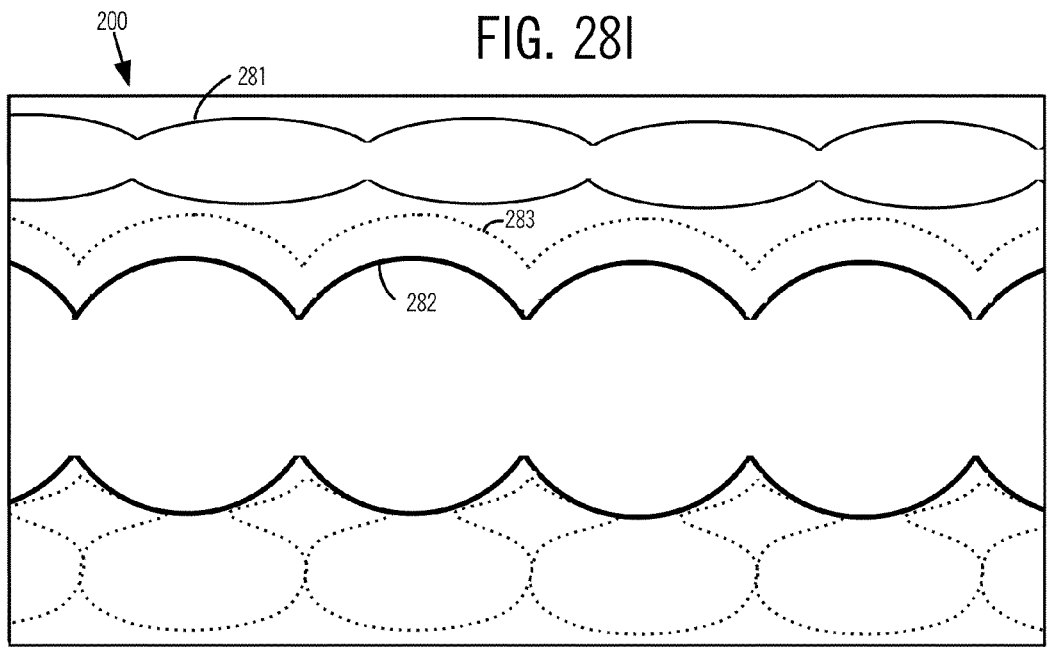
FIGS. 28I and 28J illustrate, on an unrolled tubular wall of a capsule endoscope of the type illustrated in FIGS. 28E-28F and 28G-28H respectively, the position of a union 282 of imaging regions relative to the position of another union 281 of adjacent short-range illumination regions.
Figure 28J:
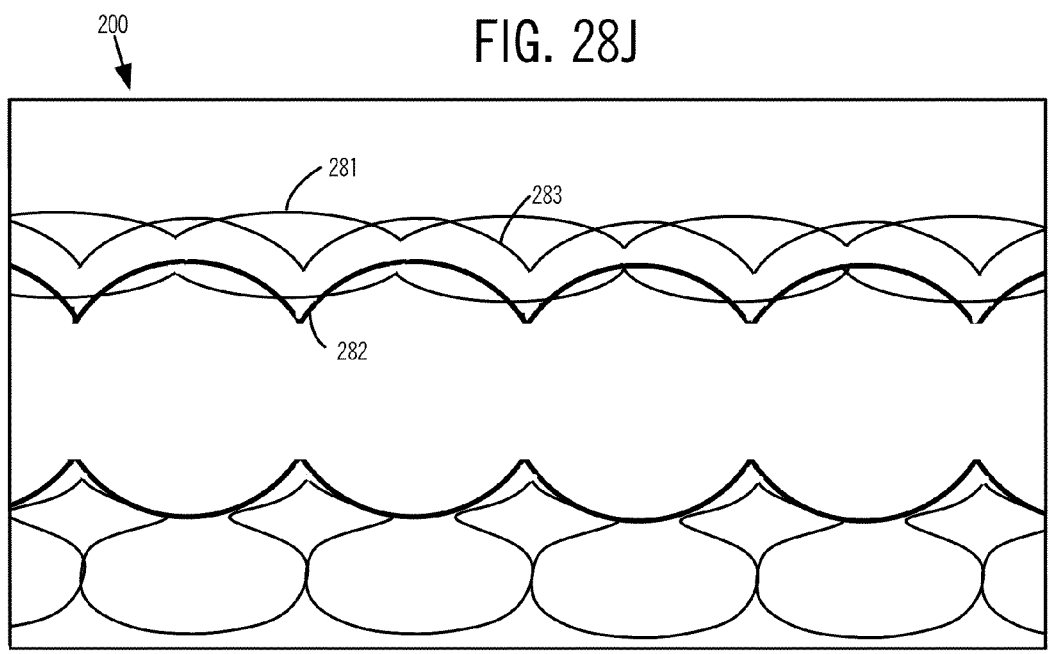

However, as illustrated in FIG. 28G, in many embodiments, due to constraints on the size of a capsule that is small enough to be swallowable, the vertical separation distance 200V has a negative value, which results in an overlap region 286A (FIG. 28H) between regions 281A and 282A. Due to a positive value for circumferential distance 200H (not labeled in FIG. 28G, see FIG. 28E), the long-range illumination region 281A also overlaps an adjacent imaging region 282B, as shown in FIG. 28H by the overlap region 286B. However, in other embodiments, circumferential distance 200H (FIG. 28E) is sufficiently small to eliminate any overlap between long-range illumination region 281A and adjacent imaging region 282B.

FIG. 28H shows a non-overlapping illumination region 286C which is a remainder of region 281A left by disregarding overlap regions 286A and 286B. Specifically, regions 286A, 286B and 286C together form long-range illumination region 281A. Overlap regions 286A and 286B (if any) are kept small, within conformance with space constraints of a swallowable capsule, to minimize ghosting resulting from light originating at the source, being reflected by an inner surface and reaching the camera(s) without ever exiting the capsule endoscope 200. Hence, several capsule endoscopes of the type described herein have at least 50% of (e.g. a majority of, or most of) light, which is emitted by a single long-range light source and which exits through long-range illumination region 281A actually exit capsule endoscope 200 through non-overlapping region 286C. Specifically, in several embodiments, non-overlapping region 286C is several times larger than overlap regions 286A and 286B.

In many embodiments, a majority of light, which exits endoscope 200 and originates in a long-range light source, does not exit through union region 282. To re-iterate, in some embodiments, the light, which exits through overlapping regions 286A and 286B, is less than 50% of light from any long-range light source that exits the housing to reach outside the endoscope 200. At least a portion of the just-described majority is incident on the gastrointestinal tract, gets reflected therefrom, and enters endoscope 200 through union region 282.

Note that in certain specific embodiments of capsule endoscope 200, wherein each long-range illumination region 281A is sufficiently aligned with a corresponding imaging region 282A, almost all of the light (e.g. 90% or more) which exits capsule endoscope 200 through long-range illumination region 281A is emitted by a single long-range light source corresponding thereto. Hence, in the just-described embodiments, only a negligible amount of stray light from other light sources (e.g. adjacent sources) within the capsule endoscope exits through each long-range illumination region.

Figure 28K:
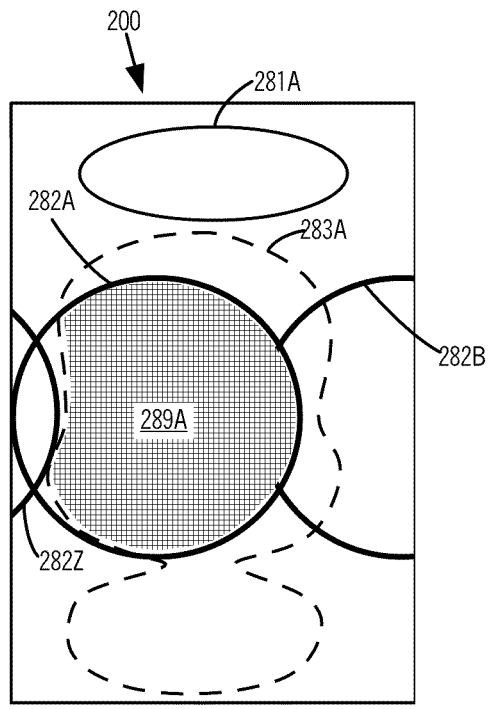
FIGS. 28K and 28L illustrate overlap of imaging region 282A with a corresponding short-range illumination region 283A, in a capsule endoscope of the type illustrated in FIGS. 28A and 28C respectively.
Figure 28L:
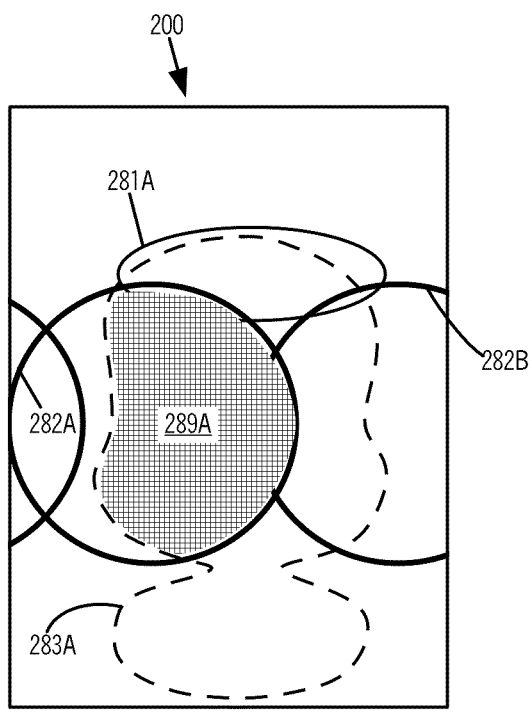

As noted above in reference to FIG. 2C, many embodiments of a capsule endoscope also have one or more short-range light illumination region(s) 210, which may correspond to (but are not necessarily aligned with) either or both of imaging region 212 and/or long-range illumination region 211, depending on the embodiment. Specifically, as shown in FIGS. 28K and 28L for embodiments that correspond to FIGS. 28E and 28G respectively described above, a short-range illumination region 283A overlaps imaging region 282A in overlap region 289A. Overlap region 289A has an area which constitutes more than 50% of the area of imaging region 282A.

Hence, more than 50% of light which exits some embodiments of a capsule endoscope through imaging region 282A, actually exits through overlap region 289A. Accordingly, in certain embodiments, at least 50% of light (e.g. a majority or most of light) emitted by a short-range light source and exiting the housing of a capsule endoscope, actually exits through union region 282. In several such embodiments, multiple short-range illumination regions also overlap one another, to form a continuous band 283 around the circumference of a tubular wall (which is shown unrolled for illustration purposes in FIGS. 28I and 28J, as noted above).

Furthermore, as shown in FIGS. 28A-28D, the area of a short-range illumination region 210 is typically several times e.g. 2 times, 3 times, 4 times or even 5 times larger than the area of a long-range illumination region 211. Also as illustrated in FIGS. 28K and 28L, the area of illumination region 283A is 3 or 4 times larger than the area of illumination region 281A. In several such embodiments, the two types of light sources included in a capsule endoscope, namely a short-range light source and a long-range light source, each include emitters that are identical to one another, i.e. the emitters are implemented using multiple copies of a single product (e.g. LED), and accordingly have the same ratings as one another. However, as noted above, the short-range light sources of a capsule endoscope in accordance with the invention include one or more optical devices to split light from the emitter therein, into multiple fractions and/or portions and/or parts that are initially redirected by the optical device(s) along different paths but finally brought together at the housing, to form an illumination region 210 which is several times larger than illumination region 211 formed by light incident directly on the housing from an emitter in a long-range light source.

Figure 29A:
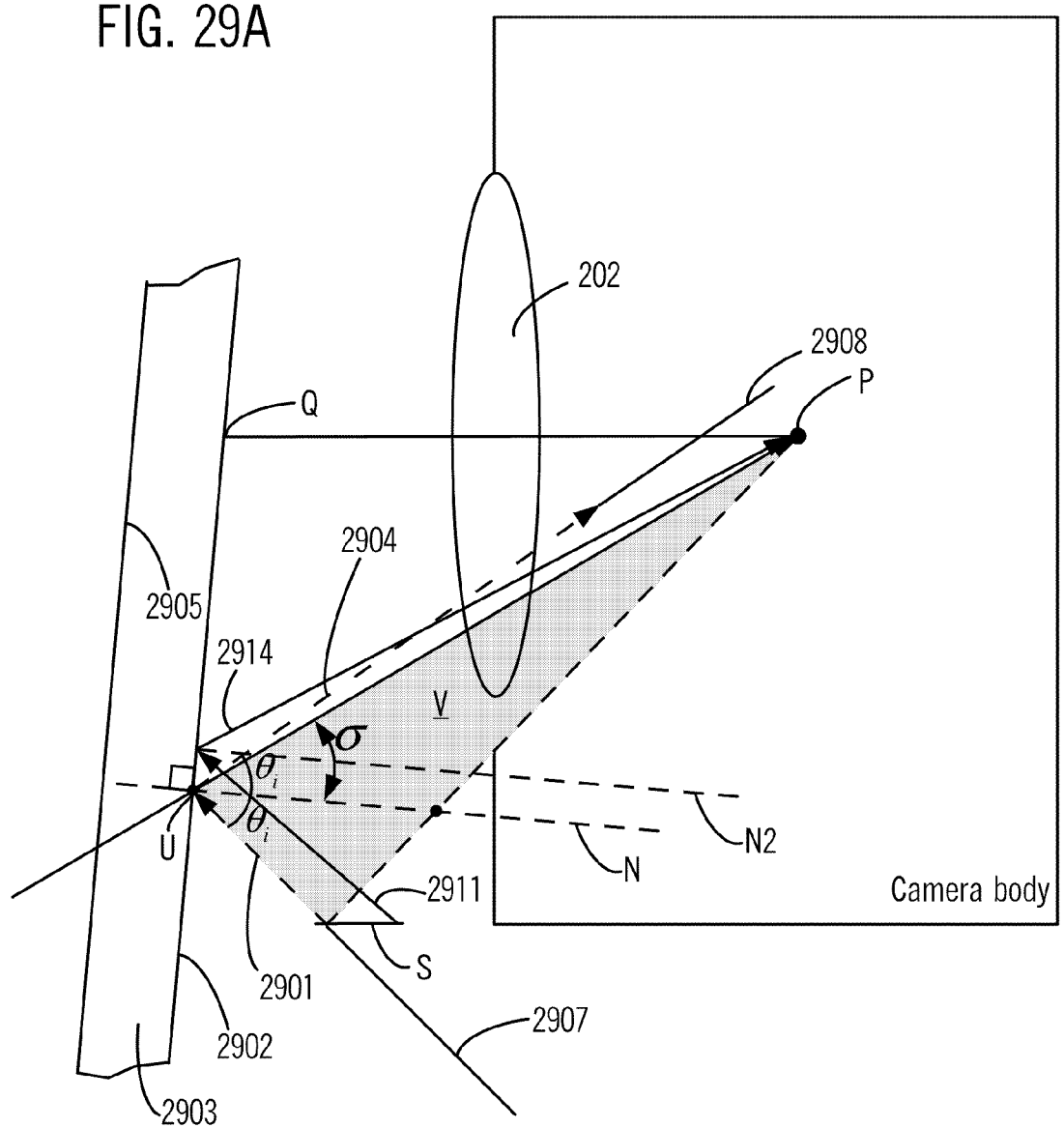
Figure 29B:
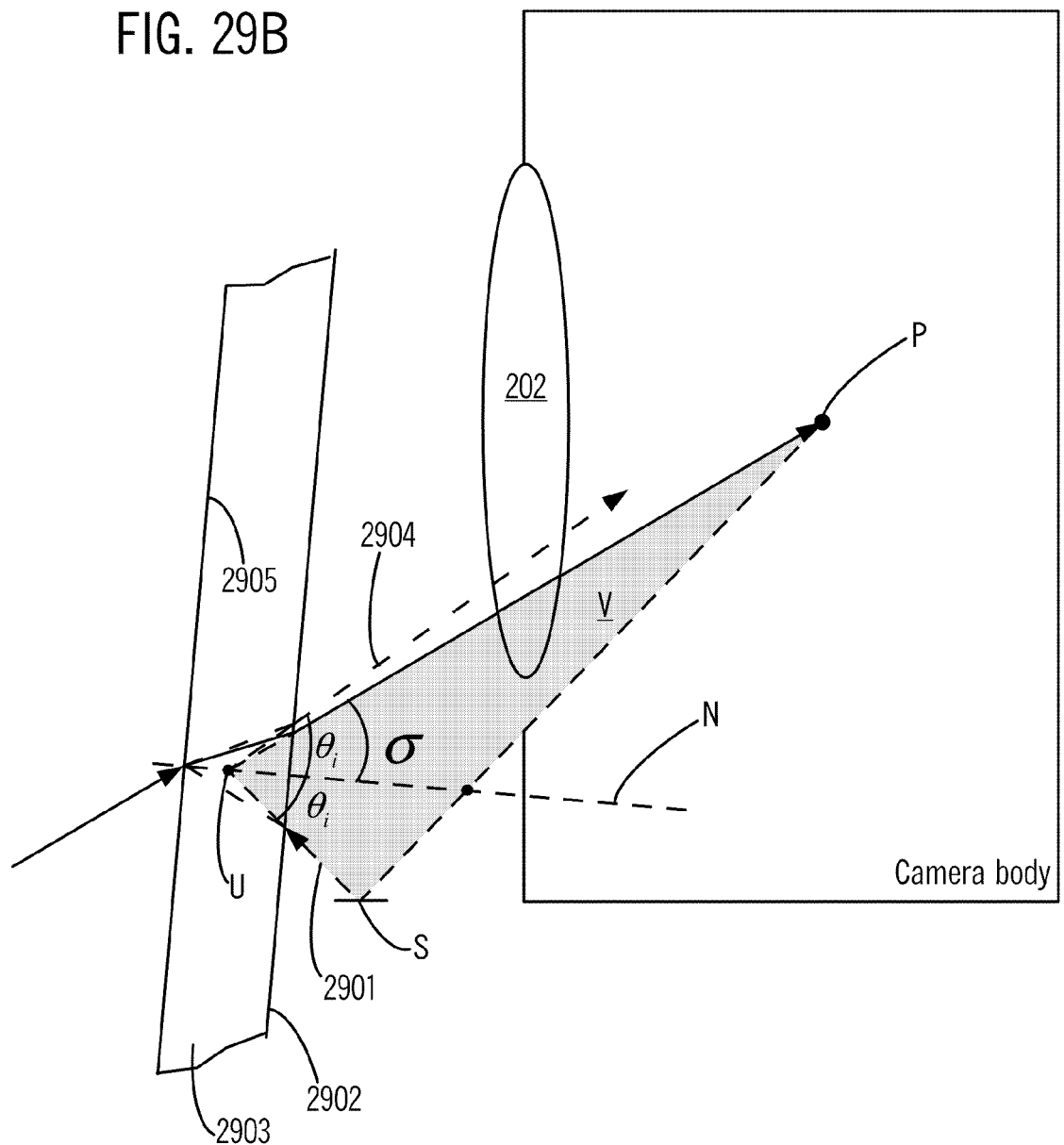

Several embodiments differ from the above-described embodiments illustrated in FIGS. 6 and 7, wherein several differences are illustrated in FIGS. 29A and 29B and/or described below. In embodiments of the type illustrated in FIGS. 29A and 29B, an illumination ray 2901 emitted from source aperture S is reflected from an inner surface 2902 of window 2903 in a tubular wall of the housing of the endoscope. Specifically, point U is at the intersection of the incident ray 2901 and the reflected ray 2904. In FIG. 29A, the ray 2901 is collinear with a line 2907 and reflects from inner surface 2902 at point U on inner surface 2902 to form reflected ray 2904 along a line 2908. Note that in FIG. 29A, V is a plane formed by the three points S, U and P where P is within the pupil of the camera. In some embodiments, plane V in FIGS. 29A and 29B is vertical, i.e. coincident with the plane of the paper in FIG. 29A, and therefore points U, P, S lie in plane V as do ray 2904 and normal line N.

Accordingly, in the just-described embodiments, plane V is a longitudinal plane coincident with the plane of the paper on which FIG. 29A is drawn. This longitudinal plane V passes through the above-described point U and through a point C, wherein C is the center of curvature of an arc AUB (FIG. 6). The just described lateral plane is parallel to the optical axis PQ (FIGS. 6 and 29A) and passes through the intersection point U. The lateral plane and the longitudinal plane are perpendicular to one another in embodiments of the type illustrated in FIG. 29A. In other embodiments, plane V is not vertical and instead points P and S in FIG. 29A are projections in a vertical plane that is coincident with the plane of the paper in which normal line N lies. Accordingly, the geometry shown in FIG. 29A is similar to the geometry shown in FIG. 6 except that in FIG. 29A, the angle of incidence of ray 2901 is $\theta_i$ whereas in FIG. 6 $\theta_i$ is the projection of the angle of incidence on to a vertical plane containing C and U, i.e. the vertical plane projection of ray SU in FIG. 6.

Referring to FIG. 29B, incident illumination ray 2901 is first refracted at the inner surface 2902 into window 2903, reflects from outer surface 2905 as ray 2906, and then refracts at inner surface 2902 to become reflected ray 2904. In FIG. 29B, point U is within the window 2903, and N is a line that bisects an angle formed by incident ray 2901 and reflected ray 2902. If inner surface 2902 and outer surface 2905 are parallel to one another, then line N is normal to both surfaces 2902 and 2905, at point U.

Referring to both FIGS. 29A and 29B, an angle of incidence of ray 2901 at inner surface 2902 is $\theta_i$ as discussed above. Also in both FIGS. 29A and 29B, illumination ray 2901 and line N together define the above-described plane V. In several embodiments, there exists a set of image forming rays entering the pupil P of an endoscope's camera within the field of view (FOV) which lie in plane V and which either pass through point U (FIG. 29A) or appear to pass through point U when viewed from inside the endoscope (FIG. 29B). Specifically, consider a ray UP going from point U to point P, with P within the pupil, that makes an angle σ with line N. The reflection of incident illumination ray 2901 intersects point P if $\theta_i = \sigma$.

Hence in several embodiments, the illumination rays from source S are restricted in angle such that $\theta_i > \sigma$ for a majority of pairs of rays (such as one pair 2901 and 2904, and another pair 2911 and 2914) in all planes V of FIGS. 29A and 29B, to reduce or eliminate a ghost of the source S (i.e. a virtual source) from an image captured by the camera. For example, in several embodiments source S is positioned, by experiment, at a location that is chosen to be at an angle $\theta_i$ relative to the optical axis of the camera, selected to be sufficiently larger than angle σ (e.g. 1° larger), so as to avoid ghosting in the geometry illustrated in FIGS. 25 and 26.

As described above, image data representing a diagnosable image is supplied to a transmitter of the endoscope. A transmitter as used herein includes a wireless transmitter (e.g. a device for sending electromagnetic waves that generates and modulates current, and conveys it to an antenna included therein for radio-frequency transmission or conveys it to a LED, laser, or other light source included therein for optical transmission) or a wireline transmitter (e.g. that includes output terminal(s) coupled to transistor(s) included therein to generate electrical signal(s) for transmission across one or more wires).

Hence a field of view 212 (FIGS. 2A and 29C) of the endoscope is a range of angles through which an image of the gastrointestinal tract is captured by at least one camera, optionally cropped and supplied to the transmitter. Therefore, in several embodiments of the invention, an endoscope's field of view 214 is effectively (an "effective field of view") smaller than a typical camera's field of view traditionally defined by lens 202's field of view 2993 (FIG. 29C) and also limited by sensor 232's size (thereby defining its own field of view 2992). As illustrated in FIG. 29C, a region 2994 of an image formed in a plane 2991 inside the camera is inherently cropped by the position and dimensions of sensor 232. Additionally, in embodiments of the type illustrated in FIG. 29C, a processor within the endoscope further discards another region 2995 in plane 2991 even though additional data representing region 2995 is captured by sensor 232. Accordingly, the endoscope's field of view 214 is defined by a region 2999 of the sensor wherein image data of a diagnosable image is generated.

Figure 30:
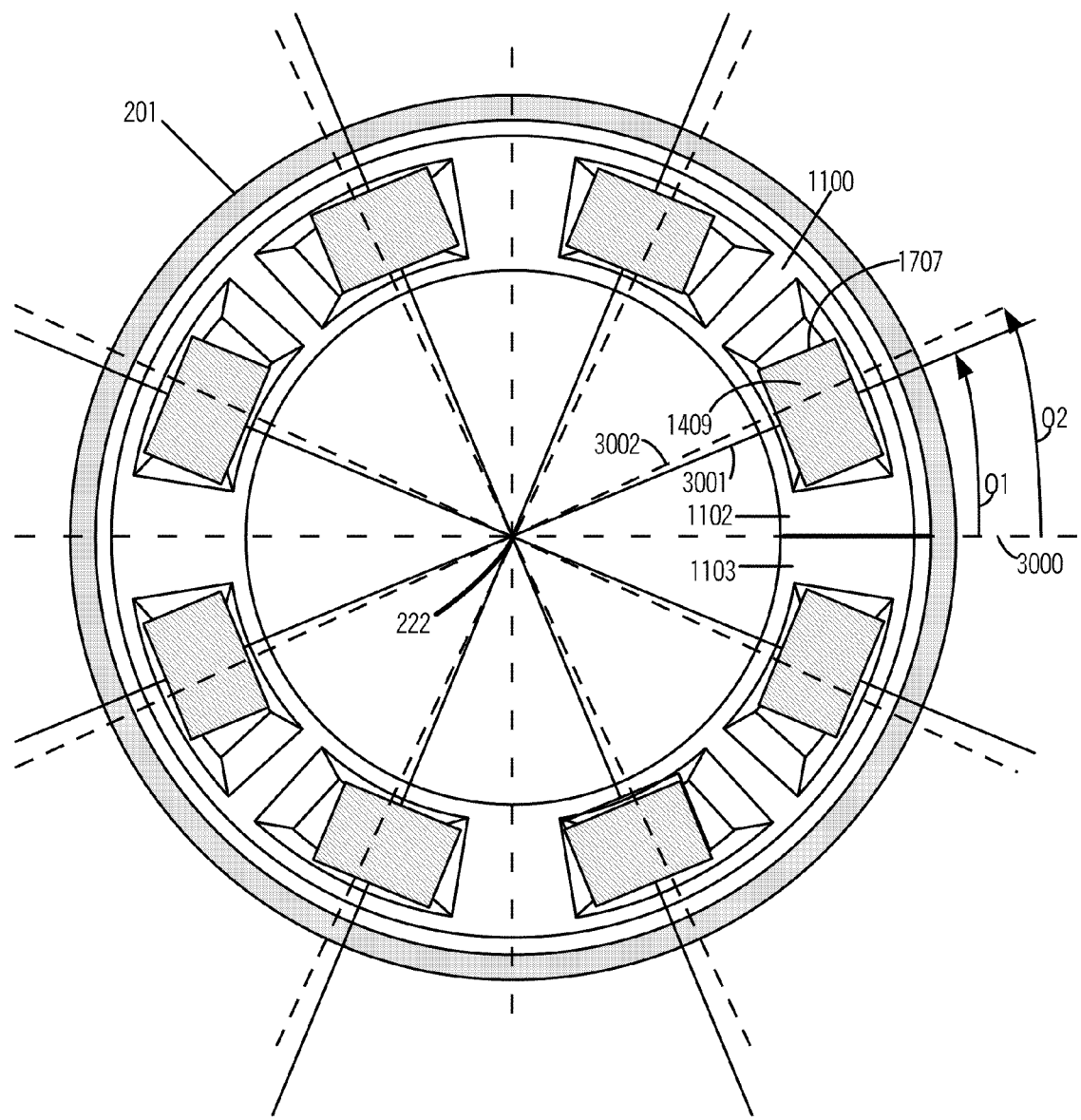
FIG. 30 illustrates, in a cross-sectional plan view, relative positions of long-range and short-range illumination sources in a capsule endoscope in some embodiments of the invention.

In several embodiments illustrated in FIG. 30, short-range source 206 (described above and shown in FIGS. 2A, 2D and 2E) is centered in a radial plane 3002 while long-range source 205 is centered in a different radial plane 3001. Planes 3001 and 3002 are radial relative to housing 201, i.e. each of these planes passes through the longitudinal axis 222 which is at the center of the cross-section of housing 201. Radial planes 3001 and 3002 make are at angles O1 and O2 respectively, relative to a plane 3000. Plane 3000 passes through seams 1103 and 1104 at which the two halves 1101 and 1102 of the optical element 1100 are glued to one another. Angles O2 and O1 may be same as or different from one another depending on the embodiment. In an illustrative embodiment, angle O2 is 25° and angle O1 is 22.5°. However, as will be apparent to the skilled artisan, different values of angles O2 and O1 are used in other embodiments, depending on the relative position of the compound parabolic concentrators formed within optical element 1100. The precise values of angles O2 and O1 in a specific embodiment may be determined by experiment and/or trial and error.

Figure 31:
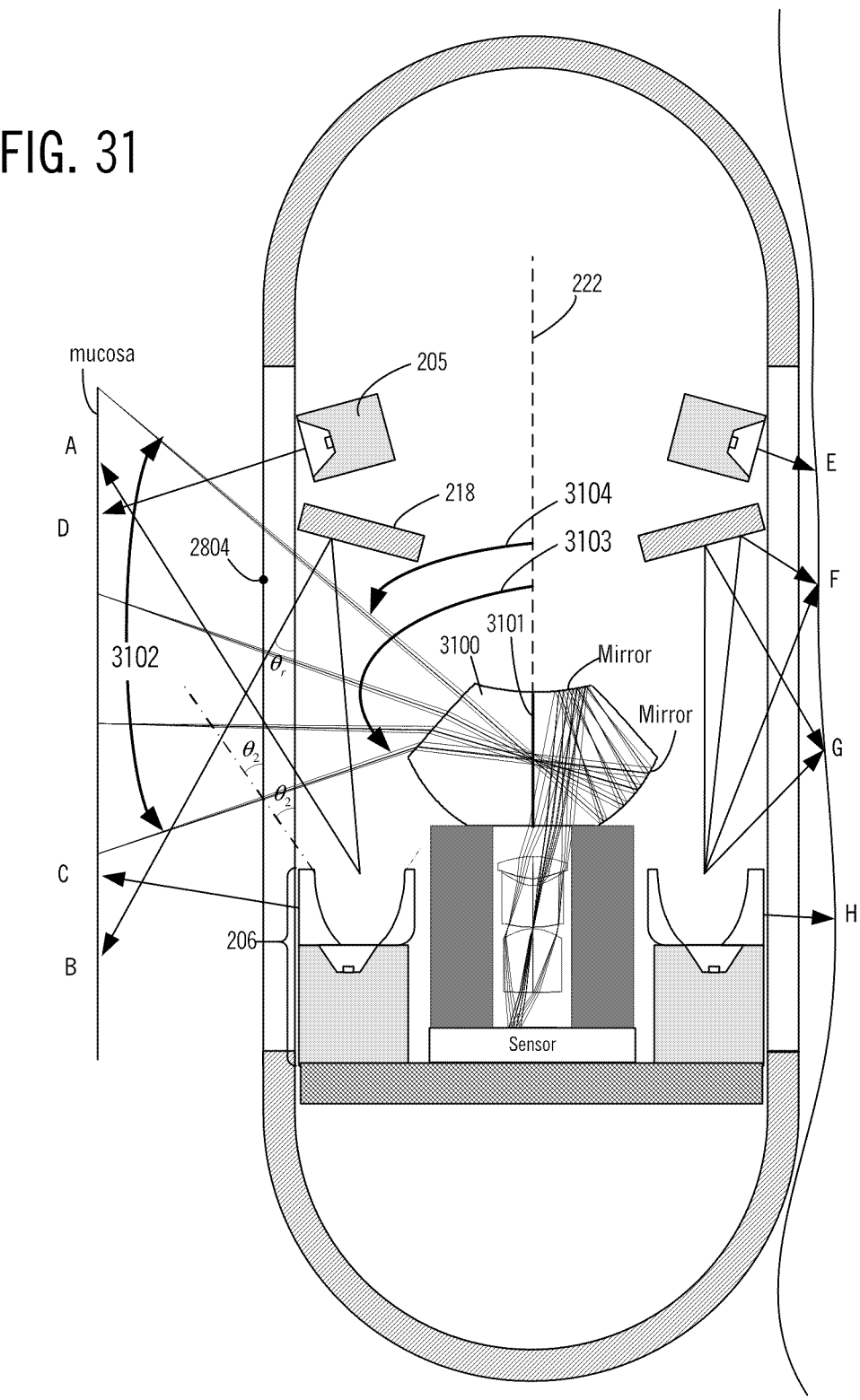
FIGS. 31 and 32 illustrate, in cross-sectional side views, two embodiments of a capsule endoscope in accordance with the invention, housing a radially-symmetric optical element in a camera.
Figure 32:
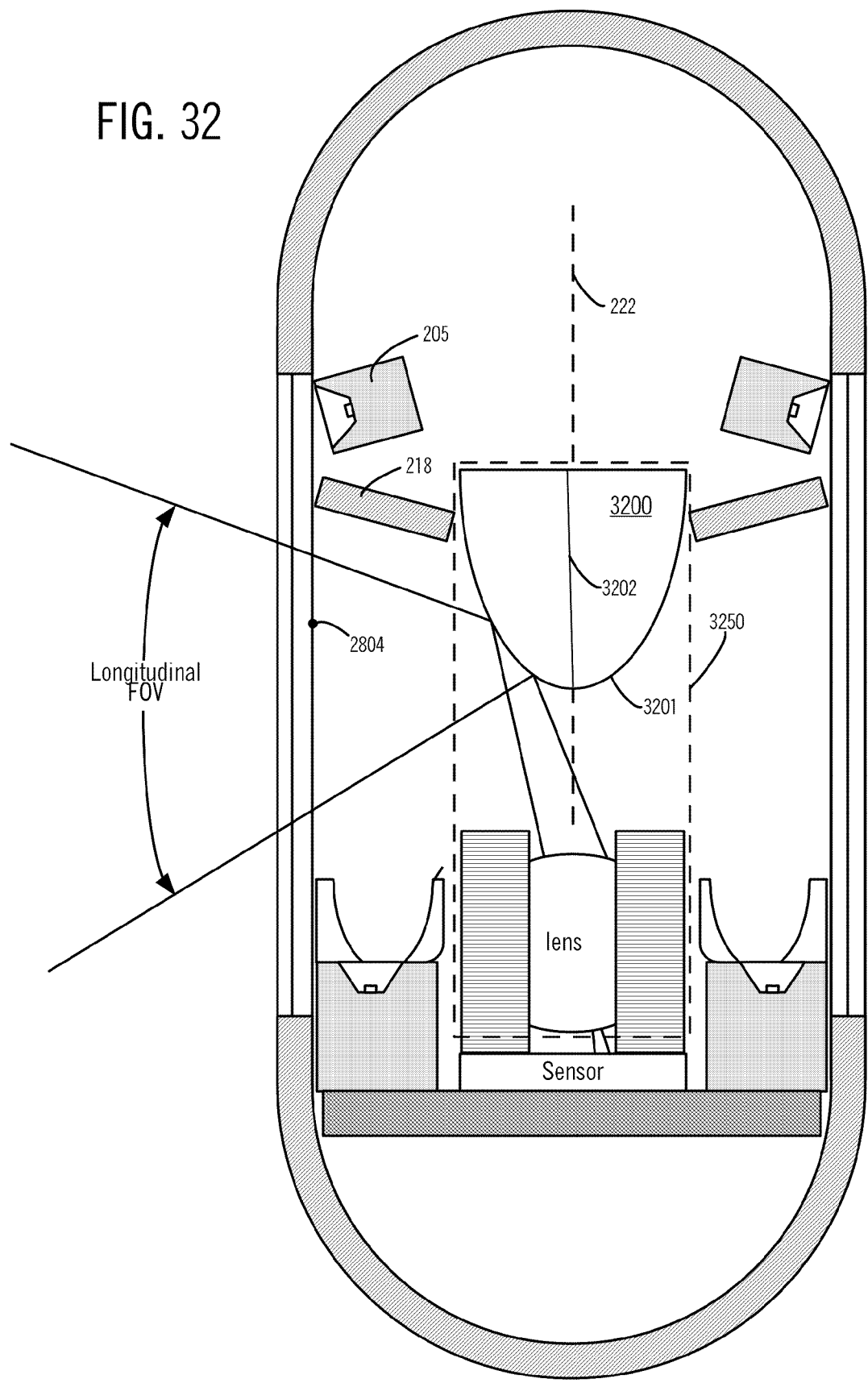

Some embodiments of an endoscope of the type described above use a radially-symmetric optical element within a camera, as illustrated in FIGS. 31 and 32. Specifically, a capsule endoscope of certain embodiments houses a panoramic camera which includes a single objective lens 3100 (FIG. 31) whose optical axis 3101 is substantially parallel to (e.g. within 20° of) the longitudinal axis 222 of the capsule endoscope. FIG. 32 shows another embodiment wherein the capsule endoscope houses a mirror 3200 with its optical axis 3202 being also substantially parallel to the longitudinal axis 222.

Panoramic cameras of the type shown in FIG. 31 provide a Field of View (FOV) that exceeds 180° but with an obscuration at the center of the FOV. For example, the FOV in one embodiment is a full 3600 in latitude (i.e. in all radial directions in the cross-sectional view shown in FIG. 30). In this example, the longitudinal range of angles for the FOV span only 400 relative to a lateral plane perpendicular to the longitudinal axis and passing through the center of lens 3100, i.e.

the longitudinal FOV 3102 (FIG. 31) of this example spans 200° less 160° (angle of obscuration). Note that half of the angles 200° and 160° are illustrated in FIG. 31 as 3103 and 3104 respectively.

Panoramic annular lens 3100 of FIG. 31 is similar or identical to panoramic annular lenses (PALs) described in, for example, U.S. Pat. No. 4,566,763 and U.S. Pat. No. 5,473,474 both of which are incorporated by reference herein in their entirety. A capsule endoscope with a PAL imaging system is also described in US Patent Publication 20080143822 entitled "In vivo sensor with panoramic camera" filed by Kang-Huai Wang and Gordon Wilson on Dec. 19, 2006 which is incorporated by reference herein in its entirety.

In the embodiments illustrated in FIG. 32 surface 3201 of mirror 3200 is formed as a conicoid surface of revolution, such as a spheroid, paraboloid, hyperbaloid, or any aspheroidal shape depending on the embodiment. Note that in certain embodiments of FIG. 32, the objective optical system 3250 is similar or identical to a corresponding objective optical system of the type described in US Patent Publication 20050049462 entitled "Capsule Endoscope" filed by Masafumi Kanazawa on Aug. 31, 2004 which is incorporated by reference herein in its entirety. Several embodiments as shown in FIGS. 31 and 32 have a camera with a central axis coincident with a longitudinal axis 222 of a housing of the capsule endoscope, in other embodiments these two axes are not aligned, and may even be oriented at a predetermined angle relative to one another depending on the embodiment.

The image exposure in certain illustrative embodiments of the invention is determined by averaging pixel levels sensed in pre-defined sectors of sensor regions Q1-Q4 illustrated in FIG. 2O. The sector positions are adjusted to account for possible decenter of images on the sensors, but, roughly speaking, each of the four sensor regions Q1-Q4 illustrated in FIG. 2O is subdivided into 4 sectors. The 16 sectors of a sensor 232 (FIG. 24) are labeled as shown in FIG. 2O relative to labels of the corresponding LEDs. Sensor regions Q1-Q4 map to a cylindrical field of view, and therefore sensor regions Q1 and Q4 are adjacent to one another.

Figure 24:
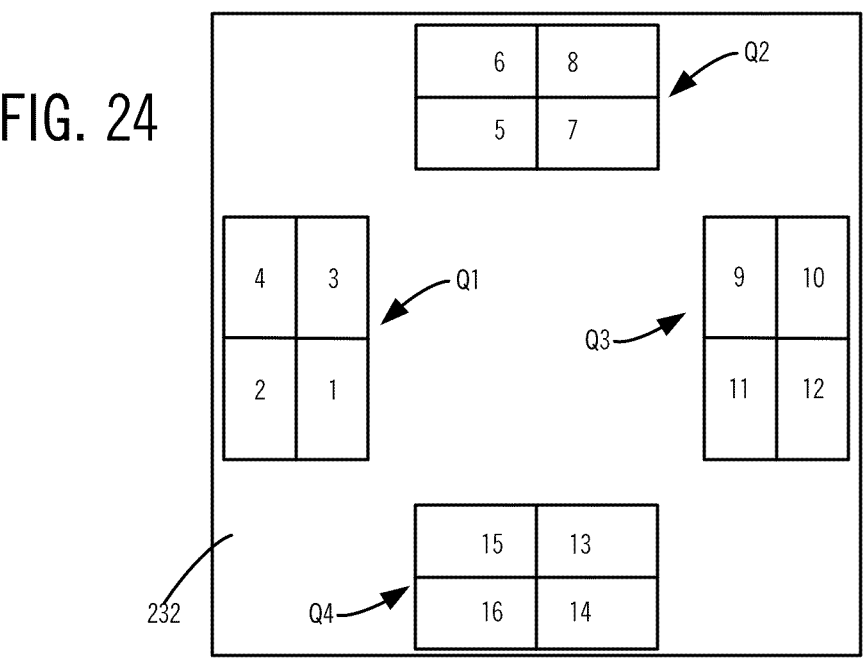
FIG. 24 illustrates a monolithic sensor chip wherein four regions Q1-Q4 are used to capture four portions of a panoramic 360° image.

Note that in some embodiments, each of sensor regions Q1-Q4 is one quadrant in a single monolithic sensor chip 232 as shown in FIG. 24. The illuminated scene is imaged by the camera onto the single monolithic sensor chip that captures four images in four sensor regions, labeled Q1-Q4. Each sensor region is itself divided into four sectors by two perpendicular lines and the sectors are labeled with sector numbers (as shown in FIG. 24). As noted above, each sector is labeled relative to the corresponding LED as shown in FIG. 2O.

Several embodiments of an endoscope use sixteen LEDs, including eight LEDs located above an annular mirror 218 (FIG. 2E) that are labeled with odd numbers, and eight LEDs located in a lower portion of the endoscope that are labeled with even numbers. The sixteen LEDs are all turned on sequentially, one after another, in rapid succession, to generate a panoramic image on sensor 232.

The luminous energy recorded by each pixel in the sensor chip is proportional to the illuminating luminous energy incident upon that portion of the scene imaged onto the pixel. The constant of proportionality depends, or efficiency with which scattered light is collected by the sensor, depends on many factors including the reflectance of the objects in the scene, the f# of the camera. Note that f# is the light-collection ability of a lens, the smaller the f# the more light is collected. For example, the f# of a lens is related as an inverse square of the amount of light collected.

The location and orientation of the LEDs is such that each LED principally affects the illumination of one corresponding sensor sector, although "cross talk", i.e. illumination of a sector by a non-corresponding LED, also is significant. For the ith sector, the exposure is given by averaging the signal levels a of the N pixels in the sector $$v_i = \frac{1}{N}\sum_{k}^{N} \sigma_k^{1/\Gamma}.$$

In the above equation, v denotes the radiant energy (also called luminous energy) received by the sensor and integrated over an area.

If the averaging is done before gamma correction, $\Gamma=1$. Otherwise, $\Gamma$ is the gamma factor, e.g. 2.2. Averaging after gamma correction may produce better results with high contrast images, but that is an open question.

Let $u_i^{(n)}$ be the luminous energy of the ith LED for exposure n. Assuming that the LEDs have linear L-I curves, $u_i^{(n)}$ is proportional to the integrated LED drive current integrated over exposure time τ

$$u_i^{(n)} \propto \int_0^\tau I_i^{(n)}(t)dt,$$

Note that in the above equation, u denotes the energy output by an LED. Since illuminance adds linearly, $$v = Au.$$

For a design of an endoscope as illustrated in FIGS. 17 and 18, A is a square matrix with the diagonal elements dominating. A is not constant but depends on the shape of the body cavity and the endoscope's orientation within it. Typically, we desire the illumination to be the same in all sectors. Let the target exposure be $\tilde{v}_i = v_0$. In principle the needed LED energies can be determined as $$u = A^{-1}\tilde{v}.$$

However, A is not known exactly.

The LED energies for the next frame $u^{(n+1)}$ may be estimated based on $u^{(n)}$ and $v^{(n)}$ for the current frame n $$u^{(n+1)} = u^{(n)} + B(\tilde{v} - v^{(n)}) \tag{0.1}$$

If $B = A^{-1}$ then we expect exact convergence to the desired exposure in the next frame. In order to make the illumination control method more stable, we estimate B such that $|B_{i,j}| < |A_{i,j}^{-1}|$ for all i and j. Also, we include off-diagonal elements to account for cross talk from neighboring LEDs. The optimal matrix B depends on the endoscope and/or tissue geometry. For example, the cross talk increases as the lumen wall (i.e. wall of the body cavity, or tissue) recedes from the endoscope. Thus, the magnitude of current to off-diagonal elements increases with increasing endoscope-lumen distance. The lumen distance is not known. However, $u_i$ is correlated to the endoscope-lumen distance so $B_{i,j} = f(u_i, j)$. This relationship will be determined through raytrace modeling and experimentation.

Given these relationships, $u^{(n+1)}$ may be estimated straightforwardly.

$$B_{i,j} = \begin{cases} f_1(u_i) & j = i & i \text{ odd} \\ f_2(u_i) & j - i & i \text{ even} \\ f_3(u_i) & j = i + 1 & i \text{ odd} \\ f_4(u_i) & j - i - 1 & i \text{ even} \\ f_5(u_i) & j = i \pm 2 & i \text{ odd} \\ f_6(u_i) & j = i \pm 2 & i \text{ even} \\ f_7(u_i) & j = i - 1, i + 3 & i \text{ odd} \\ f_8(u_i) & j = 1 + 1, i - 3 & i \text{ even} \\ 0 & \text{otherwise} \end{cases}$$

and $$j \rightarrow \begin{cases} j + 16 & j < 1 \\ j - 16 & j > 16 \end{cases}$$

The functions $f_m(u_i)$, m=1,2, ..., 6, are tabulated.

$$f_m(u_i) = \begin{cases} \rho \Gamma a_{1m} & 0 < u_i < \rho u_1 \\ \rho \Gamma_{2m} & \rho u_1 < u_i < \rho u_2 \\ \vdots \\ \rho \Gamma a_{nm} & \rho u_{n-1} < u_i < \rho u_n \end{cases}$$

where n is a reasonably small number ~4. Γ is a feedback gain. If Γ is too high, the convergence will be unstable. If Γ is too low, the convergence will be slow. ρ is adjusted to account for differences in the average reflectivity of the object (test cylinder or colon). For the white test cylinder $\rho \approx 0.95$. For the colon $\rho \approx 0.3$.

The bottom LEDs (which are used for short range illumination) most strongly affect the exposure when the lumen is close and the top LEDs are more effective when the lumen is farther away. Accordingly, to conserve energy in the endoscope, the value of $u_i$ is capped at a maximum value $u_{max\ upper}$ for i odd. After initially calculating $u^{(n+1)}$, any upper LED values of the vector that exceed $u_{max\ upper}$ would be reduced to that value. Depending on the embodiment, upper LED values may be limited differently, e.g. by using a different matrix B.

If the lumen is touching the endoscope, the top LEDs (which are used for long-range illumination) have very little impact on the exposure. Thus, it could happen that the amount of current to these LEDs is increased to a high value, which would waste power. When this condition occurs, the energy of the upper LED (in the long-range light source) is limited to maximum value $u_{max\ upper}$. The best indicator of this condition is the LED level for a neighboring lower LED. If $u_{i+1}^n < b_1$, then we require $u_i^{(n)} < b_2$.

If an LED drive $u_k$ is capped and $\tilde{v}_k - v_k^{(n)} > 0$ then $u_k$ does not change in the next iteration. However, the matrix elements are based on the assumption that it will increase and other LEDs may not converge properly. Similarly, if $u_k = u_{min}$, where $u_{min}$ is the minimum LED drive (typically zero or one) and $\tilde{v}_k - v_k^{(n)} < 0$, a similar problem occurs. To remedy the problem with either set of conditions, we temporarily set some matrix elements to zero $$B'_{i,j} = \begin{cases} 0 & j = k, j \neq i \\ B_{i,j} & \text{otherwise} \end{cases}$$

Determining LED drive levels: $u_i$ is the luminous energy. Due to variations among LED efficiencies, the electrical charge required to achieve that energy will vary somewhat. Let $u_i = \alpha_i q_i$, where $q_i$ is the LED drive value and $\alpha_i$ is the efficiency of the ith LED. It may be convenient to choose the nominal efficiencies to be approximately one $q_i$ and $u_i$ fall between 0 and 255.

The efficiencies can be determined by calibration. In the current final-test plan, the illumination control method is run with the endoscope in a uniform white cylinder for a number of iterations. The resulting image is examined for uniformity. Also, the LED drive levels $q_i$ are recorded. If the test conditions are symmetric, then all the luminous energies should be equivalent for all upper and lower LEDs respectively.

$u_i = u_{odd} = \alpha_i q_i$ for all i odd $u_i = u_{even} = \alpha_i q_i$ for all i even Thus, the efficiencies $\alpha_i$ are deduced.

During calibration, α is not known. A constant is chosen as an initial guess. A typical value might be 0.2 mA-1, if the maximum value of u is 255. The initial guess value may be 1.

The above-described principles are implemented by appropriately programming a processor in an endoscope to perform a method illustrated in FIG. 2I. Specifically, the processor starts in act 2101 (see FIG. 2I), by setting the frame number to zero. Then in act 2102, the processor looks up initial values of LED drives namely the vector u(n) and LED drive cap values u(cap). The initial values in vector u(n) at the beginning when the endoscope is first turned on are all 0, in one example. Note that u(cap) is determined by experiment and is set to as low as possible to minimize ghosts while still achieving good uniformity at a variety of distances D1-D4 as described above in reference to FIGS. 2I and 2K. Note that the energy of the lower LED (in the short-range light source) is limited to the maximum value u(cap).

Referring to FIG. 2I, the processor enters a loop starting with act 2103. Note that act 2103 itself is repeatedly performed for each element $n_i^{(n)}$, wherein the processor checks if $u_i^{(n)}$ is greater than ui(cap) and if so saves the value of ui(cap) as $u_i^{(n)}$. After performing act 2103 for each element $u_i^{(n)}$, the processor then proceeds to act 2104. In act 2104, the processor sets the LED drives to generate the current in vector u(n) and then proceeds to act 2106 to capture the image. In act 2104, the processor also performs an act 2105 to determine the matrix B(n)(u(n)) based on the LED drives, simultaneously or contemporaneously with acts 2106-2109.

Note that the values of the LED drives are proportional to $u_i^{(n)}$ depending on the efficiency of the LED. After act 2106, the processor goes to act 2107 and calculates an average (or other such function) of luminance value, for each sector of image sensor—vector v(n).

In some embodiments, the pixel values (e.g. 50,000 pixels in a sector) are simply summed up and divided by their number so as to obtain a simple average, although other embodiments may use a weighted average. Some embodiments exclude outliers (e.g. all saturated pixels or some maximum percentage of saturated pixels). Yet another embodiment uses a median instead of an average.

Note that in act 2107, a more complicated function than a simple average is computed in several embodiments. For example, in some embodiments, pixels with luminance values above or below a preset threshold are rejected, i.e. not used in computing the result. In one illustrative embodiment, the pixel value of 255 in an 8 bit number is rejected as being above a preset upper threshold, because this number may represent any over-exposed value, even a value resulting from specular reflection. In the just-described illustrative embodiment, the pixel values of 2, 1 and 0 are also rejected as being below a preset lower threshold, because these values may represent noise.

After act 2107, the processor goes to act 2108, and calculates a difference between target luminance vt and measured luminance for each sector—vector (v(t)−v(n)). Typically, target luminance vt is a scalar constant, e.g. 60 out of a maximum of 255.

Next, the processor goes to act 2109, and computes new LED drives, as u(n)=u(n)+B(n)(v(t)−v(n)). Note that in act 2109, the processor receives the result of act 2105, i.e. the matrix B(n)(u(n)).

Figure 22:
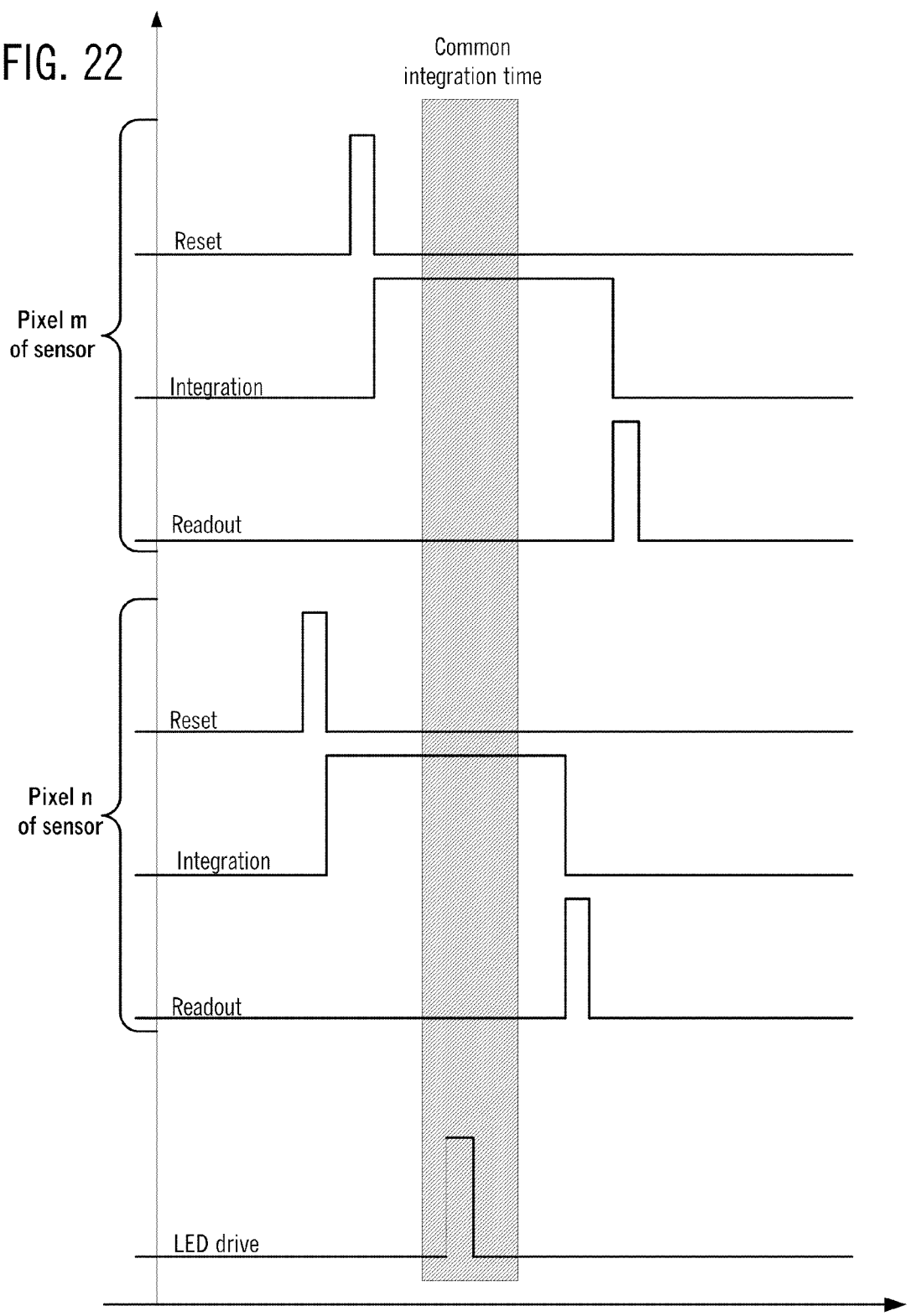
FIG. 22 illustrates, in a graph, timing relationships between signals between a controller, LEDs and sensors in an endoscope in accordance with the invention.

After act 2109, the processor goes to act 2110 to increment n, and then iterates back to the beginning of the loop, specifically to act 2103. A graph of timing relationships between signals between a controller, LEDs and sensors in an endoscope is illustrated in FIG. 22. Note that the LEDs are turned on during an integration time for pixels in the sensors, thereby to capture an image formed by light that is emitted by the LEDs and reflected by tissue.

Figure 33:
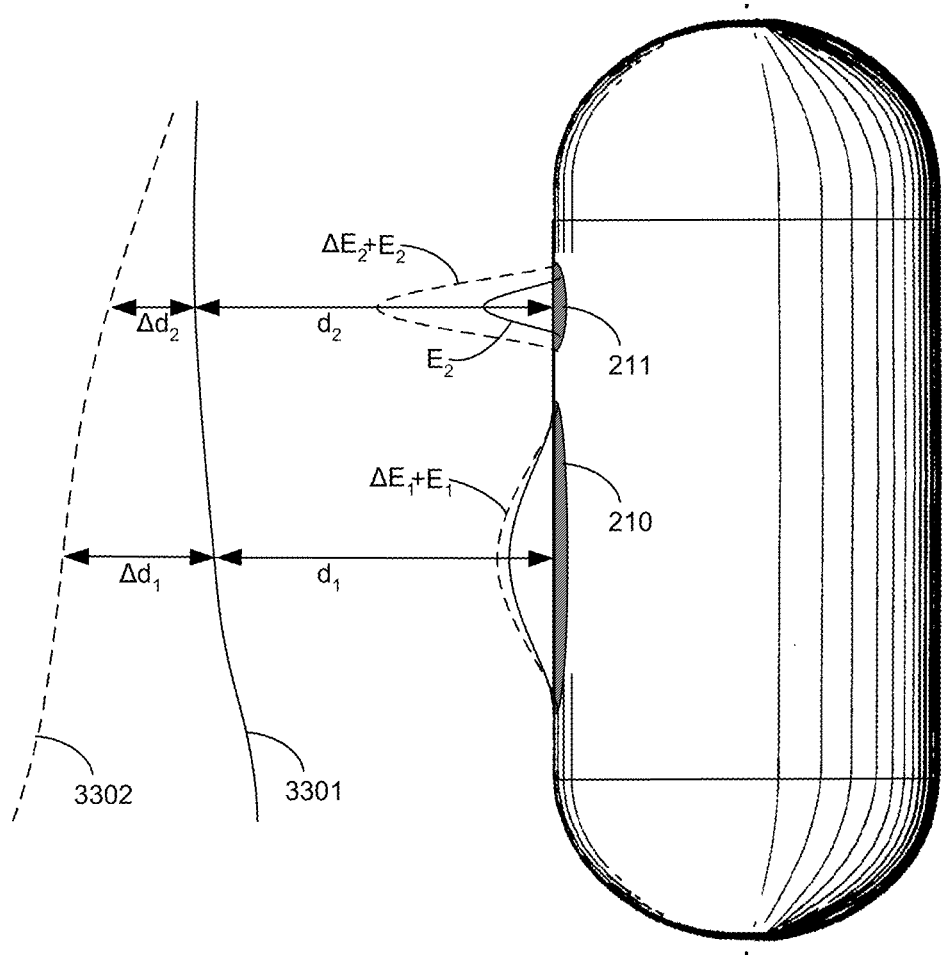
FIG. 33 illustrates changes in energy emitted in accordance with this invention relative to changes in distance of two illumination regions of an endoscope from a gastrointestinal tract.

As noted above, energy emitted in short-range electromagnetic radiation is capped or limited to use energy efficiently in some embodiments. Referring to FIG. 33, endoscope 200 moves from a current location 3301 to a new location 3302 at which an increase $\Delta d1$ (e.g. 3 mm) in a distance d1 (e.g. 13 mm) of the short-range illumination region from the gastrointestinal tract is greater than an increase $\Delta d2$ (e.g. 6 mm) in distance d2 (e.g. 14 mm) of the long-range illumination region from the gastrointestinal tract (when measured in a common direction). In response to such movement, some embodiments of an endoscope in accordance with the invention automatically increase radiant energy E2 (e.g. 5 micro Joules) emitted in the long-range electromagnetic radiation from the long-range illumination region by an amount $\Delta E2$ (e.g. 1 micro Joule) which is larger than an increase $\Delta E1$ (e.g. 0.1 micro Joule) in radiant energy E1 (e.g. 5 micro Joules) emitted in the short-range electromagnetic radiation. After these increases, endoscope 200 stores in its memory another portion of another image of the tract from the new location. The current inventor submits that it is non-obvious to make 66 $E1 < \Delta E2$ in response to a movement which makes $\Delta d1 > \Delta d2$. As noted above, in some embodiments E1 is capped to a maximum value $u_{max\;upper}$. Hence, in some situations wherein such a preset limit is reached, $\Delta E1$ is kept at zero in order to conserve energy even if $\Delta d1 > \Delta d2$.

Numerous modifications and adaptations of the embodiments described herein will be apparent to the skilled artisan in view of the disclosure.

For example, some embodiments of a device include a housing sufficiently small to be insertable into a gastrointestinal tract of a human, a camera enclosed within said housing, wherein an optical axis of the camera intersects the housing at an intersection point, a first source of electromagnetic radiation enclosed within said housing, with first electromagnetic radiation from the first source exiting through a first region of the housing on operation of the first source, wherein the first source is positioned within the housing such that the first region contains the intersection point of the optical axis with the housing, a second source of electromagnetic radiation enclosed within said housing, with second electromagnetic radiation from the second source exiting through a second region of the housing on operation of the second source, wherein the second source is positioned within the housing such that the intersection point of the optical axis with the housing is located outside the second region.

As another example, certain embodiments of a device include a housing sufficiently small to be swallowed, a camera enclosed by the housing, the endoscope having a field of view defined by a largest image effectively transmitted by the endoscope to an external computer, a plurality of sources of light enclosed within the housing, wherein each source in the plurality of sources has an aperture positioned within the housing to emit rays reflected by the housing and forming a mirror image of said aperture outside of the field of view of the endoscope.

Also, instead of using a CPC as optical element 216, alternative embodiments of endoscope 200 in accordance with the invention use annular angular concentrators having other types of cross-sections that may less effectively reduce angular divergence, such as a cone or a paraboloid. In two illustrative embodiments, a concentrator cross-section that is used in an annular angular concentrator has the same shape as a handheld flashlight's concentrator or an automobile headlight's concentrator.

Some embodiments of an endoscope of the type described herein minimize the amount of light received by a sensor after reflection from the housing of the endoscope by one or more techniques, such as (a) employing optical elements (such as the CPC) to reduce a range of angles through which light is emitted by a source (such as a short-range source) and (b) providing one or more sources (such as a long-range source) that emit a majority (or most) of the light through a region of the housing through which image forming rays (to the sensor) do not pass.

In some illustrative embodiments, a device in accordance with the invention comprises: a housing sufficiently small to travel through a gastrointestinal tract of a human, a first source of electromagnetic radiation enclosed within the housing, with first electromagnetic radiation from the first source exiting through a first region of said housing, a second source of electromagnetic radiation enclosed within said housing, with second electromagnetic radiation from the second source exiting through a second region of said housing, a camera enclosed within the housing; wherein the endoscope has a field of view defined by a range of angles through which a cropped image of the gastrointestinal tract is captured by a sensor in the camera, on operation of the camera, wherein the cropped image is formed by reflection of at least a portion of said first electromagnetic radiation and a portion of said second electromagnetic radiation from the gastrointestinal tract, wherein the field of view intersects the housing at a third region overlapping at least a portion of the first region; and wherein the camera has an optical axis intersecting the housing at a point in said portion of the first region overlapped by the third region, the point being outside the second region.

In several illustrative embodiments, a device in accordance with the invention includes a housing sufficiently small to be enclosed within an organ of a human; at least one upper source of electromagnetic radiation enclosed within the housing; wherein, on operation of the at least one upper source, electromagnetic radiation, of a first intensity that is at least a first predetermined percentage (e.g. almost all or over 90%) of maximum intensity from the at least one upper source, exits through an upper illumination region of a surface of the housing; at least one lower source of electromagnetic radiation enclosed within the housing; wherein, on operation of the at least one lower source, electromagnetic radiation, of a second intensity that is at least a second predetermined percentage (e.g. 37%) of maximum intensity from the at least one lower source, exits through a lower illumination region of the surface of the housing; wherein the lower illumination region is larger than (e.g. 1.2 times larger or 1.5 times larger or even 5 times larger) the upper illumination region; at least one camera enclosed within the housing; wherein the at least one camera forms an image of light emitted from at least one of the lower illumination region and the upper illumination region and entering the housing after reflection from a surface of the organ through the lower illumination region.

Additionally, note that a "majority of electromagnetic radiation" as used herein refers to a majority of power.

Furthermore, note that as region 212 (FIGS. 2J, 28A-28D) demarcates reflected light entering endoscope 200 which is used in forming a diagnosable image, any region outside of the boundary of region 212 is referred to herein as a non-imaging region. Hence, region 211 is a non-imaging region in FIG. 28A. Accordingly, a majority of electromagnetic radiation emitted by a long-range light source of some embodiments exits the housing of endoscope 200 through a non-imaging region (i.e. any region outside of boundary 212). Moreover, in such embodiments, a majority of electromagnetic radiation emitted by a short-range light source exits the housing of endoscope 200 outside of the non-imaging region, i.e. exits through the region 212.

Note that an organ as used herein can be a uterus or any part of a gastrointestinal tract (such as a colon, small bowel (small intestine), esophegous, stomach, rectum). Accordingly, an apparatus as described herein can be used to obtain images of any organ of a human or other such mammal.

In certain embodiments, short-range illumination region 210 is significantly larger (e.g. several times larger, such as 2 times larger, 3 times larger, or even 5 times larger) than long-range illumination region 211. This relationship between the two types of illumination regions is illustrated in FIGS. 2B and 2C wherein each of overlapping regions 210A, 210B and 210C for short-range illumination are individually larger than long-range illumination region 211, and hence their combination into region 210 is significantly larger than region 211.

Finally, although endoscope 1900 has been illustrated in FIG. 19 as enclosing a single camera located in one dome at one end of a capsule, a similar endoscope 3400 illustrated in FIG. 34 encloses two cameras at the two ends of such a capsule. Specifically, endoscope 3400 has two apertures 3405 and 3406 and two pupils P1 and P2 respectively through which reflected light from a gastrointestinal tract is received by two sensors 3401 and 3402 respectively. Sensors 3401 and 3402 together constitute a set of sensors that generate image data at different positions of endoscope 3400 relative to the tract. Image data obtained by the set of sensors (i.e. sensors 3401 and 3402 in FIG. 34) is supplied to a transmitter 3403 that in turn supplies the image data to an external computer (after optional cropping), for use in generation and display of a diagnosable image.

In some embodiments, an endoscope of the type described above generates first electromagnetic radiation using a first source, and at least a first fraction of the first electromagnetic radiation from the first source is incident on the first region after reflection by an optical element located between the first source and the housing and at least a second fraction of the first electromagnetic radiation from the first source is incident on the first region without reflection by the optical element. In several such embodiments, the first fraction is greater than the second fraction, wherein the optical element is on a first side of a plane and the first source is on a second side of the plane and all electromagnetic radiation from the first source is emitted on the second side of the plane, and the endoscope generates the second electromagnetic radiation using a second source, a majority of the second electromagnetic radiation from the second source being incident on the second region without reflection between the second source and the housing, wherein each source is enclosed within a housing of the endoscope and each source comprises a pair of terminals with current passing therebetween and at least one emitter of electromagnetic radiation is powered through the pair of terminals.

In certain embodiments, the endoscope transmits a majority of the first electromagnetic radiation after reflection by an optical element within the endoscope, wherein the optical element is on a first side of a plane and a first source of the first electromagnetic radiation is on a second side of the plane and all electromagnetic radiation from the first source is emitted on the second side of the plane, and the endoscope transmits a majority of the second electromagnetic radiation without reflection by the optical element.

What is claimed is:

1. An endoscope comprising:
   a housing sufficiently small to travel through a gastrointestinal tract of a human, the housing comprising a tubular wall;
   a transmitter enclosed within said housing, to transmit image data to an external device;
   a set of one or more sensors enclosed within said housing and coupled to said transmitter, said set supplying said image data to said transmitter;
   a first source enclosed within said housing, to generate first electromagnetic radiation exiting said housing;
   wherein said first source is positioned at a first location whereby said first electromagnetic radiation passes through a first region of the housing defined by a first intersection of said first electromagnetic radiation with a surface of the housing;
   a second source enclosed within said housing, to generate second electromagnetic radiation exiting said housing;
   wherein said second source is positioned at a second location whereby the second electromagnetic radiation passes through a second region of the housing defined by a second intersection of said second electromagnetic radiation with the surface of the housing;
   wherein the first region is larger than the second region;
   wherein a third electromagnetic radiation enters said housing through said tubular wall, to form said image data; and
   wherein at least a portion of said third electromagnetic radiation arises from reflection of a fraction of said first and second electromagnetic radiation.

2. The endoscope of claim 1 wherein:
   the endoscope further comprises an additional wall enclosed within the housing;
   a plurality of paths correspond to a plurality of rays originating from a specific source in a group consisting of the first source and the second source, the plurality of paths pass through the additional wall to reach the housing and reflect therefrom to form within said housing, a mirror image of the specific source, in the absence of the additional wall; and
   wherein the additional wall is opaque and positioned adjacent to the specific source, to block passage of the plurality of rays along said paths to prevent said formation of said mirror image by said plurality of rays.

3. The endoscope of claim 2 wherein:
   the additional wall is annular.

4. The endoscope of claim 1 wherein:
the housing has an aspect ratio greater than one;
a longitudinal plane passes through a longitudinal axis of the housing;
the longitudinal plane passes through each of said first source and said second source; and said first source is offset from said second source in a direction of said longitudinal axis.

5. The endoscope of claim 4 wherein:
a majority of the first electromagnetic radiation exiting the housing passes through the third region.

6. The endoscope of claim 5 wherein:
said set is coupled to said transmitter by a processor comprised in the endoscope and enclosed within said housing;
additional electromagnetic radiation enters said housing to form additional data also supplied by said set to said processor; and
said processor excludes said additional data to obtain said image data supplied to said transmitter.

7. The endoscope of claim 6 wherein:
at least a portion of said additional electromagnetic radiation arises from reflection by said surface, of a fourth electromagnetic radiation from at least one of the first source or the second source.

8. The endoscope of claim 4 wherein:
a portion of the first electromagnetic radiation is reflected by a mirror in the endoscope before passing through the first region of the housing; and
another portion of the first electromagnetic radiation passes through the first region of the housing without reflection by said mirror.

9. The endoscope of claim 8 wherein:
a sensor in said set is comprised in a camera configured to capture at least a portion of the third electromagnetic radiation entering the housing; and
a first distance between the first source and an optical axis of the camera is smaller than a second distance between the first source and the minor.

10. The endoscope of claim 4 further comprising:
a baffle enclosed within the housing;
wherein the baffle is positioned to block rays originating in at least one of the first source and the second source from forming a virtual image that can be captured by the set of sensors.

11. The endoscope of claim 1 wherein:
a third region of the housing is defined by an intersection of the surface of the housing with said third electromagnetic radiation; and
a majority of the second electromagnetic radiation passes through a portion of the second region not overlapping the third region.

12. The endoscope of claim 11 wherein:
almost all of the second electromagnetic radiation passes through said portion of the second region.

13. The endoscope of claim 11 wherein:
a majority of the first region overlaps the third region.

14. The endoscope of claim 11 wherein:
the endoscope further comprises an additional wall enclosed within the housing;
a plurality of paths correspond to a plurality of rays originating from a specific source in a group consisting of the first source and the second source, the plurality of paths pass through the additional wall to reach the housing and reflect therefrom to form within said housing, a minor image of the specific source, in the absence of the additional wall;
wherein the additional wall is opaque and positioned adjacent to the specific source, to block passage of the plurality of rays along said paths to prevent said formation of said mirror image by said plurality of rays.

15. The endoscope of claim 11 wherein:
at least a portion of the first electromagnetic radiation and at least a portion of the second electromagnetic radiation are provided in a same radial direction.

16. The endoscope of claim 1 wherein:
a majority of the first electromagnetic radiation exiting the housing passes through a third region defined by an intersection of the surface of the housing with said third electromagnetic radiation.

17. The endoscope of claim 1 wherein:
the first region is at least several times larger than the second region.

18. The endoscope of claim 1 wherein:
a portion of the first electromagnetic radiation is reflected by a mirror in the endoscope before passing through the first region of the housing; and
another portion of the first electromagnetic radiation passes through the first region of the housing without reflection by said mirror.

19. The endoscope of claim 18 wherein:
a sensor in said set is comprised in a camera configured to capture at least a portion of the third electromagnetic radiation entering the housing; and
a first distance between the first source and an optical axis of the camera is smaller than a second distance between the first source and the mirror.

20. The endoscope of claim 18 wherein:
a sensor in said set is comprised in a camera configured to capture at least a portion of the third electromagnetic radiation entering the housing;
the housing has an aspect ratio greater than one; and
a first offset in a direction of a longitudinal axis of the housing, between the first source and an optical axis of the camera, is less than a second offset in said direction, between the first source and a minor in the endoscope.

21. The endoscope of claim 1 wherein:
a sensor in said set is comprised in a camera configured to capture at least a portion of the third electromagnetic radiation entering the housing;
a first distance between the first source and an optical axis of the camera is larger than a second distance between the first source and a mirrored surface in the endoscope; and
a portion of the first electromagnetic radiation is reflected by the mirrored surface before passing through the first region of the housing.

22. The endoscope of claim 1 further comprising:
a mirrored surface oriented to reduce angular divergence of a portion of the first electromagnetic radiation incident thereon.

23. The endoscope of claim 1 wherein:
wherein said third electromagnetic radiation enters said housing to form said image data.

24. The endoscope of claim 1 further comprising:
a baffle and a lens enclosed within the housing;
wherein a first virtual image of the baffle blocks a line-of-sight between a pupil and a second virtual image of at least one of the first source and the second source, the second virtual image being formed within a field of view of the lens in the absence of the first virtual image.

25. The endoscope of claim 1 further comprising:
a baffle enclosed within the housing;
wherein the baffle is positioned to block rays originating in at least one of the first source and the second source from forming a virtual image that can be captured by the set of sensors.

26. The endoscope of claim 1 wherein further comprising:
a pair of domes capping the tubular wall at opposite ends thereof, to form a capsule; and
a baffle positioned between a window in the tubular wall and at least one of the first source and the second source.

27. The endoscope of claim 1 further comprising:
a mirror enclosed within the housing;
wherein the minor block rays originating in at least one of the first source and the second source from forming a virtual image that can be captured by the set of sensors.

28. The endoscope of claim 1 wherein:
said image data represents a diagnosable image at a specific location in a gastrointestinal tract and excludes additional data which represents an unduly bright region.

29. The endoscope of claim 1 wherein:
the first region is at least 1.2 times larger than the second region.

30. The endoscope of claim 1 wherein:
the first region is at least 1.5 times larger than the second region.

31. The endoscope of claim 1 wherein:
the first region is at least 2 times larger than the second region.

32. The endoscope of claim 1 wherein:
at least a portion of the first electromagnetic radiation and at least a portion of the second electromagnetic radiation are provided in a same radial direction.

33. The endoscope of claim 1 wherein:
a majority of said first and second electromagnetic radiation exits from the endoscope through the tubular wall.

34. The endoscope of claim 1 wherein:
the housing comprises a pair of domes capping the tubular wall at opposite ends thereof, to form a capsule; and
the domes do not receive the third electromagnetic radiation that forms said image data.

35. The endoscope of claim 1 wherein:
the housing comprises a pair of domes capping the tubular wall at opposite ends thereof, to form a capsule; and
the domes do not transmit the first and second electromagnetic radiation exiting the endoscope.

36. The endoscope of claim 1 further comprising:
a pupil having an optical axis that intersects with an internal surface of the housing;
wherein the housing has an aspect ratio greater than one;
wherein the first source is offset from the optical axis in a longitudinal direction of the endoscope; and
wherein the second source is offset from the optical axis in the longitudinal direction opposite to the first source.

37. The endoscope of claim 1 wherein:
the first source and the second source generate different amounts of energy relative to each other depending on a distance of tissue from the endoscope.

38. The endoscope of claim 1 wherein:
an imaging region on the housing is defined by a field of view of the set of one or more sensors;
the imaging region at least partially overlaps the first region; and
the imaging region does not overlap the second region.

39. The endoscope of claim 1 wherein the first source comprises:
an emitter; and
an optical element that splits electromagnetic radiation received from the emitter.

40. The endoscope of Claim 1 further comprising:
an optical element;
wherein the optical element reduces angular dispersion of at least one fraction of the first electromagnetic radiation.

41. The endoscope of Claim 1 further comprising:
an optical element surrounded by the tubular wall;
wherein the optical element is of an annular shape comprising a plurality of spokes between an inner wall and an outer wall that face each other.

42. The endoscope of Claim 1 further comprising:
an optical element surrounded by the tubular wall;
wherein a surface of the optical element is a surface of a truncated compound parabolic concentrator.

43. The endoscope of Claim 1 further comprising:
an optical element;
wherein:
the first source comprises an emitter encapsulated within a cavity; and
an aperture of the cavity is located only partially under an input aperture of the optical element.

44. The endoscope of Claim 1 further comprising:
an optical element; and
an annular minor configured to reflect out of the endoscope, one portion of the first electromagnetic radiation that exits an aperture of the optical element;
wherein another portion of the first electromagnetic radiation that exits the aperture, exits out of the endoscope directly from the aperture.

45. The endoscope of claim 1 further comprising an optical element, wherein:
the endoscope transmits a majority of the first electromagnetic radiation after reflection by said optical element; and
the endoscope transmits a majority of the second electromagnetic radiation without reflection by said optical element.

46. The endoscope of claim 1 further comprising an optical element located between the first source and the housing, wherein:
at least a first fraction of the first electromagnetic radiation from the first source is incident on the first region after reflection by the optical element;
at least a second fraction of the first electromagnetic radiation from the first source is incident on the first region without reflection by the optical element; and
said first fraction is greater than said second fraction.

47. A method comprising:
using a first source enclosed within a housing of an endoscope, to generate first electromagnetic radiation exiting the housing;
wherein the housing is sufficiently small to travel through a gastrointestinal tract of a human, the housing comprising a tubular wall;
wherein said first source is positioned at a first location in the housing whereby said first electromagnetic radiation passes through a first region of the housing defined by a first intersection of said first electromagnetic radiation with a surface of the housing;
using a second source enclosed within said housing, to generate second electromagnetic radiation exiting said housing;

wherein said second source is positioned at a second location in the housing whereby the second electromagnetic radiation passes through a second region of the housing defined by a second intersection of said second electromagnetic radiation with the surface of the housing;

using a transmitter enclosed within the housing, to transmit image data to an external device;

wherein a set of one or more sensors enclosed within said housing are coupled to said transmitter, said set supplying said image data to said transmitter;

wherein the first region is larger than the second region;

wherein a majority of a third electromagnetic radiation enters said housing through said tubular wall, to form said image data; and wherein at least a portion of said third electromagnetic radiation arises from reflection of a fraction of said first and second electromagnetic radiation.

48. The method of claim 47 wherein said using the first source and said using the second source are performed when said endoscope is at a first location relative to the gastrointestinal tract, the method further comprising:

in response to movement of said endoscope to a second location at which a first increase $\Delta d$ resulting from said movement, in a first distance dl of the first region from the gastrointestinal tract is greater than a second increase $\Delta d2$ resulting from said movement, in a second distance d2 of the second region from the gastrointestinal tract when measured in a common direction, said endoscope automatically increasing radiant energy E2 emitted in the second electromagnetic radiation from said second region by a second amount $\Delta E2$ while increasing radiant energy emitted in the first electromagnetic radiation by a first amount $\Delta E1$, said first amount $\Delta E1$ being smaller than said second amount $\Delta E2$; and subsequent to said increasings, said endoscope storing in memory another portion of another image of said tract from said second location.

49. The method of claim 47 wherein:

at least a first fraction of the first electromagnetic radiation from the first source is incident on the first region after reflection by an optical element located between the first source and the housing and at least a second fraction of the first electromagnetic radiation from the first source is incident on the first region without reflection by the optical element, said first fraction being greater than said second fraction.

50. The method of claim 47 wherein:

a majority of the second electromagnetic radiation from the second source is incident on the second region without reflection between the second source and the housing.

51. The method of claim 47 wherein:

said endoscope transmits a majority of the first electromagnetic radiation after reflection by an optical element within said endoscope; and said endoscope transmits a majority of the second electromagnetic radiation without reflection by said optical element.

52. The method of claim 47 further comprising:

said endoscope calculating an average luminance value for each sector in a plurality of sectors used to sense said image;

said endoscope calculating a difference between the average luminance value calculated for each sector and a target luminance value for said each sector; and said endoscope computing a drive current for generating the second electromagnetic radiation, based at least partially on said difference.

53. The method of claim 52 wherein:

a change in said drive current is obtained based on a linear combination of a plurality of said differences individually calculated for each sector in said plurality of sectors.

54. The method of claim 53 wherein:

said linear combination comprises multiplication of a vector of said differences with a matrix of values, each value being selected to be one of a plurality of predetermined values based on drive current.

* * * * *